United States Patent
Reed

(10) Patent No.: US 7,022,831 B1
(45) Date of Patent: *Apr. 4, 2006

(54) REGULATION OF BCL-2 GENE EXPRESSION

(75) Inventor: John C. Reed, Carlsbad, CA (US)

(73) Assignee: The Trustees of the University of Pennsylvania, Philadelphia, PA (US)

( * ) Notice: Subject to any disclaimer, the term of this patent is extended or adjusted under 35 U.S.C. 154(b) by 0 days.

This patent is subject to a terminal disclaimer.

(21) Appl. No.: 09/375,514

(22) Filed: Aug. 17, 1999

Related U.S. Application Data

(63) Continuation of application No. 09/080,285, filed on May 18, 1998, now Pat. No. 6,040,181, which is a continuation of application No. 08/465,485, filed on Jun. 5, 1995, now Pat. No. 5,831,066, which is a continuation of application No. 08/124,256, filed on Sep. 20, 1993, now abandoned, which is a continuation-in-part of application No. 07/840,716, filed on Feb. 21, 1992, now abandoned, which is a continuation-in-part of application No. 07/288,692, filed on Dec. 22, 1988, now abandoned.

(51) Int. Cl.
*C07H 21/04* (2006.01)
*A61K 48/00* (2006.01)

(52) U.S. Cl. ........................ 536/24.5; 514/44
(58) Field of Classification Search ............... 536/23.1, 536/24.5; 435/6, 375, 325, 366; 514/44
See application file for complete search history.

(56) References Cited

U.S. PATENT DOCUMENTS

| | | | |
|---|---|---|---|
| 4,525,358 A | 6/1985 | Baltes et al. | 514/255 |
| 4,999,290 A | 3/1991 | Lee | |
| 5,015,568 A | 5/1991 | Tsujimoto et al. | |
| 5,098,890 A | 3/1992 | Gerwitz | |
| 5,149,628 A | 9/1992 | Croce | |
| 5,202,429 A | 4/1993 | Tsujimoto et al. | |
| 5,459,251 A | 10/1995 | Tsujimoto et al. | |
| 5,475,096 A * | 12/1995 | Gold et al. | 536/23.1 |
| 5,478,941 A | 12/1995 | Cossement et al. | 544/383 |
| 5,585,479 A | 12/1996 | Hoke et al. | |
| 5,750,390 A * | 5/1998 | Thompson et al. | 435/195 |
| 5,831,066 A * | 11/1998 | Reed | 536/24.5 |
| 5,932,697 A * | 8/1999 | Caceci et al. | 530/350 |
| 6,005,095 A * | 12/1999 | Capaccioli et al. | |
| 6,040,181 A * | 3/2000 | Reed | 435/377 |

FOREIGN PATENT DOCUMENTS

| | | |
|---|---|---|
| EP | 0 058 146 | 8/1982 |
| EP | 340948 A1 * | 11/1989 |
| EP | 0 617 028 | 9/1994 |
| GB | 2 311 940 | 1/1997 |
| WO | WO 9213102 A1 * | 8/1992 |
| WO | WO-93/20200 | 10/1993 |
| WO | 94/06430 | 3/1994 |
| WO | WO 94/27426 | 12/1994 |
| WO | WO 96/27663 * | 9/1996 |

OTHER PUBLICATIONS

K. P. Paul, "ETAC: an Update", International Journal of Immunopathology and Pharmacology, vol. 10, No. 2, pp. 127-128, 1997.

U. Waln, "Allergic factors associated with the development of asthma and the influence of cetirizine in a double-blind, randomised, placebo-controlled trial: First results of ETAC", Pediatric Allergy and Immunology, vol. 9, No. 3, pp. 116-124, Aug. 1998.

L. Fasce et al., "Cetirizine Reduces ICAM-I on Epithelial Cells during Nasal Minimal Persistent Inflammation in Asymptomatic Children with Mite-Allergic Asthma", Int. Arch. Allergy Immunol. vol. 109, No. 3, pp. 272-276, 1996.

A. Brik et al., "Effect of cetirizine, a new histamine $H_1$ antagonist, on airway dynamics and responsiveness to inhaled histamine in mild asthma", vol. 80, No. 1, pp. 51-56, 1987.

J.O. Warner et al, "Determinants of total and specific IgE in infants with atopic dermatitis", Pediatric Allergy and Immunology, vol. 8, pp. 177-184, Nov. 1997.

J.H. Dijkman et al., "Prophylactic treatment of grass pollen-induced asthma with cetirizine", Clinical and Experimental Allergy, vol. 20, pp. 483-490, Sep. 1990.

C. De Vos et al., "Antihistamines and allergic asthma", Allergie et Immunologie, vol. 23, No. 9, pp. 396-401, Nov. 1991.

(Continued)

*Primary Examiner*—Sean McGarry
*Assistant Examiner*—Tracy Vivlemore
(74) *Attorney, Agent, or Firm*—Darby & Darby

(57) ABSTRACT

The present invention provides novel anticode oligomers and methods of using them for controlling the growth of cancer cells expressing the bcl-2 gene.

19 Claims, 16 Drawing Sheets

OTHER PUBLICATIONS

D. Tashkin et al., "Cetirizine inhibition of histamine-induced bronchospasm", vol. 59, pp. 49-52, Dec. 1987.

G. Bruttmann et al., "Protective effect of cetirizine in patients suffering from pollen asthma", Annals of Allergy, vol. 64, pp. 224-228, Feb. 1990.

H. Redier et al., "Inhibitory effect of cetirizine on the bronchial eosinophil recruitment induced by allergen inhalation challenge in allergic patients with asthma", Journal of Allergy and Clinical Immunology, vol. 90, No. 2, pp. 215-224, Aug. 1992.

J.B. Wasserfallen et al., "Effect of cetirizine, a new $H_1$ antihistamine, on the early and late allergic reactions in a bronchial provocation test with allergen", Journal of Allergy and Clinical Immunology, vol. 91, No. 6, pp. 1189-1197, Jun. 1993.

J.A. Grant et al., "Safety and efficacy of cetirizine (CET) in the prophylactic management of patients with seasonal allergic rhinitis (SAR) and asthma", vol. 91, No. 1, p. 197, Mar. 12-17, 1993.

"Medical researchers aim at fundamental better protection and treatment of the atopic child", ETAC Science, pp. 1-8, Jan. 1994.

"Asthma prevention in risk children: Cetirizine", pp. 61-62, 1995.

I. Trieloff, "Early treatment of the atopic child", pp. 390-391, 1995.

"The role of early intervention in childhood asthma therapy", pp. 8224-8227, 1998.

E. Bidat et al., "The treatment of childhood asthma", pp. 3021-3026, 1991.

L. Businco et al., "From atopic dermatitis to asthma", pp. 477-481, 1997.

B. Schwarz, "Treatment with cetirizine also for children", p 34, 1993.

S. Matsubara et al., "Effect of betotastine basilate on experimental asthma model in guinea pigs", pp. 31-36, 1997.

Toshiyuki Miyashita et al., Cancer Research, vol. No. 52, pp. 5407-5411, Oct. 1, 1992.

Toshiyuki Miyashita et al., Blood, vol. No. 81, pp. 151-157, Jan. 1, 1993.

J. C. Reed et al., Annals of Oncology, 1993, Page Nos. 61-65.

F. E. Cotter et al., Oncogene, vol. No. 9, pp. 3049-3055, Oct. 1994.

Shinichi Kitada et al., Antisense Research and Development, vol. 4, pp. 71-79, Summer 1994.

Shinichi Kitada et al., Antisense Research and Development, vol. 3, pp. 157-169, Summer 1993.

Reed et al., Cancer Res., 50, p. 5656, 1990.

Williams, Cell 65, p. 1097, 1991.

Strasser et al., Cell 67, p. 889, 1991.

Patent Cooperation Treaty (PCT) International Search Report dated Jan. 12, 1995.

C. Paoletti, "Anti-Sense Oligonucleotides as Potential Antitumour Agents: Prospective Views and Preliminary Results," Anti-Cancer Drug Design, vol. 2, pp. 325-331, 1988.

Stein et al., "Oligodeoxynucleotides as Inhibitors of Gene Expression: A Review," Cancer Research, vol. 48, pp. 2659-2668, May 15, 1988.

Eugen Uhlmann et al., "Antisense Oligonucleotides: A New Therapeutic Principle," Chemical Reviews, vol. 90, No. 4, pp. 544-584, Jun. 1990.

Tsujimoto, Y., et al., Proc. Natl. Acad. Sci. USA, vol. 83, pp. 5214-5218, Jul. 1986.

Negrini, M., et al., Cell, vol. 49, pp. 455-463, 1987.

Reed, J., et al., Science, vol. 236, pp. 1295-1299, Jun. 5, 1987.

Orkin SH, et al., "Report and Recommendations of the Panel to Assess the NIH Investment in Research on Gene Therapy".

D. M. Hockenbery. et al. "BCL2 protein is topographically restricted in tissues characterized by apoptotic cells", Proc. Natl. Acad. Sci. USA, vol. 88, 1991, pp. 6961-6965.

B. Calabretta, "Inhibition of Protooncogene Expression and Antisense Ologodeoxynycleotides: Biological and Therapeutic Implications", Cancer Research, vol. 51, No. 17, Sep. 1, 1991, pp. 4505-4510.

* cited by examiner

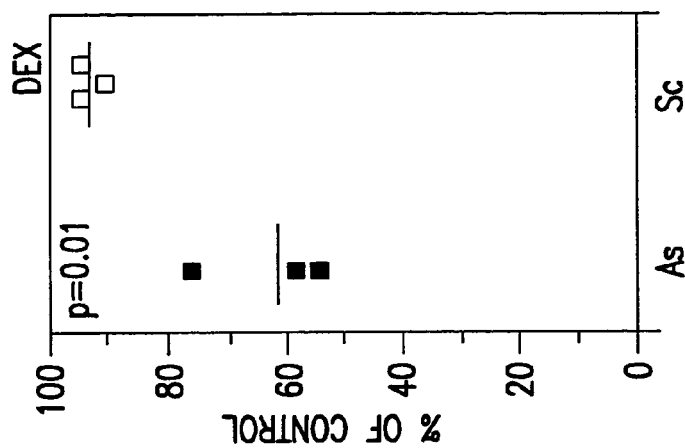
FIG.8C(3)
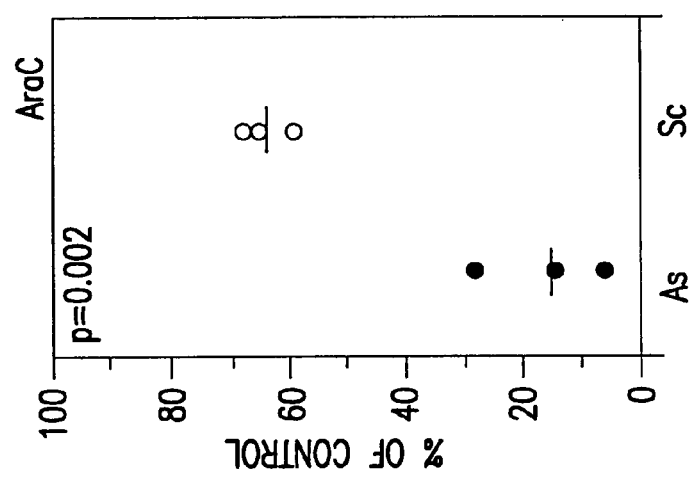
FIG.8C(2)
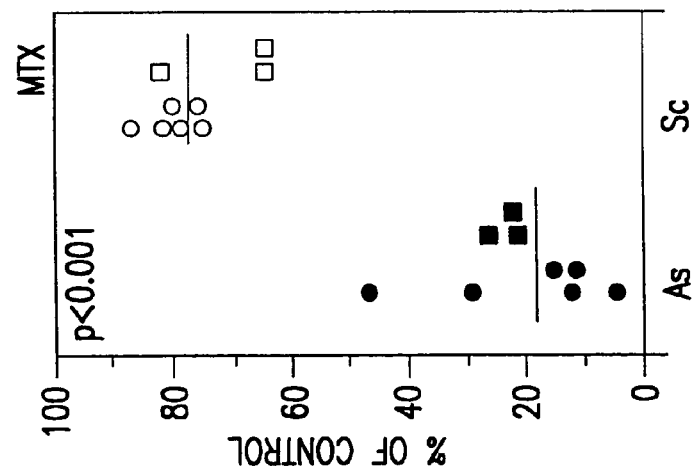
FIG.8C(1)

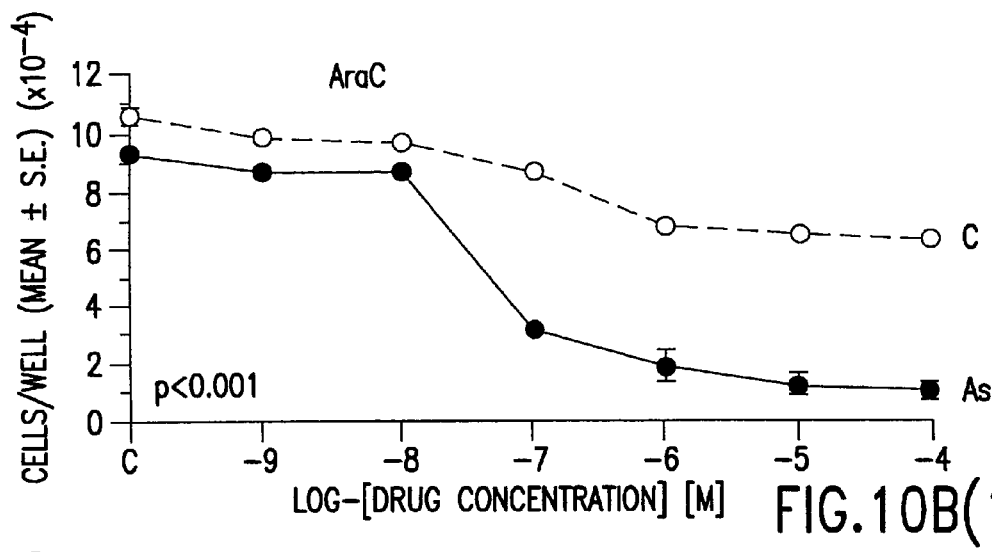
FIG.10B(1)
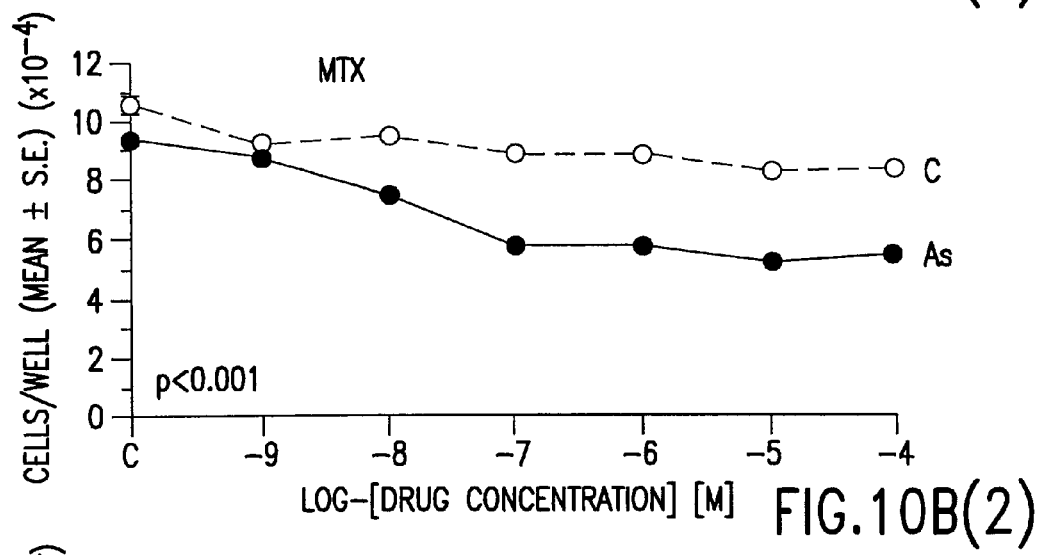
FIG.10B(2)
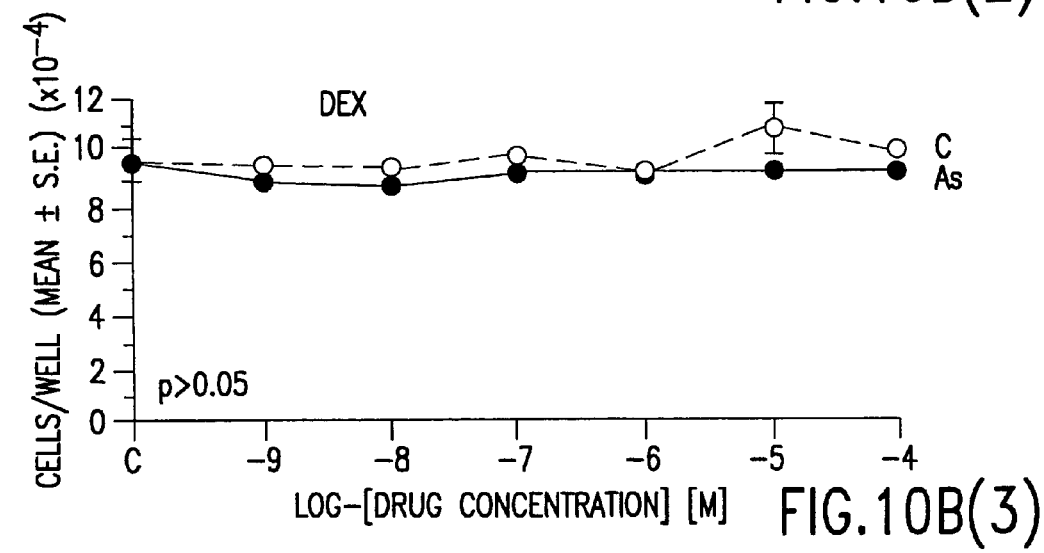
FIG.10B(3)

REGULATION OF BCL-2 GENE EXPRESSION

This application is a continuation of application Ser. No. 09/080,285, filed May 18, 1998 and issued as U.S. Pat. No. 6,040,181 on Mar. 21, 2000, which is a continuation of application Ser. No. 08/465,485, filed Jun. 5, 1995 and issued as U.S. Pat. No. 5,831,066 on Nov. 3, 1998, which is a continuation of application Ser. No. 08/124,256 filed Sep. 20, 1993, abandoned, which is a continuation-in-part of application Ser. No. 07/840,716, filed Feb. 21, 1992, abandoned, which is a continuation-in-part of application Ser. No. 07/288,692, filed Dec. 22, 1998, abandoned.

REFERENCE TO GOVERNMENT GRANTS

The research in this patent application was supported in part by National Institutes of Health grants CA 47956 and CA 60381. The United States government has certain rights in the invention.

FIELD OF THE INVENTION

The present invention relates to the field of treatments for cancer and more particularly to the field of anticode oligomer treatments for cancer.

BACKGROUND OF THE INVENTION

Current approaches to cancer treatment suffer from a lack of specificity. The majority of drugs that have been developed are natural products or derivatives that either block enzyme pathways or randomly interact with DNA. Due to low therapeutic indices, most cancer treatment drugs are accompanied by serious dose-limiting toxicities. The administration of drugs to treat cancer kills not only cancer cells but also normal non-cancerous cells. Because of these deleterious effects, treatments that are more specific for cancerous cells are needed.

It has been found that a class of genes, the oncogenes, plays a large role in the transformation and maintenance of the cancerous state and that turning off these genes, or otherwise inhibiting their effects, can return a cell to a normal phenotype. The role of oncogenes in the etiology of many human cancers has been reviewed in Bishop, "Cellular Oncogenes and Retroviruses," *Science,* 235:305–311 (1987). In many types of human tumors, including lymphomas and leukemias, the human bcl-2 gene is overexpressed, and may be associated with tumorigenicity (Tsujimoto et al. Involvement of the bcl-2 gene in human follicular lymphoma, *Science* 228:1440–1443 (1985)).

Antisense oligodeoxynucleotides are one example of a specific therapeutic tool with the potential for ablating oncogene function. These short (usually about 30 bases) single-stranded synthetic DNAs have a complementary base sequence to the target mRNA and form a hybrid duplex by hydrogen bonded base pairing. This hybridization can be expected to prevent expression of the target mRNA code into its protein product and thus preclude subsequent effects of the protein product. Because the mRNA sequence expressed by the gene is termed the sense sequence, the complementary sequence is termed the antisense sequence. Under some circumstances, inhibition of mRNA would be more efficient than inhibition of an enzyme's active site, since one mRNA molecule gives rise to multiple protein copies.

Synthetic oligodeoxynucleotides complementary to (antisense) mRNA of the c-myc oncogene have been used to specifically inhibit production of c-myc protein, thus arresting the growth of human leukemic cells in vitro, Holt et al., *Mol. Cell Biol.* 8:963–973 (1988), and Wickstrom et al., *Proc. Natl. Acad. Sci. USA,* 85:1028-1-32 (1988). Oligodeoxynucleotides have also been employed as specific inhibitors of retroviruses, including the human immunodeficiency virus (HIV-I), Zamecnik and Stephenson, *Proc. Natl. Acad. Sci. USA,* 75:280–284 (1978) and Zamecnik et al., *Proc. Natl. Acad. Sci. USA,* 83:4143–4146 (1986).

SUMMARY OF THE INVENTION

The invention provides anticode oligomers and methods for inhibiting growth of cancer cells. The growth of lymphoma or leukemia cells, which are types of lymphocytes, are inhibited by the anticode oligomers and methods of the invention. An anticode oligomer complementary to at least an effective portion of the mRNA sense strand to the human bcl-2 gene is provided and cells are then contacted with the anticode oligomer in a concentration sufficient to inhibit growth of the cells. The methods of the invention are suitable for inhibiting growth of lymphoma/leukemia cells that express the human bcl-2 gene and have a t (14; 18) chormosomal translocation as well as those that express the bcl-2 gene but do not have a t (14; 18) chromosomal translocation.

In accordance with preferred embodiments, the anticode oligomer is substantially complementary to a strategic site in the pre-mRNA sense strand or substantially complementary to the mRNA. A preferred strategic site is the translation-initiation site of the pre-mRNA coding strand. Alternative strategic sites include coding sites for splicing, transport or degradation. The subject anticode oligomer either in its "native," unmodified form—oligonucleotide—or as a derivative, is brought into contact with the target lymphoma or leukemia cells. For in vivo therapeutic use, a derivative of the "native" oligonucleotide, such as the phosphorothioate form is preferable since it is believed that these forms are more resistant to degradation, notwithstanding the fact that response time to some analogues, such as the phosphorothioate analogs, has been found to be somewhat slower than to the "native" form of the oligonucleotide.

A preferred anticode oligomer, denominated herein the TI-AS (translation initiation anticode oligomer) is an oligodeoxynucleotide which straddles the translation-initiation site of the mRNA coding strand of the human bcl-2 gene and is complementary to this region. More preferably, this nucleotide comprises a TAC portion which is complementary to the ATG inhibition sequence of the coding strand for the bcl-2 gene, and preferably further comprises flanking portions of two to about one hundred bases, more preferably from about five to about twenty bases, which are complementary to portions of the bcl-2 gene coding strand flanking said initiation sequence. The TI-AS nucleotide has been found effective at inhibiting the growth of the target cells both in the presence and absence of serum.

Alternatively, the anticode oligomer comprises an antisense nucleotide complementary to at least an effective portion of the splice donor site of the pre-mRNA coding strand for the human bcl-2 gene. More particularly, this nucleotide comprises a CA portion which is complementary to the GT splice donor of the bcl-2, and again comprises flanking portions of two to about one hundred bases, preferably from about five to about twenty bases, which are complementary to portions of the bcl-2 gene coding strand flanking said splice donor.

In yet another embodiment, the anticode oligomer is complementary to at least an effective portion of the splice acceptor region of the pre-mRNA coding strand for the human bcl-2 gene. This oligomer comprises at least a TC portion which is complementary to the AG splice acceptor of the bcl-2 gene, and again comprises flanking portions of two to about one hundred, preferably from about five to about twenty bases which are complementary to portions of the bcl-2 gene coding strand flanking said acceptor. The subject oligomer may also be selected to overlap the coding site for the 26 kDa protein, bcl-2-alpha or for the 22 kDa protein, bcl-2-beta, protein products of the bcl-2 gene. Preferably the oligomer is selected to minimize homology with anticode oligomers for pre-mRNA or mRNA coding strands for other gene sequences.

Accordingly, a primary object of the present invention is the provision of novel anticode oligomers, which are useful in inhibiting the growth of cancer cells. The present invention also includes compositions for inhibiting the growth of tumor cells, which compositions comprise the anticode oligomer of the present invention together with a pharmaceutically acceptable carrier.

A further object of the present invention is the provision of methods for inhibiting the growth of cancer cells using said anticode oligomers. As a feature of the present invention, it was discovered that average reductions of 30–40% in the relative levels of bcl-2 protein markedly enhanced the sensitivity of lymphoma cells, in particular, t(14;18)-containing lymphoma cell lines to cancer chemotherapeutic agents, including conventional anticancer drugs. Such reductions were achieved by introducing into tumor cells an anticode oligomer which binds to either pre-mRNA or mRNA expressed from the bcl-2 gene. Two methods were used in the present invention to introduce said anticode oligomers to tumor cells. One method involved contacting the tumor cells with a composition comprising the anticode oligomers. Another method involved transfecting the tumor cells with a vector encoding an antisense oligonucleotide. Introducing an anticode oligomer to tumor cells achieved a reduction of bcl-2 expression and increases the chemosensitivity of neoplastic cells to cancer chemotherapeutic agents or anticancer drugs.

Accordingly, the present invention achieved a method of killing tumor cells by introducing to tumor cells anticode oligomers which reduce bcl-2 gene expression or impair Bcl-2 protein function before contacting the cells with cancer chemotherapeutic agents. The cancer chemotherapeutic agents reduced the numbers of viable malignant cells, and the portion of tumor cells killed was greater than the portion which would have been killed by the same amount of drug in the absence of introducing the anticode oligomer oligodeoxynucleotide to the cells.

These and other objects of the present invention will become apparent from the following detailed description.

BRIEF DESCRIPTION OF THE DRAWINGS

FIG. 4 shows the degree of DNA fragmentation resulting from oligonucleotide treatment of RS11846 cells. FIG. 4 (b) shows the effect of oligonucleotides directed against the 5'-cap region of bcl-2 mRNA.

DETAILED DESCRIPTION OF THE INVENTION

Figure 1A:
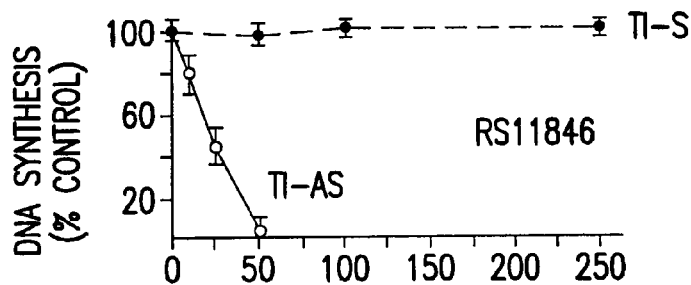
FIG. 1 shows graphs of the effects of varying concentrations of antisense oligodeoxynucleotides on inhibition of cell proliferation.
Figure 1B:
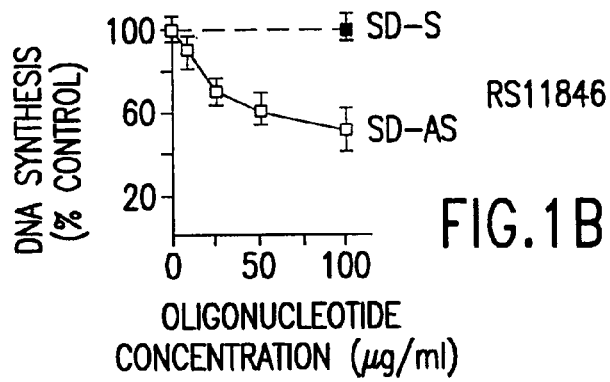
Figure 1C:
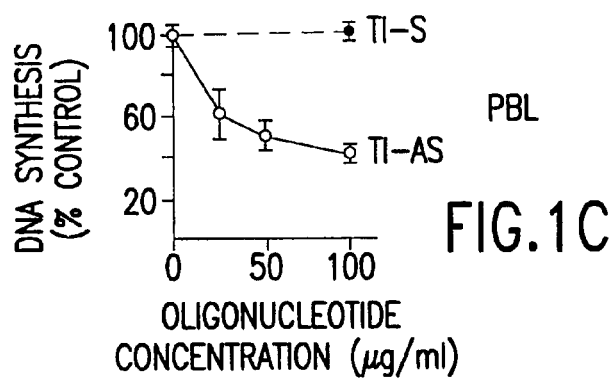
Figure 1D:
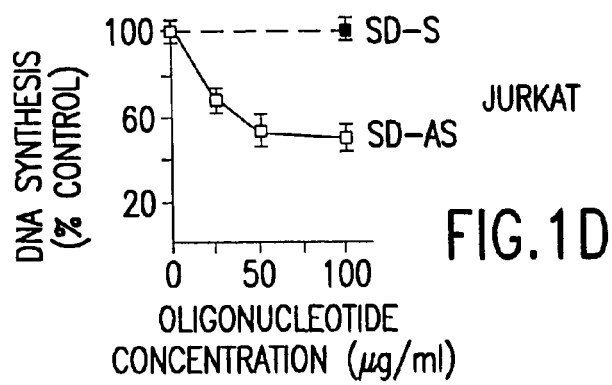

According to the invention, anticode oligomers are provided for inhibiting cancer cell growth, for increasing the sensitivity of cancer cells to cancer chemotherapeutic agents, or for inducing cancer cell death alone or in combination with any one or more cancer chemotherapeutic agents.

DEFINITIONS

As used herein, the term "anticode oligomers" means anticode oligonucleotides and analogs thereof and refers to a range of chemical species that recognize polynucleotide target sequences through hydrogen bonding interactions with the nucleotide bases of the target sequences. The target sequences may be single- or double-stranded RNA or single- or double-stranded DNA.

The anticode oligonucleotides and analogs thereof may be RNA or DNA, or analogs of RNA or DNA, commonly referred to as antisense oligomers or antisense oligonucle otides. Such RNA or DNA analogs comprise but are not limited to 2-O'-alkyl sugar modifications, methylphosphonate, phosphorothiate, phosphorodithioate, formacetal, 3'-thioformacetal, sulfone, sulfamate, and nitroxide backbone modifications, and analogs wherein the base moieties have been modified. In addition, analogs of oligomers may be polymers in which the sugar moiety has been modified or replaced by another suitable moiety, resulting in polymers which include, but are not limited to, morpholino analogs and peptide nucleic acid (PNA) analogs (Egholm, et al. Peptide Nucleic Acids (PNA)—Oligonucleotide Analogues with an Achiral Peptide Backbone, (1992)).

Anticode analogs may also be mixtures of any of the oligonucleotide analog types together or in combination with native DNA or RNA. At the same time, the oligonucleotides and analogs thereof may be used alone or in combination with one or more additional oligonucleotides or analogs thereof. The oligonucleotides may be from about 10 to about 1,000 nucleotides long. Although oligonucleotides of 10 to 100 nucleotides are useful in the invention, preferred oligonucleotides range from about 15 to about 24 bases in length.

Anticode oligonucleotides and analogs thereof also comprise conjugates of the oligonucleotides and analogs thereof. (John Goodchild, Conjugates of Oligonucleotides and Modified Oligonucleotides: A Review of Their Synthesis and Properties, *Bioconjugate Chemistry*, Volume 1 No. 3, May/June (1990)). Such conjugates having properties to improve the uptake, pharmacokinetics, and nuclease resistance of the oligonucleotide, or the ability to enhance cross-linking or cleavage of the target sequence by the oligonucleotide.

As used herein, the term "cell proliferation" refers to cell division rate/cell cycle. The term "growth," as used herein, encompasses both increased cell numbers due to faster cell division and due to slower rates of cell death.

As used herein, bcl-2 gene expression refers to bcl-2 protein production from the human bcl-2 gene; e.g. reduced bcl-2 gene expression means reduced levels of bcl-2 protein.

As used herein, "strategic sites" are defined as any site which when bound by the claimed anticode molecules or analogs thereof results in inhibiting expression of the bcl-2 gene.

As used herein, the term "sequence portion" is a portion of the nucleotide sequence of an RNA oligonucleotide. In appropriate contexts, "sequence portion" may refer to a portion of the nucleotide sequence of a DNA segment or DNA oligonucleotide.

Uncontrolled cell proliferation is a marker for a cancerous or abnormal cell type. Normal, non-cancerous cells divide regularly, at a frequency characteristic for the particular type of cell. When a cell has been transformed into a cancerous state, the cell divides and proliferates uncontrollably. Inhibition of proliferation modulates the uncontrolled division of the cell. Containment of cell division often correlates with a return to a non-cancerous state.

A human gene termed bcl-2 (B cell lymphoma/leukemia-2) is implicated in the etiology of some common lymphoid tumors, Croce et al., "Molecular Basis Of Human B and T Cell Neoplasia," in *Advance in Viral Oncology*, 7:35–51, G. Klein (ed.), New York: Raven Press, 1987. High levels of expression of the human bcl-2 gene have been found in all lymphomas with t (14; 18) chromosomal translocations including most follicular B cell lymphomas and many large cell non-Hodgkin's lymphomas. High levels of expression of the bcl-2 gene have also been found in certain leukemias that do not have a t(14; 18) chromosomal translocation, including most cases of chronic lymphocytic leukemia acute, many lymphocytic leukemias of the pre-B cell type, neuroblastomas, nasophryngeal carcinomas, and many adenocarcinomas of the prostate, breast, and colon. (Reed et al., Differential expression of bcl-2 protooncogene in neuroblastoma and other human tumor cell lines of neural origin. *Cancer Res.* 51:6529 (1991); Yunis et al. Bcl-2 and other genomic alterations in the prognosis of large-cell lymphomas. *New England J. Med.* 320:1047; Campos et al. High expression of bcl-2 protein in acute myeloid leukemia is associated with poor response to chemotherapy. *Blood* 81:3091–3096 (1993); McDonnell et al. Expression of the protooncogene bcl-2 and its association with emergence of androgen-independent prostate cancer. *Cancer Res.* 52:6940–6944 (1992); Lu, Q-L, et al. Bcl-2 protooncogene expression in Epstein Barr Virus-Associated Nasopharyngeal Carcinoma, *Int. J. Cancer* 53:29–35 (1993); Bonner et al. bcl-2 protooncogene and the gastrointestinal mucosal epithelial tumor progression model as related to proposed morphologic and molecular sequences, *Lab. Invest.* 68:43A (1993)).

While not limited to the following explanation, the present invention exploits cellular mechanisms concerned with normal cell death. Because most types of cells have a finite life span and are programmed to die, uncontrollable cell accumulation can also result because of a defect in normal cell death mechanisms rather than through an increased rate of cell division. The bcl-2 gene contributes to the pathogenesis of cancer primarily by prolonging cell survival rather than accelerating cell division.

Antisense oligomers suitable for use in the invention include nucleotide oligomers which are two to two hundred nucleotide bases long; more preferably ten to forty bases long; most preferably twenty bases long. The oligonucleotides are preferably selected from those oligonucleotides complementary to strategic sites along the pre-mRNA of bcl-2, such as the translation initiation site, donor and splicing sites, or sites for transportation or degradation.

Blocking translation at such strategic sites prevents formation of a functional bcl-2 gene product. It should be appreciated, however, that any combination or subcombination of anticode oligomers, including oligonucleotides complementary or substantially complementary to the bcl-2 pre-mRNA or mRNA that inhibit cell proliferation, is suitable for use in the invention. For example, oligodeoxynucleotides complementary to sequence portions of contiguous or non-contiguous stretches of the bcl-2 RNA may inhibit cell proliferation and would thus be suitable for use in the invention.

It should also be appreciated that anticode oligomers suitable for use in the invention may also include oligonucleotides flanking those complementary or substantially complementary to such sequence portions as the strategic or other sites along the bcl-2 mRNA. The flanking sequence portions are preferably from two to about one hundred bases, more preferably from about five to about twenty bases in length. It is also preferable that the anticode oligomers be complementary to a sequence portion of the pre-mRNA or mRNA that is not commonly found in pre-mRNA or mRNA of other genes to minimize homology of anticode oligomers for pre-mRNA or mRNA coding strands from other genes.

Preferred antisense, or complementary, oligodeoxynucleotides are listed in Table I.

TABLE I bcl-2 Oligodeoxynucleotides

| translation initiation | | | SEQ ID NO. |
|---|---|---|---|
| antisense (TI-AS) | 3' | ...CCCTTCCTACCGCGTGCGAC... 5' | 1 |
| bcl-2 splice donor antisense (SD-AS) | 5' | ...CTTTTCCTCTGGGAAGGATGGCGCACGCTGGGAGA... 3' | 2 |
| | 3' | ...CCTCCGACCCATCCACGTAG... 5' | 3 |
| bcl-2 splice acceptor antisense (SA-AS) | 5' | ...ACGGGGTAC...GGAGGCTGGGTAGGTGCATCTGGT... 3' | 4 |
| | 3' | ...GTTGACGTCCTACGGAAACA... 5' | 5 |
| bcl-2 | 5' | ...CCCCCAACTGCAGGATGCCTTTGTGGAACTGTACGG... 3' | 6 |

It will be appreciated by those skilled in the art to which this invention pertains, that anticode oligomers having a greater or lesser number of substituent nucleotides, or that extend further along the bcl-2 mRNA in either the 3' or 5' direction than the preferred embodiments, but which also inhibit cell proliferation are also within the scope of the invention.

It is preferable to use chemically modified derivatives or analogs of anticode oligomers in the performance of the invention rather than "native" or unmodified oligodeoxynucleotides. "Native" oligodeoxynucleotides can be conveniently synthesized with a DNA synthesizer using standard phosphoramidite chemistry. Suitable derivatives, and methods for preparing the derivatives, include phosphorothioate, Stein et al., Nucl. Acids Res., 16:3209–3221 (1988); methylphosphonate, Blake et al., Biochemistry 24:6132–6138 (1985) and alphadeoxynucleotides, Morvan et al., Nucl. Acids Res. 14:5019–5032 (1986), 2'-O-methyl-ribonucleosides (Monia et al. Evaluation of 2'-modified oligonucleotides containing 2' deoxy gaps as antisense inhibitors of gene expression. *J. Biol. Chem.* 268:14514–14522 (1933)), and covalently-linked derivatives such as acridine, Asseline et al., Proc. Natl Acad. Sci. *USA* 81:3297–3201 (1984); alkylated (e.g., N-2-chlorocethylamine), Knorre et al., Biochemie 67:783–789 (1985) and Vlassov et al., Nucl. Acids Res. 14:4065–4076 (1986); phenazine, Knorre et al., supra, and Vlassov et al., supra; 5-methyl-$N^4$-$N^4$-ethanocytosine, Webb et al., Nucl. Acids Res. 14:7661–7674 (1986); Fe-ethylenediamine tetraacetic acid (EDTA) and analogues, Boutorin, et al., FEBS Letters 172:43–46 (1984); 5-glycylamido-1,10-O-phenanthroline, Chi-Hong et al., Proc. Natl. Acad. Sci. *USA* 83:7147–7151 (1986); and diethylenetriaamine-pentaacetic acid (DTPA) derivatives, Chu et al., Proc. Natl. Acad. Sci. *USA* 82:963–967 (1985). All of the above publications are hereby specifically incorporated by reference as if fully set forth herein.

The anticode oligomer of the present invention can also be combined with a pharmaceutically acceptable carrier for administration to a subject or for ex-vivo administration. Examples of suitable pharmaceutical carriers are a variety of cationic lipids, including, but not limited to N-(1-(2,3-dioleyloxy)propyl)-N,N,N-trimethylammonium chloride (DOTMA) and dioleoylphosphatidylethanolamine (DOPE)]. Liposomes are also suitable carriers for the anticode oligomers of the invention.

The anticode oligomers may be administered to patients by any effective route, including intravenous, intramuscular, intrathecal, intranasal, intraperitoneal, subcutaneous injection, in situ injection and oral administration. Oral administration requires enteric coatings or protect the claimed anticode molecules and analogs thereof from degradation along the gastrointestinal tract. The anticode oligomers may be mixed with an amount of a physiologically acceptable carrier or diluent, such as a saline solution or other suitable liquid. The anticode oligomers may also be combined with liposomes or other carrier means to protect the anticode molecules or analogs thereof from degradation until they reach their targets and/or facilitate movement of the anticode molecules or analogs thereof across tissue barriers.

The anticode oligomers may also be useful for ex vivo bone marrow purging. Normally, the amounts of conventional cancer chemotherapeutic agents or drugs and irradiation that a patient can receive are limited by toxicity to the marrow, i.e., anemia (fatigue, heart failure), thrombocytopenia (bleeding), neutropenia (infection). Thus, in order to deliver sufficient concentrations of drugs and irradiation to totally eradicate the tumor, the physician would simultaneously destroy the patient's normal bone marrow cells leading to patient demise. Alternatively, large amounts of bone marrow can be surgically extracted from the patient and stored in vitro while the patient receives aggressive conventional treatment. The patient can then be rescued by reinfusion of their own bone marrow cells, but only if that marrow has been "purged" of residual malignant cells. The claimed anticode oligomers could be used to remove residual malignant cells from the bone marrow.

The anticode oligomers are administered in amounts effective to inhibit cancer or neoplastic cell growth. The actual amount of any particular anticode oligomer administered will depend on factors such as the type of cancer, the toxicity of the anticode oligomer to other cells of the body, its rate of uptake by cancer cells, and the weight and age of the individual to whom the anticode oligomer is administered. Because of inhibitors present in human serum that may interfere with the action of the anticode oligomer an effective amount of the anticode oligomer for each individual may vary. An effective dosage for the patient can be ascertained by conventional methods such as incrementally increasing the dosage of the anticode oligomer from an amount ineffective to inhibit cell proliferation to an effective amount. It is expected that concentrations presented to cancer cells in the range of about 0.001 micromolar to about 100 micromolar will be effective to inhibit cell proliferation.

The anticode oligomers are administered to the patient for at least a time sufficient to inhibit proliferation of the cancer cells. The anticode oligomers are preferably administered to patients at a frequency sufficient to maintain the level of anticode oligomers at an effective level in or around the cancer cells. To maintain an effective level, it may be necessary to administer the anticode oligomers several times a day, daily or at less frequent intervals. Anticode oligomers are administered until cancer cells can no longer be detected, or have been reduced in number such that further treatment provides no significant reduction in number, or the cells have been reduced to a number manageable by surgery or other treatments. The length of time that the anticode oligomers are administered will depend on factors such as the rate of uptake of the particular oligodeoxynucleotide by cancer cells and time needed for the cells to respond to the oligodeoxynucleotide. In vitro, maximal inhibition of neoplastic cell growth by "native," unmodified anticode oligomers occurred two days after initiation of cultures, whereas phosphorothioate oligodeoxynucleotides required 4 to 7 days to achieve maximal inhibition. In vivo, the time necessary for maximal inhibition of cell proliferation may be shorter or longer.

The anticode oligomers of the invention may be administered to patients as a combination of two or more different anticode oligomer oligodeoxynucleotide sequences or as a single type of sequence. For instance, TI-AS and SD-AS could be administered to a patient or TI-AS alone.

It is also believed that the anticode oligomers of the invention may be useful in the treatment of autoimmune diseases. Autoimmune diseases are those diseases in which the body's immune system has malfunctioned in some way. Administration of the anticode oligomers of the invention to a person having an autoimmune disease should inhibit proliferation of bcl-2 overexpressing lymphocytes, which would in turn reduce the symptoms of the autoimmune disease. For use in treating autoimmune diseases, the anticode oligomers would be administered as described herein.

EXAMPLES

General Methods

The Examples below use the following protocols:

A. Cells and Cell Cultures. Human leukemic cells lines used for these studies were RS11846 follicular lymphoma cells, 697 pre-B cell acute lymphocytic leukemic cells, and JURAT T cell acute lymphocytic leukemic cells as described in Tsujimoto et al., *Proc. Natl. Acad. Sci. USA*, 83:5214–5218 (1986) and Weiss et al., *Proc. Natl. Acad. Sci. USA*, 138:2169–2174 (1987). Human peripheral blood lymphocytes (PBL) were isolated from fresh whole blood as described in Reed et al., *J. Immunol.*, 134:314–319 (1985). All lymphoid cells were cultured at $5\times10^5$ cells/ml in RPMI medium supplemented with 1 mM glutamine, antibiotics, and either 5–10% (v:v) fetal bovine serum (FBS), 5–10% (v:v) calf serum (CS) (both from Hyclone Laboratories), or 1% (v:v) HLI concentrated supplement (Ventrex Laboratories) for serum-free cultures. Murine fibroblast cell lines were added at $10^3$ cells/cm$^2$ in DMEM medium containing glutamine, antibiotics and 5–10% (v:v) FCS. Fibroblast cell lines were NIH 3T3 cells, 3T3-B-alpha-S cells, and 3T3-B-alpha-AS cells. These latter two cell lines are NIH 3T3 cells that express high levels of a human bcl-2-alpha cDNA in either the sense or antisense orientation, respectively, by virtue of stable transfection with expression vectors constructs.

B. Measurement of Cellular Growth. Growth of cell lines cultured in the presence or absence of anticode oligomers was measured by two methods: cell counts using a hemocytometer; and DNA synthesis by assaying [$^3$H]-thymidine incorporation essentially as described in Reed et al., *J. Immunol.*, 134:314–319 (1985). Briefly, cells were cultured in 96-well flat-bottomed microtiter plates (Falcon) at 0.2 ml/well. At appropriate times, cells were resuspended, 25 μl removed from cultures for cell counting, and this volume replaced with 25 μl of 20 UCi/ml [$^3$H]-thymidine (specific activity 6.7 Ci/mmole) (New England Nuclear). Microtiter cultures were then returned to 37° C. and 95% air: 5% CO$_2$ atmosphere for 8 hours before lysing cells an glass filters and determining relative levels of [$^3$H]-thymidine incorporation into DNA by scintillation counting. Cell counts were performed in the presence of trypan blue dye to determine the concentration of viable cells in duplicate microcultures.

MTT [3-(4,5-dimethylthiazol-2-yl)-2,5-diphenyl tetrazolium bromide)] dye reduction assays were performed by the method of Tada, et al. J. Immunol. Methods 93, 157, (1986), and confirmed to be within the linear range of the assay under the conditions described here. The number of viable cells per well was extrapolated from standard curves that were included with each assay and that consisted of serial two-fold dilutions of exponentially growing SU-DHL-4 cells in HL-1 medium, beginning with $10^6$ cells/ml (0.2 ml/well). Samples were assayed in triplicate and the $OD600_{nm}$ for a media/reagent blank was subtracted from all values prior to calculations.

C. RNA Blot Analysis. Total cellular RNA was isolated by a quanidinium isothiocyanate/phenol procedure as described in Chomczynski et al., *Analyt. Biochem.*, 162:156–139 (1987). The polyadehylated fraction was purified by oligodeoxythymidine-cellulose chromatography as described in Aviv et al., *Proc. Natl. Acad. Sci. USA*, 69:1408–1412 (1972). Approximately 5 μg aliquots of mRNA were size-fractionated in 0.8% agarose/6% formaldehyde gels and transferred to nylon membranes. Blots were prehybridized, hybridized, and washed exactly as described in Reed et al., *Mol. Cell. Biol.*, 5:3361–3366 (1985), using either a $^{32}$P-cDNA for human bcl-2, as described in Tsujimoto et al., *Proc. Natl. Acad. Sci. USA*, 83:5214–5218 (1986), or a murine bcl-2 probe, pMBCL5.4 as described in Negrini et al., *Cell*, 49:455–463 (1987). Blots were exposed to Kodak XAR film with intensifying screens at −70° C. for 1–10 days. Eluting $^{32}$P-bcl-2 probes from membranes and rehybridizing with a $^{32}$P probe for mouse beta-2-microglobulin verified nearly equivalent amounts of mRNA for all samples on blots.

Example 1

Preparation of Anticode Oligomers

Normal and phosphorothioate oligodeoxynucleotides were synthesized using an Applied Biosystems 380B DNA synthesizer, and purified by HPLC reverse-phase chromatography (PRP-1 column) as described in Stein et al., *Nucl. Acids Res.*, 16:3209–3221 (1988) which is specifically incorporated as if fully set forth herein. In some cases it was necessary to further purify oligodeoxynucleotides by C18-Sep-Pak chromatography (Waters Associates, Millipore, Inc.), as described previously in Kern et al., *J. Clin. Invest.*, 81:237–244 (1988), to eliminate nonspecific cytotoxic activity. Oligodeoxynucleotides eluted in 30% acetonitrile were evaporated to dryness, resuspended at 1–2 mM in sterile Dulbecco's phosphate-buffered saline or Hanks' buffered salt solution (both from Gibco), and stored at −80° C. in small aliquots.

Table I shows the oligodeoxynucleotide synthesized and their relation to the sense-strand of the human bcl-2 gene.

Portions of the sequence of the coding strand of the human bcl-2 gene are shown, including the translation initiation site (top), splice donor site (middle), splice acceptor region (bottom), and empirically selected sites within the 5' untranslated portion of the bcl-2 pre-mRNA. The ATG initiation codon, GT splice donor, and AG splice acceptor consensus sequences are in boxes.

The sequences of the oligodeoxynucleotides synthesized for these investigations are presented, and their relation to human bcl-2 mRNA is indicated. The TI-AS oligodeoxynucleotide is antisense at the translation initiation site and TI-S is its complementary sense version. SD-AS and SD-S are oligodeoxynucleotides having antisense and sense orientations, respectively, relative to the splice donor region.

The oligodeoxynucleotide TI-AS straddles the predicted translation-initiation site of bcl-2 mRNAs and is complementary (antisense) to this region. As a control, the sense version of this 20 bp oligodeoxynucleotide, TI-S, was also synthesized.

In an effort, to specifically block splicing of bcl-2 mRNAs, a 20 bp antisense oligodeoxynucleotide, SD-AS, was synthesized that overlaps the splice donor site in bcl-2 primary transcripts. In addition, a complementary sense oligodeoxynucleotide, SD-S, was prepared as depicted in Table I. The human bcl-2 gene gives rise to several transcripts through alternative splice site selections, see Tsujimoto et al., *Proc. Natl. Acad. Sci. USA*, 83:5214–5218 (1986). The preponderance of these transcripts depend upon splicing and encode a 26 kDa protein, bcl-2-alpha. One minor transcript, however, does not undergo a splice and consequently encodes a 22 kDa protein bcl-2-beta. The SD-AS oligodeoxynucleotide can thus potentially block maturation of most but not all bcl-2 transcripts.

Example 2

Treatment of Serum for In Vitro Investigations of Antisense Normal Oligodeoxynucleotides Because normal oligodeoxynucleotides are sensitive to degradation by nucleases present in serum, the efficacy of the TI-AS oligodeoxynucleotide in fetal bovine serum (FBS) heated for 30 minutes at 56° C. (the usual procedure for inactivating serum complement) was contrasted with the efficacy of TI-AS in FBS heated for 1 hour at 68° C., a temperature sufficient for irreversible inactivation of many nucleases. The RS11846 follicular lymphoma cell line was used. RS11846 cells contain a t (14; 18) chromosomal translocation that deregulates bcl-2 expression, resulting in the accumulation of high levels of bcl-2 mRNAs, Tsujimoto et al., *Proc. Natl. Acad. Sci. USA*, 83:5214–5218 (1986).

RS11846 follicular lymphoma cells were cultured in medium containing 5% (vol:vol) fetal bovine serum (FBS) that had been heated at 56° C. for 0.5 hours or at 68° C. for 1 hour. TI-AS normal oligodeoxynucleotide was added at the initiation of culture, and the density of viable cells determined two days later.

The TI-AS normal oligodeoxynucleotide was more effective in 68° C.-treated serum at suppressing the growth in culture of these lymphoma cells. In all subsequent experiments, sera heated at 68° C. for 1 hour prior to use were used in cultures. This treatment did not impair the growth-suppressing capacity of the sera.

Example 3

Specific Inhibition of Lymphoid Cell Growth by Antisense Normal Oligodeoxynucleotides Antisense normal oligodeoxynucleotides directed against the translation initiation site (TI-AS) and the splice donor site (SD-AS) of bcl-2 transcripts were tested for their ability to suppress the proliferation of normal and neoplastic lymphoid cells.

RS11846 follicular lymphoma cells, JUKRAT T cell leukemia cells, and freshly isolated peripheral blood lymphocytes were cultured in medium containing 10% (vol:vol) FBS that had been heated at 68° C. for one hour. various concentrations of normal oligodeoxynucleotides were added at the initiation of culture, including: TI-AS, TI-S, SD-AS, and SD-S. Relative DNA synthesis was measured in cultures after 2–3 days by [$^3$H]-thymidine incorporation. Data were calculated as a percentage of control cultures containing volumes of PB or HBSS equivalent to oligodeoxynucleotide-treated cultures, and represent the mean (± standard deviation) of duplicate cultures.

Similar data were obtained by measuring cell counts, excluding cold thymidine inhibition as an explanation for the suppression of DNA synthesis observed in cultures treated with antisense oligodeoxynucleotides.

As shown in FIG. 1, both the TI-AS and SD-AS oligodeoxynucleotides inhibited the growth of RS11846 cells in a concentration-dependent manner. The SD-AS oligonucleotide was less effective in inhibiting cell growth than the TI-AS oligodeoxynucleotide. In contrast to these antisense oligodeoxynucleotides, sense oligodeoxynucleotides (TI-S and SD-S) were not inhibitory even at concentrations of up to 250 μG/ml. Moreover, non-sense oligodeoxynucleotides (i.e., those having the same base composition as the antisense oligodeoxynucleotides but with scrambled sequences) also failed to suppress the proliferation of RS11846 cells. The data thus indicate that antisense oligodeoxynucleotides can specifically block the proliferation of these tumor cells. Several other leukemic cell lines that express the bcl-2 gene were also tested for inhibition of their proliferation by TI-AS and SD-AS oligonucleotides. As with the JURKAT T cell acute lymphocytic leukemic cells, in every case a specific and concentration-dependent decrease in the growth of these human leukemic cells in cultures containing antisense oligodeoxynucleotides was observed.

It has been demonstrated that bcl-2 expression is transiently induced in normal human peripheral blood lymphocytes (PBL) when these cells are stimulated to proliferate, suggesting that this gene may play a role in the regulation of normal lymphocyte growth, Reed et al., *Science* 236:1295–1297 (1987). The capacity of antisense oligodeoxynucleotides to impair the growth of PBL cultured with a monoclonal antibody, OKT3 (Van den Elsen et al., *Nature* 312:413–418 (1984)), that stimulates their proliferation was therefore tested. PBL were stimulated with 50 μl of purified OKT3 monoclonal antibody. As shown in FIG. 1, the TI-AS oligodeoxynucleotide specifically suppressed the proliferation of PBL in a concentration-dependent manner. These antisense normal oligodeoxynucleotides thus suppressed the growth in culture of leukemic cells that constitutively express the bcl-2 gene and of normal lymphocytes where in bcl-2 expression is inducible.

Example 4

Time-Course of Inhibition by Antisense Normal Oligodeoxynucleotides

The kinetics of inhibition by antisense oligodeoxynucleotides was examined in cultures of RS11846 follicular lymphoma cells and of 697 pre-B cell acute lymphocytic leukemic cells. Both of these neoplastic B cell lines transcribe and accumulate bcl-2 mRNAs at high levels, Tsujimoto et al., *Proc. Natl. Acad. Sci. USA*, 83:5214–5218 (1986).

RS11846 follicular lymphoma and 697 pre-B cell leukemia cells were cultured in medium containing 10% (vol:vol) 68° C.-treated FBS and normal oligodeoxynucleotides. Cells were cultured with 50 μg/ml TI-AS, 100 μg/ml SD-AS, 50 μg/ml TI-S (RS11846 cells) or 100 μg/ml SO-S (697 cells), or PBS as a control. DNA synthesis (kcpm/$10^5$ viable cells) and cell densities ($10^5$ viable cells/ml) were measured at various times after initiation of cultures.

Antisense normal oligodeoxynucleotides markedly inhibited DNA synthesis measured in cultures of these cells within 24 hours. Diminished cell densities were readily apparent in these cultures within 2 days. Antisense normal oligodeoxynucleotides thus rapidly inhibited and in vitro growth of leukemic cells. The action of antisense oligodeoxynucleotides was specific, since sense oligodeoxynucleotides did not impair proliferation in these cultures. Though cell viabilities often declined during the later days of culture no increase in cell death was seen during the first 1–2 days of culture with antisense oligodeoxynucleotides, suggesting a non-cytotoxic mechanism.

Example 5

Comparison of Different Serum Preparations

Inhibition of proliferation of leukemic cells with antisense oligodeoxynucleotides can vary greatly depending on the lot of serum used in cultures.

To determine the effects of serum of inhibition or proliferation, relative levels of DNA synthesis were measured in cultures of 697 pre-B cell leukemia cells 2 days after addition of 200 μM TI-AS normal oligodeoxynucleotide. Cells were cultured in medium supplemented with 1% (vol:vol) HL1-concentrate (serum-free condition), 5% (vol:vol) of two different lots of calf serum (CS1 and CS2), or 5% (vol:vol) of two different lots of fetal bovine serum (FBS1 and FBS2). All sera were heated at 68° C. for 1 hour prior to use in cultures.

The normal TI-AS oligodeoxynucleotide markedly inhibited DNA synthesis (92%) and cellular proliferation in serum-free cultures (HL1) of 697 cells. This antisense oligodeoxynucleotide was equally effective (94%) in cultures containing 5% (v:v) of one of the lots of fetal bovine serum (FBS2). In contrast, inhibition was significantly reduced in cultures containing other serum preparations (CS1, CS2, FBS1). It has been generally observed that antisense normal oligodeoxynucleotides are less effective in cultures supplemented with calf serum (CS) than in those containing fetal bovine serum (FBS).

Example 6

Concentration Dependence of Inhibition by Antisense Normal Oligodeoxynucleotides in Serum-Free Cultures 697 pre-B cell leukemia cells were cultured in medium with either 1% (vol:vol) HL1-concentrate (serum-free conditions or 5% (vol:vol) 68° C.-treated FBS2). Relative levels of DNA synthesis and cellular densities measured after 2 days in cultures containing various concentrations of normal TI-AS oligodeoxynucleotide.

The TI-AS oligodeoxynucleotide was inhibitory at lower concentrations when used in serum-free cultures. At 100 μM, for instance, no inhibition of cellular proliferation was seen in FBS2-containing cultures, whereas cell counts were reduced by approximately 75% in serum-free cultures. At higher concentrations of antisense oligodeoxynucleotides (200–250 μM), however, inhibition of 697 cellular proliferation was comparable in both types of cultures. The increased efficacy of normal oligodeoxynucleotides in serum-free cultures was specific, since the sense oligonucleotide (TI-S) was not inhibitory at the same concentrations.

Example 7

Antisense Phosphorothioate Oligodeoxynucleotides: Time Course of Inhibition To contrast the efficacy of phosphorothioate oligodeoxynucleotides with that of normal oligodeoxynucleotides with regard to inhibition of human leukemic cell growth, phosphorothioate oligodeoxynucleotides were cultured with 697 pre-B cell leukemia cells and the effects on inhibition were measured. 697 pre-B cell leukemia cells were cultured in serum-free medium for various times before measuring DNA synthesis (kcpm) and cell densities ($10^6$ cells/ml). Cells were seeded at an initial density cf either $0.2 \times 10^5$ cells/ml or $0.5 \times 10^5$ cells/ml. Culture conditions were 25 μM TI-AS phosphorathioate, 25 μM TI-S phosphorothioate, and control cultures treated with HBSS.

To avoid experimental variation due to differences among lots of sera, 697 leukemic cells were cultured in serum-free conditions. When cultured at an initial seeding density of $0.5 \times 10^6$ cells/ml, 697 cells achieved maximal DNA synthesis and cellular densities at 4–5 days. Addition of 25 μM sense phosphorothioate oligodeoxynucleotide (TI-S) at the initiation of these cultures had little effect on 697 cell growth. In replicate cultures containing 25 μM antisense phosphorothioate (TI-AS), however, some diminution in DNA synthesis was evident within 2 days and was maximal at 4–5 days. Maximal inhibition of 697 cell growth, as determined by cell counts, was seen at 6 days after initiation of cultures.

When 697 cells were initially seeded at $0.2 \times 10^6$ cells/ml, the antisense phosphorothioate oligodeoxynucleotide, TI-AS, resulted in only slight inhibition at 2 days, attaining maximal suppression of DNA synthesis in these cultures at day 7. As with normal oligodeoxynucleotides, this inhibition by phosphorothioate oligodeoxynucleotides appeared to be mediated through non-cytotoxic mechanisms, since cellular viabilities did not decline until late in the course of culture. Compared with normal antisense oligodeoxynucleotides, therefore, phosphorothioate oligodeoxynucleotides had a slower onset of action.

Example 8

Concentration Dependence of Inhibition by Antisense bcl-2 Phosphorothioate Oligodeoxynucleotides The concentration descendence of inhibition by phosphorothioate and normal TI-AS oligodeoxynucleotides in cultures of 697 cells in serum-free medium was compared as follows.

697 cells were cultured in serum-free medium for either 3 days (normal oligodeoxynucleotides) or 4 days (phosphorothioate oligodeoxynucleotides) prior to measuring cell densities and levels of DNA synthesis. Oligodeoxynucleotide additions to cultures included TI-AS phosphorothioate, TI-S phosphorothioate, TI-AS normal, and TI-S normal.

Figure 2A:
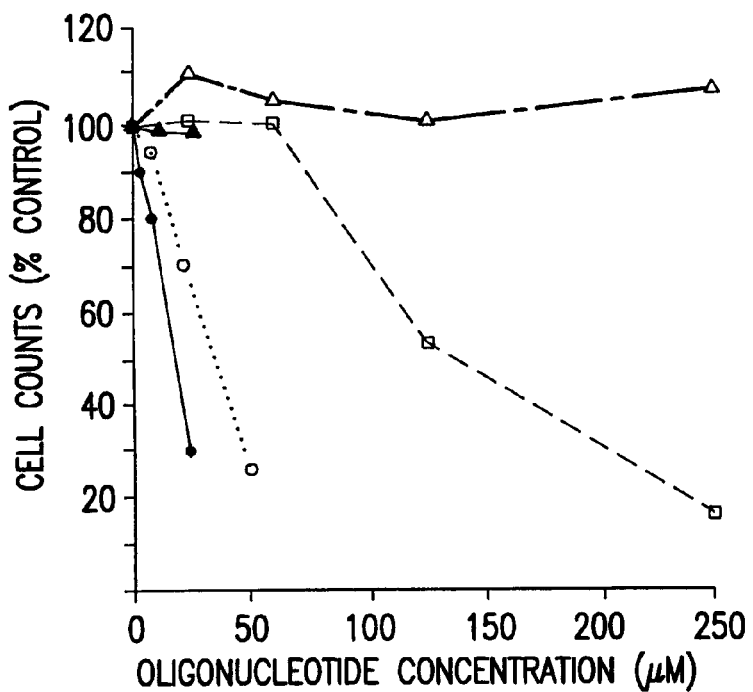
FIG. 2 shows graphs of the concentration dependence of inhibition of cell proliferation by antisense normal and phopshorothioate oligodeoxynucleotides. Oligonucleotide additions to cultures included TI-AS phosphorothioate (○ and ●; two separate experiments), TI-S phosphorothioate (▲), TI-AS normal (□), and TI-S normal (△).
Figure 2B:
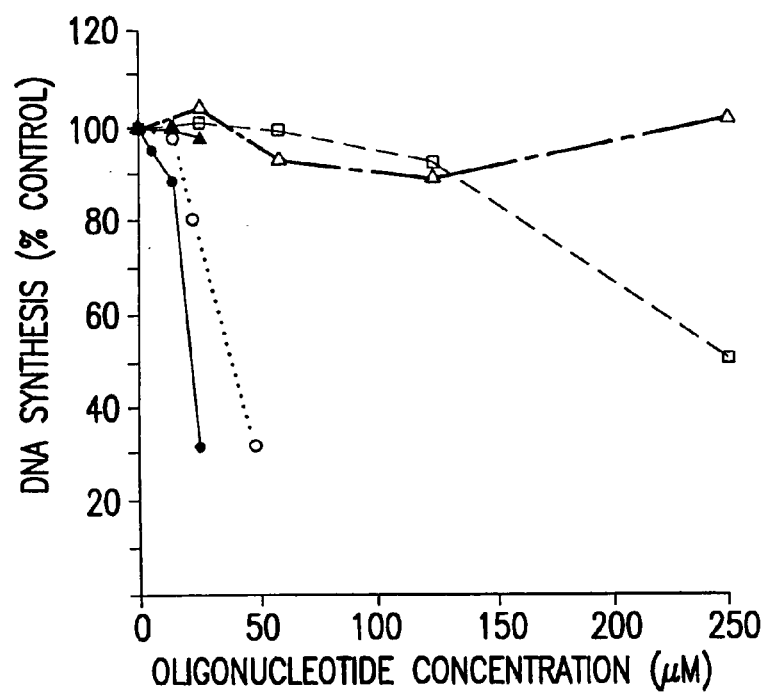

As shown in FIG. 2, the TI-AS phosphorothioate oligodeoxynucleotides markedly inhibited the proliferation of 697 cells at 25–50 µM. In contrast, normal TI-AS oligodeoxynucleotides required concentrations 5- to 10-fold higher (approximately 250 µM) to cause a comparable suppression of 697 cellular proliferation. Suppression by the antisense phosphorothioate oligodeoxynucleotide TI-AS was specific over this concentration range, since its complementary sense oligodeoxynucleotide (TI-S) produced little inhibition of 697 cell growth in replicate cultures (see FIG. 2).

Example 9

Influence of Serum Preparation on Inhibition by Antisense Phosphorothioate Oligodeoxynucleotides To further define the effects of serum preparation of the inhibitory activity of phosphorothioate oligodeoxynucleotides, FBS that had been heated to 56° C. for 30 minutes, 68° C. for 1 hour, or not heated prior to addition to cultures was added to cultures of RS11846 lymphoma cells.

RS11846 cells were cultured in medium containing 1% (vol:vol) HL1-concentrate or 5% (vol:vol) FBS that had been heated at 56° C. for 0.5 hour, 68° C. for 1 hour, or that had not been heated. Cell counts were calculated as a percentage relative to control cultures treated with equivalent concentrations of TI-S phosphorothioate oligodeoxynucleotide, and represent the mean percentage (standard deviation was less than 10% for all values) for duplicate cultures counted on days 4 and 5.

The TI-AS phosphorothioate oligodeoxynucleotide completely inhibited the growth of RS11846 cells at 25 µM, with an estimated half-maximal inhibitory concentration of approximately 11 µM. In contrast, this phosphorothioate oligodeoxynucleotide was considerably less effective in cultures containing 5% (v:v) FBS. Furthermore, heating FBS prior to adding it to cultures did not significantly improve the ability of the TI-AS phosphorothioate oligodeoxynucleotide to suppress the growth of RS11846 lymphoma cells. At an oligodeoxynucleotide concentration of 50 µM, inhibition of proliferation of RS11846 cells never exceeded 48% serum-containing cultures, regardless of the heating procedure used.

Example 10

Influence of Dialysis of Serum on Inhibition by Normal and Phosphorothioate Antisense Oligodeoxynucleotides To further characterize the nature of the interfering substances in serum, experiments were performed wherein 68° C.-heated serum was extensively dialyzed (molecular weight cutoff=3500) prior to being added to cultures of 697 leukemic cells. Experiments were conducted with 12.5 µM TI-AS phosphorothioate oligodeoxynucleotide and 200 µM of the normal oxygen-based TI-AS oligodeoxyneucleotide.

697 cells were cultured in medium containing 1% (vol:vol) HL1-concentrate (A) or 5% (vol:vol) of three different lots of 68° C.-treated FBS (B,C,D). Each serum preparation was contrasted before (ND) and after (D) extensive dialysis. TI-AS (+) and TI-S (−) oligodeoxynucleotides were added to replicate cultures at 200 µM for normal oxygen-based oligodeoxynucleotides (OXY) and at 12.5 µM for phosphorothioate oligodeoxynucleotides (PT). Relative levels of DNA synthesis (kcpm) were measured after 2 or 4 days of culture for normal and phosphorothioate oligodeoxynucleotides, respectively.

For the three different lots of FBS tested, two exhibited little change after dialysis in cultures containing either normal or phosphorothioate oligodeoxynucleotides. One lot of FBS, however, appeared to interfere less with the inhibiting activities of these antisense oligodeoxynucleotides after dialysis.

Example 11

Experiments with Stably Transfected NIH 3T3 Cells

Though the antisense oligodeoxynucleotides described herein were designed to block bcl-2 mRNA translation (TI-AS) and splicing (SD-AS), the molecular mechanisms of their actions are not yet known. To determine the effect of formation of oligodeoxynucleotide-RNA hybrids within cells upon inhibition of cellular growth, irrespective of the nucleotide sequence, cells transformed to express human bcl-2 cDNA transcripts were cultured with normal oligodeoxynucleotides.

200 µM of normal TI-AS and TI-S oligodeoxynucleotides were added to cultures of typical NIH 3T3 cells and to cultures of these cells that had been stably transfected with expression constructs that produce high levels of human bcl-2 cDNA transcripts for either the usual sense (3T3-alpha-S cells) or the antisense (3T3-alpha-AS cells) strand.

For RNA blot analyses, polyadenylated mRNA was purified from normal NIH 3T3 cells and from cells stably transfected with expression constructs that produce either sense (3T3-alpha-S) or antisense (3T3-alpha-AS) recombinant bcl-2 alpha mRNA, according to the method of 13. Approximately 5 µg of mRNA was subjected to RNA blot analysis, essentially as described in (16), using $^{32}$P-labeled hybridization probes derived from either human or murine bcl-2 sequences.

An autoradiogram resulting from a one-day exposure of a blot containing RNAs from normal 3T3 cells, 3T3-alpha-AS cells, and 3T3-alpha-S cells showed high relative levels of recombinant 2.4 and 1.4 kbp bcl-2 transcripts produced from the bcl-2 expression constructs that were transfected into 3T3-alpha-AS and 3T3-alpha-S cells.

A 10-day exposure of a blot containing RNA from normal 3T3 cells that were either proliferating or quiescent at the time of harvesting RNA showed low but detectable levels of normal 7.5 and 2.4 kbp murine bcl-2 transcripts present in proliferating 3T3 cells.

TI-AS oligodeoxynucleotide specifically suppressed DNA synthesis and cellular replication in cultures of normal NIH 3T3 cells, consistent with findings by others that fibroblasts do contain bcl-2 transcripts, albeit at low levels. The TI-AS oligodeoxynucleotide disclosed herein is complementary to the mouse bcl-2 sequence in 18 of its 20 bases (17), accounting for its ability to suppress the growth of murine NIH 3T3 cells.

NIH 3T3 cells, 3T3-alpha-AS cells, and 3T3-alpha-S cells were cultured in medium containing 5% (vol:vol) 68° C.-treated serum and either HBSS, 200 µM TI-S normal oligodeoxynucleotide, or 200 µM TI-AS normal oligodeoxynucleotide. Relative levels of DNA synthesis (kcpm) were measured in cultures after 3 days and reflect a 16 hour incubation with 0.5 µci/well of [$^3$H]-thymidine. Cell densities, estimated by phase microscopy, were consistent with the measured DNA synthesis in cultures. The percentage of inhibition of DNA synthesis in cultures containing TI-AS oligodeoxynucleotides was calculated relative to control cultures containing HBSS.

As with normal NIH 3T3 cells, culturing 3T3-alpha-S cells (producing human bcl-2-alpha sense transcripts) with TI-AS and TI-S oligodeoxynucleotides demonstrated specific suppression, since the sense oligodeoxynucleotide TI-S was not inhibitory. The level of inhibition of cellular proliferation by the antisense oligodeoxynucleotide, however, was not as great in 3T3-alpha-S cells, as might be expected, since these cells contain more bcl-2 mRNA.

Adding TI-S oligodeoxynucleotide to cultures of 3T3-alpha-AS cells (produce antisense bcl-2 transcripts) ruled out inhibition of cellular growth through a nonspecific mechanism involving oligodeoxynucleotide-RNA hybrid formation. The TI-S oligodeoxynucleotide caused little suppression of 3T3-alpha-AS cells proliferation, whereas the TI-AS oligodeoxynucleotide was markedly inhibitory in these cells. Similar data were obtained with TI-AS and TI-S phosphorothioate oligodeoxynucleotides.

Example 12

Measurements of DNA Fragmentation as an Indicator of bcl-2 Antisense Oligodeoxynucleotide-Mediated Programmed Cell Death in Human Lymphoma Cells Oligonucleotides having the sequences shown in Table 2 were tested for the ability to induce programmed cell death (DNA fragmentation) in the human t(14:18)-containing human lymphoma cell line RS11846. The oligonucleotides were all phosphodiester, and were targeted against the translation initiation site or the 5'-cap region of bcl-2 pre-mRNAs. Control oligodeoxynucleotides included at bcl-2 sense version (TI-S) or TI-AS (having SEQ ID NO:7) and a scrambled version of TI-AS that has the same base composition, but with jumbled nucleotide order.

TABLE 2

| SEQUENCE | SEQ ID NO: |
|---|---|
| CGCGTGCGAC CCTCTTG | 8 |
| TACCGCGTGC GACCCTC | 9 |
| CCTTCCTACC GCGTGCG | 11 |
| GACCCTTCCT ACCGCGT | 12 |
| GGAGACCCTT CCTACCG | 13 |
| GCGGCGGCAG CGCGG | 14 |
| CGGCGGGGCG ACGGA | 15 |
| CGGGAGCGCG GCGGGC | 16 |

RS11846 cells were adapted to grow in HL1 media with 1% FCS and their DNA metabolically labeled by addition of $^{125}$I-deoxyuridine to cultures for three hour. Labeled cells were then washed thoroughly and cultured for two days in the presence or various oligonucleotides at 50 µM. Cells were then recovered from 200 µL cultures by centrifugation, and lysed in a hypotonic buffer containing 10 mM EDTA and 14 Triton X100. After centrifugation at 16,000×g to pellet unfragmented genomic DNA, the supernatant fraction containing fragmented DNA was extracted with phenol/chloroform and ethanol precipitated. This DNA was then subjected to gel electrophoresis in 1.5% agaorse gel and transfected to nylon membranes for autoradiography.

Figure 3:
FIG. 3 shows the result of gel electrophoresis of six antisense oligonucleotides targeted against the translation initiation site of bcl-2 mRNA.
Figures 4A, 4B:
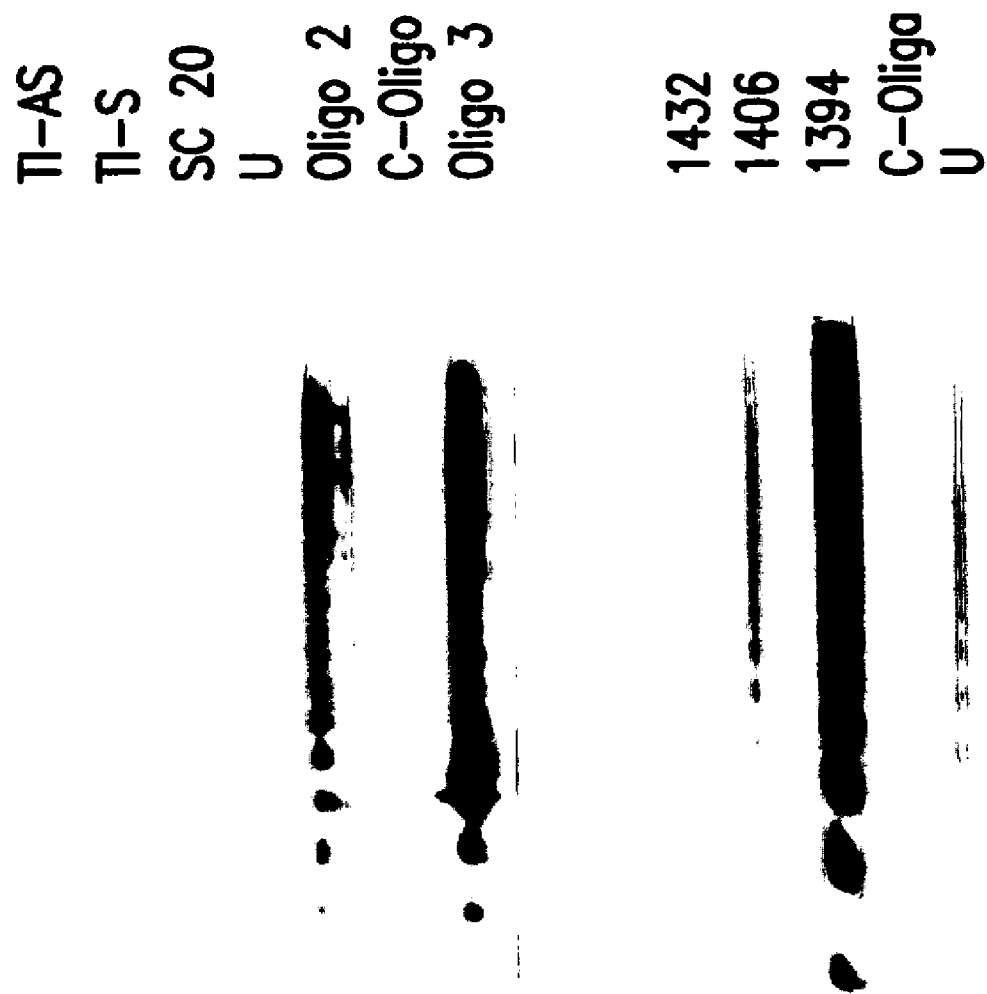
FIG. 4(a) shows the effect of oligonucleotides targeted against the translation initiation site.

The results of two experiments are shown in FIGS. 3 and 4. The six bcl-2 antisense oligonucleotides targeted in the vicinity of the ATG site of translation initiation in bcl-2 mRNAs were tested. "C-Oligo-2" refers to an oligonucleotide with 4 purposeful mismatches. "U" indicates untreated control cells. FIG. 4 shows the results for the oligonucleotides shown in FIG. 3. "Sc20" refers to a 20 mer with the same base composition as TI-AS, but with scrambled sequence. FIG. 4(b) shows the results for three oligonucleotides targeted against the 5'-cap of bcl-2 mRNAs. The numbers refer to the distance of these oligomers from the ATG-translation initiation site.

The presence of a ladder of DNA fragments (unit size of approximately 200 bp) is indicative of programmed cell death. At 50 µM, TI-AS caused little DNA fragmentation, whereas the oligonucleotides having SEQ ID NO: 9 and SEQ ID NO: 10, and one of the 5'-cap oligonucleotides (SEQ ID NO: 14) led to pronounced DNA fragmentation.

Example 13

Figure 5:
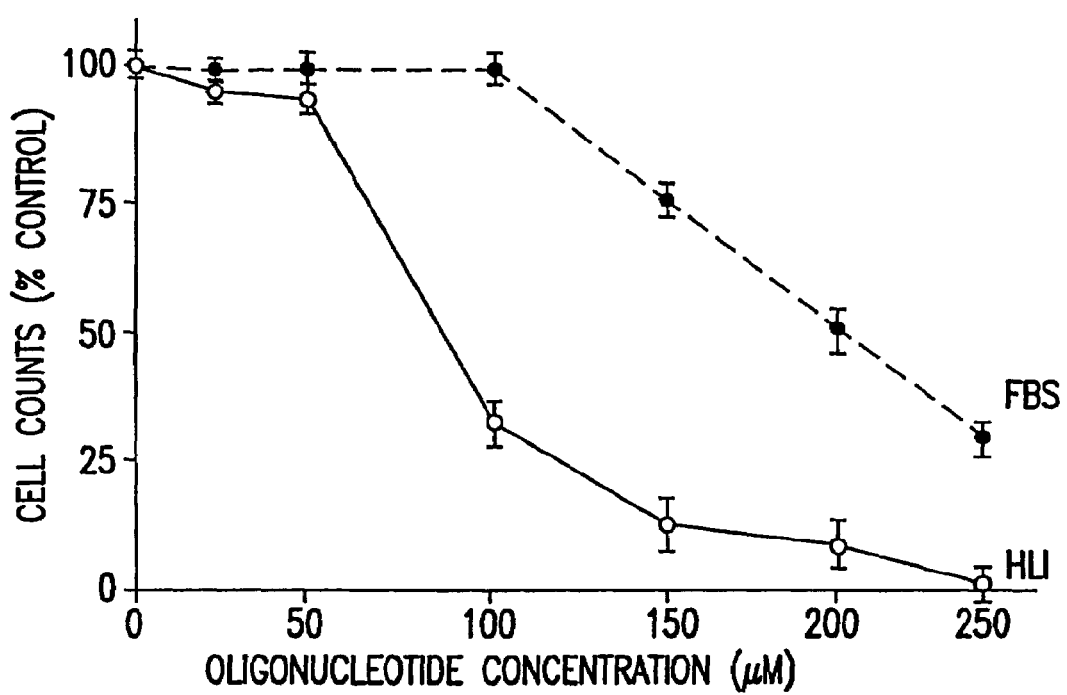
FIG. 5 is a graph showing the concentration—dependence of inhibition by an antisense oligonucleotide targeted against the translation initiation site of bcl-2 mRNA.

Concentration-Dependence of Inhibition by Antisense Phosphodiester Oligodeoxynucleotides in Serum-Free Cultures 697 pre-B cell leukemia cell were cultured in medium with either 1% (vol:vol) HL-1 concentrate (serum-free conditions or 3% (vol:vol) 68° C.-treated serum (FBS2), [●], see FIG. 5. Shown are cellular densities measured after 2 days in cultures containing various concentrations of phosphodiester TI-AS oligodeoxynucleotide. Data are shown as percentages relative to control cultures treated with a sense oligonucleotide, and reflect the mean±standard deviation for duplicate samples.

Example 14

Immunofluorescence Analysis of bcl-2 Protein Levels in Oligodeoxynucleotide-Treated 697 Cells For studies with oligodeoxynucleotides, $0.25 \times 10^4$ (for phosphorothioate) or $0.5 \times 10^5$ (for normal oligodeoxynucleotides), 697 cells were cultured in 1 ml of HL-1 serum-free medium in 24 well culture dishes (Linbro. Flow Labs, Inc.). After 2 days (for normal) or 4 days (for phosphorothioates), cells were recovered from cultures, washed once in [PBS, pH 7.4 (Gibco)–0.1% bovine serum albumin–0.1% sodium azide], and fixed for 5–10 minutes on ice in 1% paraformaldehyde/PBS solution. The cells were then washed once in PBS and incubated in 1 ml of absolute methanol at 20° C. for 10 minutes. After washing once in PBS-A, cells were then resuspended in PBS containing 0.05% Triton-X100 for 3 minutes on ice, washed in PBS-A and preblocked for 30 minutes at 4° C. in PBS with 10% (v/v) heat-inactivated goat serum.

For addition of the first antibody, preblocked cells were resuspended in 100 µl of PBS-G (PBS-1% goat serum-0.1% sodium azide) prior to aliquoting 50 µl into separate tubes that contained 1 µl of either BCL2 antibody (Halder et al., *Nature* (London), 342:195–197 (1989)) or affinity-purified normal rabbit control IgG (Cappel 6012-0080) and incubated for 1 hour on ice. The BCL2 antibody used for these studies was prepared in rabbits using a synthetic peptide corresponding to amino acids (98–114) of the BCL2 protein and was affinity— purified by protein-A-Sepharose chromatography and used at approximately 1 mg/ml. Cells were then washed in PBS-A and incubated in 0.5–1.0 ml PBS-A for 15–20 minutes on ice to allow diffusion of nonspecific cell-associated antibody prior to resuspending cells in 100 µl of PBS-G containing 5 µg of biotinylated scat anti-rabbit IgG (BAIOOO; Vector Labs) for 30 minutes. After washing once and incubating for 15 minutes in PBS-A, cells were finally resuspended in 100 µl of PBS-A containing 2 µg of FITC-conjugated avidin (Vector Labs A2011) for 20 minutes and washed three times in PBS-A prior to analysis with an Ortho cytofluorograph 50-H connected to an Ortho 2150 data-handling system. The specificity of method for detecting BCL2 protein was confirmed by immunofluorescence microscopy (showing cytosolic stain peptide competition, and studies of cell lines that expressed various levels of BCL2 mRNA and proteins though gene transfer manipulations.

For measurements of surface HLA-DR antigen expression, an indirect immunofluorescence assay method was used (Reed et al., *J. Immunol.* 134:1631–1639 (1985)) involving incubation of viable cells with a murine anti-HLA-DR monoclonal antibody (IgG2a) (Becton-Dickinson 7360) or a negative control antibody, R3-367 (IgG2a), followed by FITC-conjugated scat anti-mouse IgG (Cappel 1711-0081). Cells were fixed in 1% paraformaldehyde/PBS prior to FACS analysis.

Figure 6A:
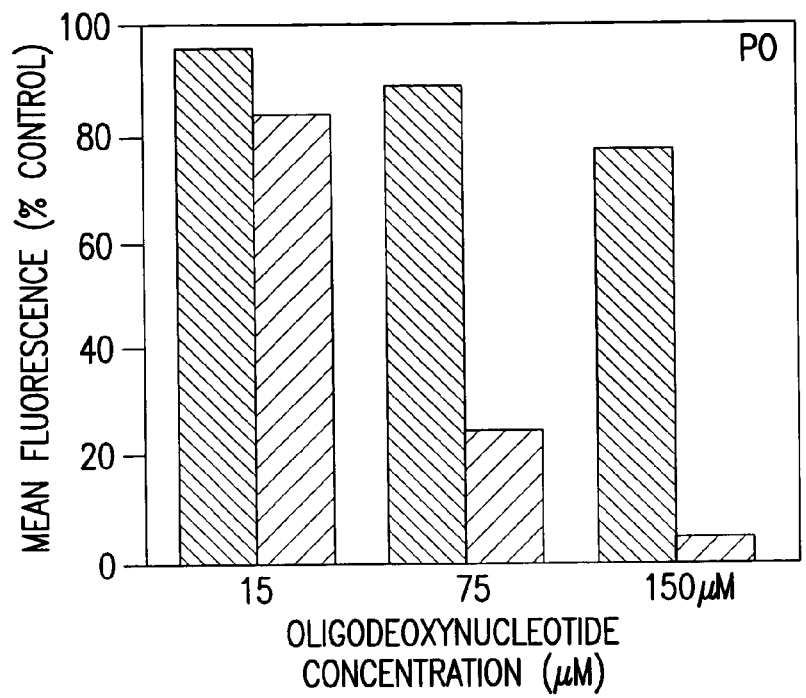
FIGS. 6 (a) and (b) are graphs showing the results of immunofluorescence analysis of bcl-2 protein levels in oligonucleotide-treated cells.
Figure 6B:
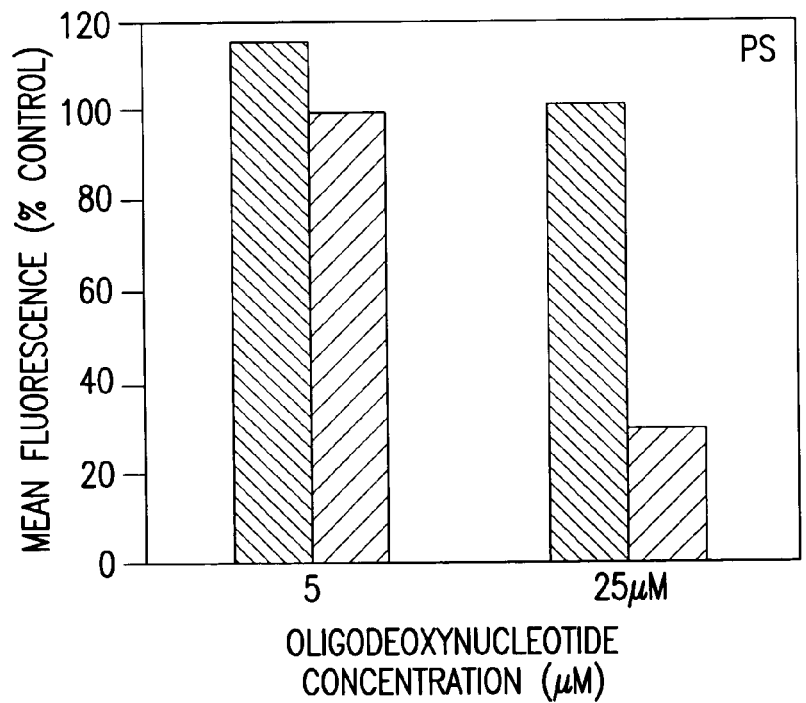
Figure 7A:
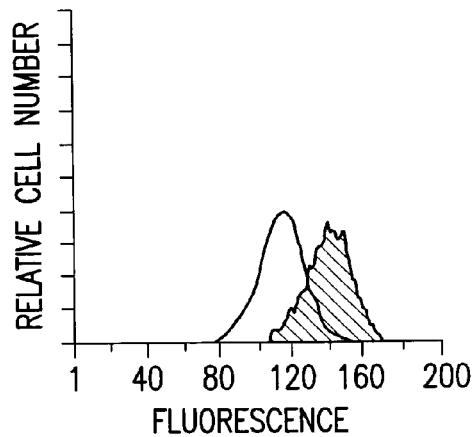
FIGS. 7 (a)–(d) are FACS profiles for 697 cells before and after treatment with bcl-2 antisense oligonucleotides.
Figure 7B:
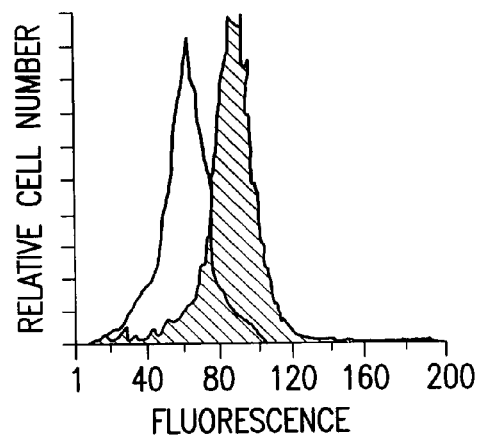
Figure 7C:
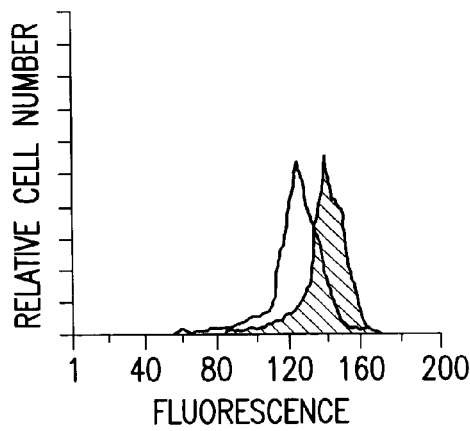
Figure 7D:
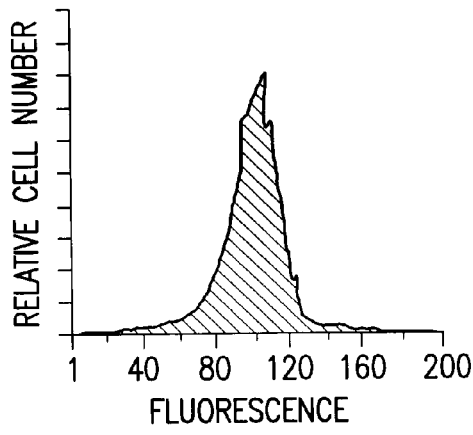

697 cells were cultured for 2 days (PO) or 4 days (PS) with various oligonucleotides. In FIG. 6, the black columns show the results with a sense oligonucleotide, and the hatched columns with an antisense oligonucleotide TI-AS. Cells were labeled with anti-bcl-2 antiserum and analyzed by FACS. Data are expressed as percentages relative to the mean fluorescence obtained with untreated 697 cells.

FIG. 7 shows typical FACS results obtained for 697 cells before and after treatment with 100 µM PO bcl-2 antisense oligonucleotides. A: untreated 697 cells labeled with either anti-bcl-2 antiserum (hatched area) or normal rabbit serum control (white area); B: untreated 697 cells labeled with either anti-HLA-DR antibody (hatched area) or a negative control antibody (white area); C: 697 cells cultured for 2 days with either normal bcl-2 TI-AS (white area) or TI-AS (hatched area) oligodeoxynucleotides and labeled with anti-bcl-2 antibody; D: 697 cells cultured with TI-AS and TI-S oligodeoxynucleotides (as in C), but labeled with anti-HLA-DR antibody.

As shown in FIGS. 6 (*a*) and (*b*), PO and PS bcl-2 antisense oligonucleotides produced specific concentration-dependent reductions in the levels of bcl-2 proteins, without altering the levels of expression of HLA-DR (FIG. 7) and other control antigens. At 150 µM, for example, PO antisense oligodeoxynucleotide caused an approximately 75–95% reduction in bcl-2 fluorescence, whereas the control sense oligonucleotide diminished bcl-2 protein levels by only 10–20% (FIG. 6(*a*)). Similarly, cultured 697 cells for 4 days with the PS antisense oligodeoxynucleotide ar 25 µM resulted in approximately 70% reduction in bcl-2 fluorescence. In comparison, the sense PS oligodeoxynucleotide TI-S inhibited bcl-2 protein levels by only approximately 15%, as measured by this assay (FIG. 6(*b*)).

In phosphorothioate oligodeoxynucleotides, one of the non-bridging oxygen atoms in each internucleotide phosphate linkage is replaced by a sulfur atom. This modification renders phosphorothioate oligodeoxynucleotides extremely resistant to cleavage by nucleases, Stein et al., *Nucl. Acids Res.*, 16:3209–3221 (1988). Despite the substitution of a sulfur atom for an oxygen, phosphorothioate oligodeoxynucleotides retain good solubility in aqueous solutions; hybridize well, though with some decrease in the melting temperature of RNA-oligodeoxynucleotides duplexes; and are synthesized conveniently by the widely employed method of automated oligodeoxynucleotides synthesis with phosphoroamidites.

Antisense bcl-2 phosphorothioate oligodeoxynucleotides have been found to be more potent inhibitors of leukemic cell grown than their normal oxygen-based counterparts. When treated under serum-free conditions, these oligodeoxynucleotides reduced cellular proliferation by half at concentrations of approximately 15–23 µM, whereas the normal oligodeoxynucleotide achieved 50% inhibition at 125–250 µM. This finding may be explained by the reduced sensitivity of phosphorothioate oligodeoxynucleotides to cellular nucleases, or may be attributable to other mechanisms. For example, mRNAs hybridized with phosphorothioate oligodeoxynucleotides may experience enhanced degradation through a mechanism involving an RNAse H-like activity.

Despite their increased inhibitory activity, phosphorathioate antisense oligodeoxynucleotides retained sequence-specificity. At the concentrations tested (less than 25 µM), sense versions of these oligodeoxynucleotides had little effect on leukemic cell growth. Both normal and phosphorothioate antisense oligodeoxynucleotides appeared to initially suppress the proliferation of leukemic cells through non-cytotoxic mechanisms. During the first few days of culture, cellular replication was inhibited without a concomitant rise in cell death. Later in these cultures (days 4–5 for normal oligodeoxynucleotides, days 6–8 for phosphorothioates), however, cellular viabilities declined.

Comparing the kinetics of inhibition by normal and phosphorothioate oligodeoxynucleotides revealed that the latter compounds have a slower onset of action. Maximal inhibition of leukemic cell proliferation by normal antisense oligodeoxynucleotides occurred two days after initiation of cultures, whereas phosphorothioate oligodeoxynucleotides required 4 to 7 days to achieve maximal inhibition.

The usefulness of anticode oligomers in inhibiting human lymphoma/leukemia cells and other types of cancer cells that express the bcl-2 gene has been shown by the examples herein. Anti-sense oligodeoxynucleotides complementary to at least an effective portion of the mRNA of the human bcl-2 gene has been found to inhibit growth of RS11846 human follicular lymphoma cells t (14;18) chromosomal translocation and high bcl-2 expression), 697 human pre B cell leukemia cells (high bcl-2 expression), JURKAT human acute lymphocytic leukemia cells (medium bcl-2 expression), normal human lymphocytes (medium bcl-2 expression) and murine fibroblasts (low bcl-2 expression). Although bcl-2 antisense reagents can suppress the growth of many types of cells, the t(14:18) lymphoma and leukemia cells seem to be the sensitive, allowing for specific inhibition of malignant cells.

As demonstrated in the following Examples, a variety of DNA analogs can be employed in the instant invention. For example, phosphorothioates, methylphosphonates, and mixed oligomers containing combinations of phosphodiesters and phosphorothioate or methylphosphonate nucleosides. It should be understood that RNA analogs can also be employed in the invention.

Example 15

Methylphosphonate (MP)/Phosphodiester (PO) bcl-2 Antisense Oligomers Induce Death of DoHH2 Lymphoma Cells The purpose of this study was to determine the efficacy of various analogs of the anticode oligomers for inhibiting lymphoma cell survival.

DoHH2 is a human lymphoma cell line containing a t(14:18)-translocation that activates the bcl-2 gene. DoHH2 cells were cultured for 3 days without oligomers or in the presence of various concentrations of antisense (As) and scrambled (Sc) methylphophonate (MP)/Phosphodiester (PO) oligomers for 3 days. Cell viability was assessed by trypan blue dye exclusions, and the data expressed as a percentage relative to DoHH2 cells cultured without oligomers. The MP/PO oligomers was an 18-mer targeted against the first 6 codons of the bcl-2 open reading frame in which 5 internal linkages were phosphodiester and the flanking nucleosides were methylphosphonates.

The results indicate that these anticode oligomer analogs are potent and specific inhibitors of lymphoma cell survival.

Example 16

Methylphosphonate (MP)/Phosphodiester (PO) Chimeric Oligomers Inhibit Growth of MCF-7 Human Breast Cancer Cells The purpose of this study was to determine the efficacy of the claimed anticode oligomer analogs to inhibit the survival of solid tumor cells which highly express bcl-2.

MCF-7 is a human breast adenocarcinoma cell line that contains relatively high levels of bcl-2 protein. The cells were cultured at 4,000 cells per well in 96-well microtiter plates in the presence or absence of MP/PO oligomers. Relative cell numbers per well were then estimated by MTT assay, based on a standard curve prepared using freshly plated, untreated MCF-7 cells. The antisense (As) and scrambled (Sc) MP/PO oligomers were the same as those described in Example 15. Data represent the mean±standard deviation for determinations.

The results demonstrate sequence specific inhibition of growth of solid tumor cells by the claimed anticode oligomer analogs.

Example 17

Optimization of Anticode bcl-2 Oligomer Sequences

The purpose of this study was to determine optimum target sites or sequence portions on mRNA for inhibiting cell survival by contacting the cells with various claimed anticode molecules whose sequences were computer generated.

Figure 13A:
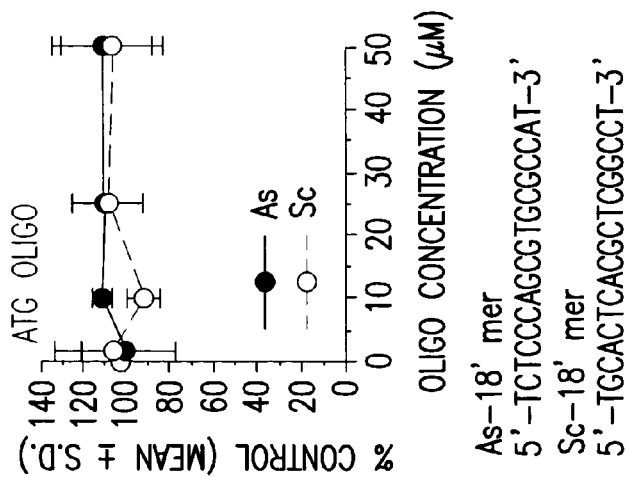
FIG. 13 shows optimization of antisense bcl-2 oligomer sequences using the oligonucleotides 5'-TCTCCCAGCGT-GCGCCAT-3' (SEQ ID NO:17), 5'-TGCACTCACGCTCG-GCCT-3' (SEQ ID NO:18), 5'-GCGCG-GCGGGCGGGCGGGCA-3' (SEQ ID NO:26), 5'-GGGCGGAGGCCGGCCGGCGG-3' (SEQ ID NO:27), 5'-AGCGGCGGCGGCGGCAGCGC-3' (SEQ ID NO:28 ) and 5'-GGGCCGGGAAGGGCGCCCGC-3' (SEQ ID NO:29).
Figure 13B:
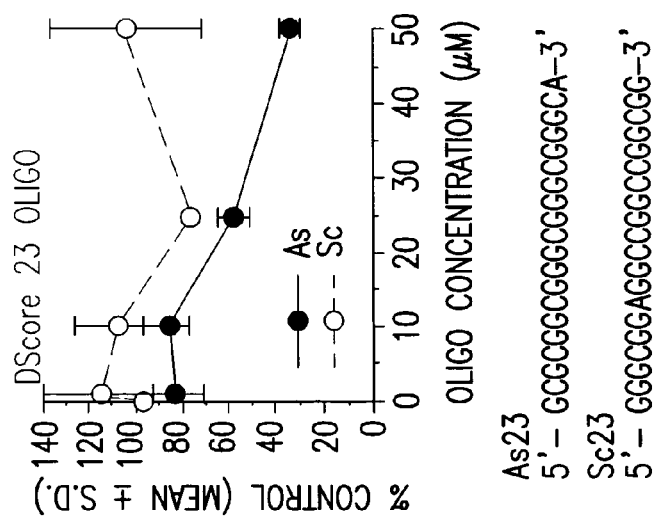
Figure 13C:
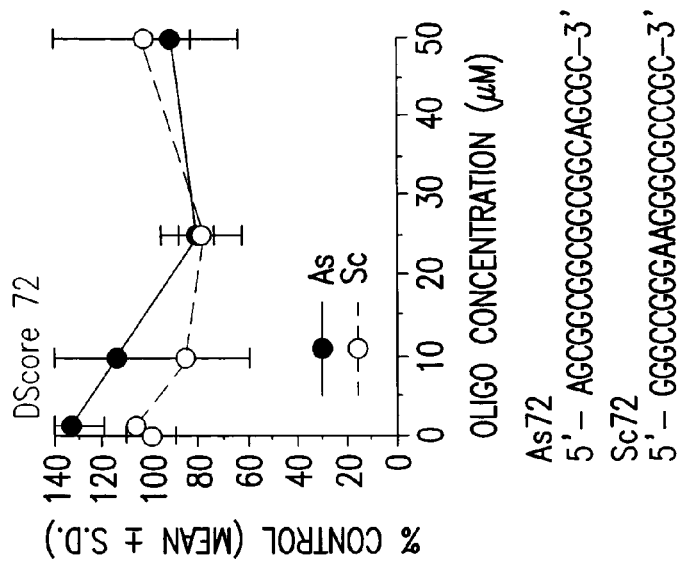

DoHH2 lymphoma cells were treated with various concentrations of oligomers targeted to different sites on the bcl-2 mRNA. The ATG oligomer (SEQ ID NO:17) targets the translation initiation site, and is complementary to the first 6 codons of the open reading frame. The Dscore 23 and Dscore 72 oligomers (SEQ ID NOS:26 and 28, respectively) target sites in the 5' untranslated region of the mRNA. Sc oligomers (SEQ ID NOS:25, 27, and 29) represent negative controls having the same length and base composition but in scrambled order. All oligomers were prepared as phosphodiester (PO)/phosphorothioate (PS) chimeras, where only the last (3') two internucleoside linkages were phosphorothioates. Oligomers were added directly to cultures and relative numbers of viable cells were estimated by MTT assay 3 days later. Data in FIG. 13 represent mean±standard deviation.

The results indicate that the Dscore 23 oligomer, targeted to the 5' untranslated region, has, compared to the other anticode oligomers tested in this Example, superior activity for inhibiting cell survival.

Example 18

Reversal of Chemoresistance of Tumor Cells by Antisense-Mediated Reduction of bcl-2 Gene Expression The following work was undertaken to determine if anticode oligomers directed against the expression of the bcl-2 gene would reverse chemoresistance, that is to say, increase the sensitivity to cancer chemotherapeutic agents in cancer tumor cells expressing the bcl-2 gene.

High levels of bcl-2 protein appeared to increase the relative resistance of lymphoid cells to killing induced by a wide variety of cancer chemotherapeutic agents including, but not limited to, Ara-C, MTX, vincristine, taxol, cisplatin, adriamycin, etoposide, mitozantron, 2-chlorodeoxyadenosine, dexamethasone (DEX), and alkylating agents. (Miyashita, T. and Reed, J. C., Cancer Res. 52:5407, Oct. 1, 1992). While these drugs have diverse biochemical mechanisms of action, it is believed that all have in common the ability to ultimately trigger cancer cell death by activating endogenous cellular pathways leading to apoptosis (Eastman, A. Cancer Cells 2:275 (1990)). It is understood that the claimed anticode molecules and analogs thereof as used herein are effective for their intended purposes of enhancing sensitivity to cancer chemotherapeutic drugs including, but not limited to, antimetabolites, alkylating agents, plant alkaloids, and antibiotics.

Antimetabolites include, but are not limited to, methotrexate, 5-fluorouracil, 6-mercaptopurine, cytosine arabinoside, hydroxyurea, 2-chlorodeoxy adenosine.

Alkylating agents include, but are not limited to, cyclophosphamide, melphalan, busulfan, cisplatin, paraplatin, chlorambucil, and nitrogen mustards.

Plant alkaloids include, but are not limited to, vincristine, vinblastine, and VP-16.

Antibiotics include, but are not limited to, doxorubicin (adriamycin), daunorubicin, mitomycin c, bleomycin.

Other cancer chemotherapeutic agents include DTIC (decarbazine), mAMSA, hexamethyl melamine, mitroxantrone, taxol, etoposide, dexamethasone.

In the present work, both nuclease resistance phosphorothioates (PS) and phosphodiesters in which only the 3'-most internucleoside bond was a thioate linkage (PO/PS) were employed. The PO/PS oligomers are resistance to 3' exonucleases (the principal nuclease activity of serum) and generally form more stable heteroduplexes with target RNAs.

Cationic lipids were used to improve the uptake and subsequent release of oligomers into effective intracellular compartments, and are exemplary pharmaceutical carriers for the claimed anticode oligomers.

The methods for preparing and purifying the antisense (AS) and scrambled (SC) 18'-mer oligonucleotides used for the present work are described above in General Methods and in Kitada et al. (*Antisense R & D*, 3:157 (1993)). Phosphordiester oligonucleotides were synthesized in a 10–15 micromole scale using phosphoroamidate chemistry with oxidation by iodine, and then purified using a $C_{18}$-reverse phase column. In most cases, oligomers were additionally ethanol-precipitated five times to eliminate any nonspecific cytotoxic activity, and then dried and resuspended in sterile HL-1 medium (Venetrex Labs, Inc; Burlingame, Calif.) at 1–10 mM. The pH of this solution was adjusting using 1–10 M NaOH until the phenol red indicator dye in the media returned to its original color.

The principle oligomers used were 18-mers, having either the sequence:

I. TCTCCCAGCGTGCGCCAT (SEQ ID NO. 17), which is antisense to the first six codons of the human bcl-2 open reading frame (SEQ ID NO. 19); or II. TGCACTCACGCTCGGCCT (SEQ ID NO. 18), which is a scrambled version used as a control.

Standard transfection methods were used to produce tumor cells expressing either the bcl-2 gene or an antisense oligodeoxynucleotide which bound to bcl-2 mRNA. It is understood that the vector could also encode an antisense oligodeoxynucleotide which binds to bcl-2 pre-mRNA. The particular nucleotide sequence encoding the antisense oligonucleotides of the invention is not critical, except that the sequences are preferably chosen such that they express antisense oligodeoxynucleotides sufficient to reduce bcl-2 gene expression in tumor cells and increase the sensitivity of the tumor cells to cancer chemotherapeutic agents or sufficient to kill tumor cells when they are treated with cancer chemotherapeutic agents. It is only necessary that the antisense oligodeoxynucleotide encoded in vector is expressed under conditions sufficient to reduce bcl-2 gene expression in tumor cells. The methods used for preparing vectors, and, in particular, expression plasmids, for transferring genes into mammalian cells relies on routine techniques in the field of molecular biology. A basic text disclosing the general methods of preparing expression plasmids used in this invention is *Molecular Cloning, A Laboratory Manual*, 2nd Edition, eds. Sambrook et al., Cold Spring Harbor Laboratory Press, (1989), particularly chapter 16 on Expression of Cloned Genes in Cultured Mammalian Cells. Examples 15C–D below set forth particular methods for preparing the expression plasmids used in the present invention. The particular vector used to transfer the antisense oligonucleotides of the present invention is not critical, and such vectors may include vectors derived from lambda and related phages or from filamentous phages. It is only necessary that the transferred nucleotide sequence encoding the antisense oligonucleotides of the present invention be expressed in the transfected tumor cell under conditions sufficient to reduce the bcl-2 gene expression in the tumor cell. The present invention includes expression of the antisense oligonucleotide either from an extrachromosomal position (e.g. from an expression plasmid) or from a position integrated into the host genome itself, as mediated by other vectors, such as recombinant retroviral vectors (Reed et al. bcl-2 mediated tumorigenicity in a T-cell lymphoid cell line: synergy with C-MYC and inhibition by bcl-2 antisense. *PNAS USA* 87:3660 (1990)).

A. Treatment of Lymphoma Cells With 18-mer Synthetic bcl-2 Antisense Oligodeoxynucleotides.

Lymphoma cell line SU-DHL-4, obtained from a use of diffuse, histiocytic, non-Hodgins, lymphoma (Epstein et al. Two new monoclonal antibodies (LN-1, LN-2) reactive in B5 formalin-fixed, paraffin-embedded tissues with follicular center and mantle zone human B lymphocytes and derived tumors. *J. Immunol.* 133:1028 (1984)) and containing a t(14; 18) translocation was treated with 18-mer synthetic bcl-2-AS oligodeoxynucleotides targeted for binding with the first six codons of the bcl-2 mRNA. As a control, SU-DHL-4 cells were treated with various control oligomers, including 18-mers having the same nucleoside composition as the AS oligomer, but in which the bases were in scrambled order (SC).

Aliquots of 1.5 ml of HL-1 serum-free medium (Ventrex Labs, Inc.) supplemented with 1 mM L-glutamine, 50 Units/ml penicillin, and 100 μg/ml streptomycin and either 5 μg of purified oligonucleotides or 30 μg of Lipofectin$^R$. [1:1 mixture of N-(1-(2,3-dioleyloxy)propyl)-N,N,N-trimethylammonium chloride (DOTMA) and dioleoylphophotidylethanolamine (DOPE)] were combined and added to 0.75× $10^6$ SU-DHL-4 cells in 3 mls of HL-1 medium. Cells were then either cultured at 37° C. in a humidified atmosphere of 5% $CO_2$/95% air in 24 well plates (2 mls/well) for immunoblot and RT-PCR assays, or in 96-well flat-bottom microtiter plates (0.1 ml/well) for MTT assays. For cells in microtiter cultures, typically 0.1 ml of additional HL-1 media with or without various chemotherapeutic drugs was added after 1 day, and the cells were cultured for an additional 2 days before performing MTT assays.

Cells were washed once in PBS, lysed in a buffer containing 1% Triton X100, and samples normalized for protein content (25 μg) prior to size-fractionation of proteins of SDS-PAGE (12% gels) and transfer to nitrocellulose filters for immunoblot assays as described in Reed et al. *Cancer Res.* 51:6529 (1991). Preliminary experiments determined that aliquots of lysates containing 25 μg of total protein produced results in the linear range of the assay. Blots were first incubated with 0.1% (v.v) of a rabbit antiserum directed against a synthetic peptide corresponding to amino-acids (aa) 41–54 of the human Bcl-2 protein, as shown in SEQ ID NO. 21 (id) followed by 2.8 μg/ml biotinylated goat anti-rabbit IgG (Vector Labs, Inc.). Bands corresponding to p26-Bcl-2 were then visualized by color development using a Horseradish Peroxidase (HRP)-avidin-biotin complex reagent (Vector Labs, Inc) and 3,3'-diaminobenzidine (DAB). Stained blots were then incubated with a second anti-Bcl-2 antibody directed against aa 61–76 of the Bcl-2 protein (SEQ ID NO. 21) followed by 0.25 μCi/ml $^{125}$I- protein A. Bcl-2 bands were excised from the blots and subjected to gamma-counting.

Despite the mitochondrial location of Bcl-2 protein, no difference in the rate of MTT dye reduction by mitochondrial enzymes was noted in cells that were identical except for their levels of p26-Bcl-2. These comparisons were made using pairs of exponentially growing lymphoid cell lines that differed only in that one line had been stably infected with a recombinant bcl-2 retrovirus and the other with the parental retroviral vector lacking a bcl-2 cDNA insert (Miyashita et al. *Cancer Res.* 52:5407 (1992); *Blood* 81:151 (1993)).

Anticode specific reductions in the relative levels of bcl-2 mRNA were detected within 1 day at a semi-quantitative reverse transcriptase polymerase chain reaction (RT-PCR) assay. See FIG. 8A.

Figure 8A:
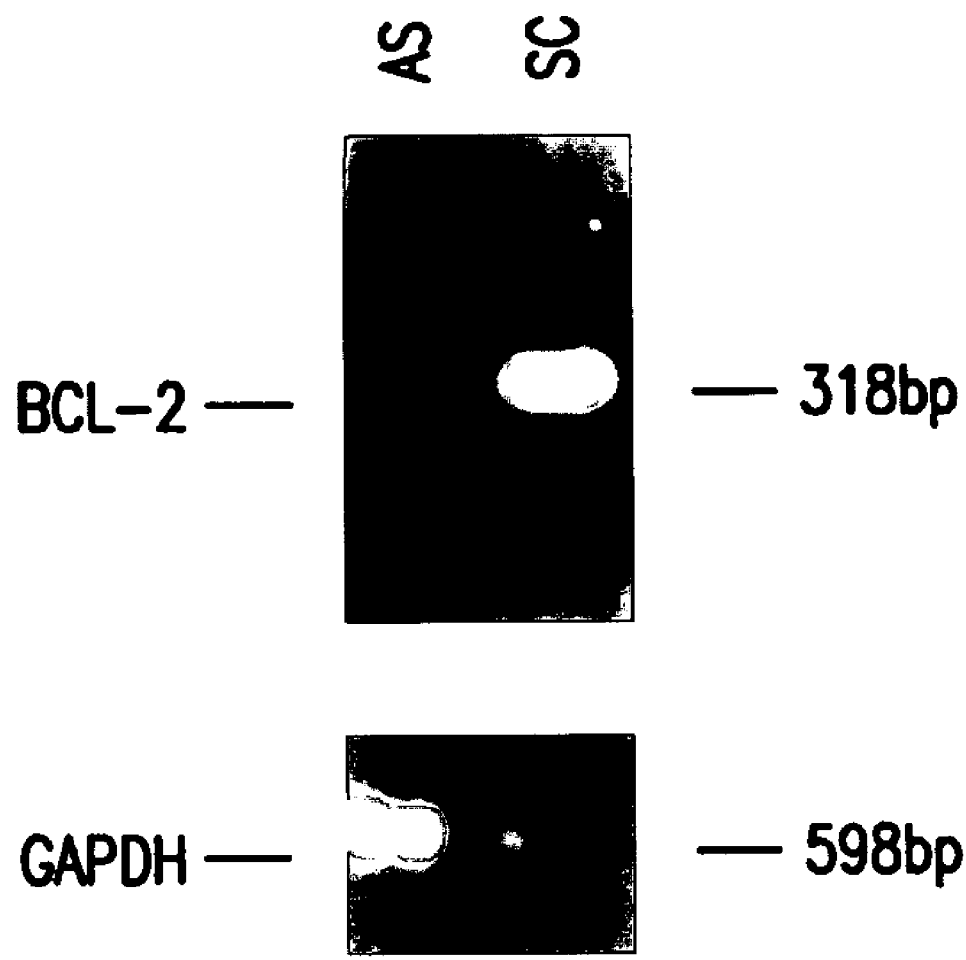
FIGS. 8 (a)–(c) show bcl-2 antisense oligodeoxynucleotides producing sequence-specific reductions in bcl-2 mRNA and bcl-2 protein and producing increased sensitivity of SUDHL-4 cells to cancer chemotherapeutic drugs.

SU-DHL-4 cells were cultured with 0.83 ug/ml of oligomers complexed with 5 ug of cationic lipids (Lipofectin; BRL/Gibco, Inc.) per ml of serum-free media y(13,19). In FIG. 8A, total RNA was isolated from cells after 1 day and relative levels of bcl-2 and glyceraldehyde 3'-phosphate dehydrogenase (GAPDH) mRNAs were assessed by RT-PCR assay as described in Kitada et al., *Antisense R & D* 3:157 (1993)).

Figure 8B:
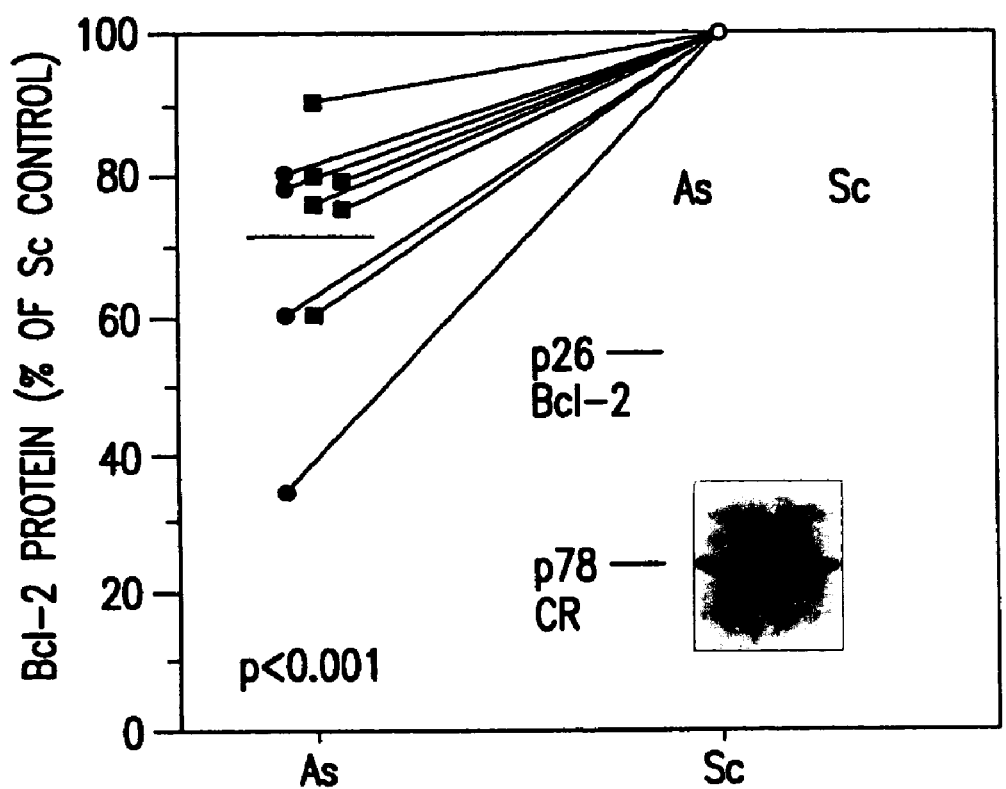

In FIG. 8B, SU-DHL-4 cells were cultured with pairs of either PS (squares) or PO/PS (circles) As- and Sc-oligomers for 3 days. Relative levels of Bcl-2 protein were then measured using a quantitative immunoblot assay, as described above, and the data expressed as a percentage relative to cells treated with control Sc-oligomers. The inset shows immunoblot results for p26-Bcl-2 and a p78 cross-reactive (CR) band in a case where As-PO/PS oligomer produced a 41% relative decrease in Bcl-2 protein levels. In FIG. 8C, $10^{-4}$ M Ara-C, MTX, or DEX was added 1 day after addition of PS (squares) or PO/PS (circles) oligomers to cultures of SU-DHL-4 cells, and MTT assays were performed on day 3. Data are represented as a % control relative to cells cultured with drugs in the absence of any oligomers, and represent the results of 9 to 10 consecutive experiments [in one embodiment, the MTT assay failed]. Similar results were obtained when dye exclusion assays were used to assess cell survival rather than MTT assay [not shown].

Mean values for the data are indicated by horizontal lines. Statistical analysis of the data was by paired t-test (As versus Sc). Concentrations of As- and Sc-oligomers (≈150 nM) were adjusted to maximize As effects while maintaining sequence specificity.

Variations in the amounts of starting RNA were controlled for by Rt-PCR analysis using primers specific for GAPDH mRNA.

The long half-life of the bcl-2 protein (approximately 14 hours) may account for the AS-mediated reductions in bcl-2 proteins not being as dramatic as for reductions in bcl-2 mRNA, taking longer to achieve (about 3 days), and appearing more variable.

FIG. 8B shows the composite results for 10 experiments where relative levels of bcl-2 protein were compared in SU-DHL-4 cells treated with AS or SC oligomers. AS-mediated reductions in bcl-2 protein level ranged from as much as 66% to as little as 10%, with an average relative reduction of about 30%, compared to SU-DHL-4 cells that were treated in the identical manner with control oligomers. Levels of a variety of control mitochondrial proteins such as $F_1$-beta-ATPase and cytochrome C, which like bcl-2 are encoded by nuclear genes, were not adversely affected by AS-oligomers (not shown), indicating that the AS-mediated reductions in bcl-2 protein levels were specific. The insert in FIG. 8B, for example, shows a comparison of p26-Bcl-2 with a 78-kDa protein that cross reacts with one of the rabbit antisera employed for immunoblot assays, demonstrating a decrease in the levels of p26-bcl-2 but not p78 in the AS-treated cells relative to cells that received control SC-oligomers.

B. Effect of Treatment of SU-DHL-45 Cells with bcl-2 AS Oligomers on Cell Sensitivity to Cancer Chemotherapeutic Agents This study was performed to determine whether treatment of SU-DHL-4 cells with bcl-2 AS-oligomers could increase their relative sensitivity to killing by the cancer chemotherapeutic agents Ara-C, MTX, and DEX, which are anticancer drugs.

Previous control studies demonstrated that bcl-2 AS oligomers had little or no effect on SU-DHL-4 cell growth and survival at least during the first three days of culture (Kitada et al. *Antisense R & D* 3:157 (1993)). AS-mediated reductions in bcl-2 protein levels in these lymphoma cells as well as in other cells do not typically accelerate the rate of cell death in cultures unless the cells are deprived of serum growth factors (Reed et al. *Proc. Natl. Acad. Sci. USA* 87:3660 (1990)).

In the present work, preliminary studies demonstrated that more than 90% of SU-DHL-4 cells survived treatment for 4 days with high dose ($10^{-4}$) Ara-C, MTX or DEX, presumably because of their high levels of bcl-2 protein (Not shown). At these concentrations, however, all drugs induced essentially complete inhibition of SU-DHL-4 cell proliferation, consistent with bcl-2 conversing drugs from cytotoxic to cytostatic. Comparisons of AS and SC oligomers demonstrated that bcl-2 AS treatment markedly enhanced the sensitivity of these lymphoma cells to MTX and Ara-C, and to a lesser extent to DEX (FIG. 8C).

Despite some variability in results, on average, the addition of bcl-2 AS oligomers to cultures of SU-DHL-4 cells treated with MTX or Ara-C resulted in 79–84% greater inhibition (reduction in viable cell numbers) than use of either drug alone (P<0.002 for AS versus SC) in the absence of introducing the bcl-2 AS oligomers of the invention. Statistically significant results were obtained for DEX-treated SU-DHL-4 cells (P=0.01). The 20–30% reduction in viable cell numbers observed for control oligomer-treated cells could reflect a degree of sequence non-specificity, but was probably related to the use of cationic lipids to facilitate oligomer delivery into cells.

C. Effect of Transfecting Cells with Expression Plasmids Encoding Human bcl-2 Protein on Sensitivity to Chemotherapeutic Agents.

To further confirm the sequence specificity of bcl-2 AS oligomers for enhancing sensitivity to chemotherapeutic anticancer drugs, a study was conducted using an Interleukin-3 (IL-3)-dependent murine hemopoietic cell line 32D.C13 that had been stably transfected with expression plasmid encoding either the human bcl-2 protein or a viral homolog of bcl-2, BHRF-1, which has only 22% homology with bcl-2. 32D.C13 cells were obtained from Dr. Giovanni Rovera of the Wistar Institute, Philadelphia, Pa.

Treatment of 32D cells with oligomer/cationic lipid complexes was as described above except that 50 Units/ml of murine recombinant IL-3 (rIL-3) was included in the HL-1 media, the initial cell density was $10^5$ per ml, and replication-defective adenovirus dl312 (MOI=200) was added 30 minutes after exposure of cells to oligomers to facilitate exit of DNA from endosomes [Yokshimura K, et al. J. Biol Chem. 268, 2300, (1993)].

32D cells that had been stable transfected with expression plasmids encoding either human p26-Bcl-2 or EBV p19-

BHRF-1 (Takayama, S. et al. submitted) were cultured in medium ($10^5$/mi) containing IL-3 and PO/PS oligomers for 3 days to achieve reductions in human Bcl-2 protein levels. The cells were then retreated with oligomers alone (C) or in combination with various concentrations of MTX and the relative number of viable cells assessed by MTT assay 2 days later. Data represent mean±standard deviation for triplicate determinations and are expressed as a % relative to cells that received no MTX. Statistical analysis of data for $10^{-6}$ to $10^{-4}$ M MTX was by a 2-way Analysis of Variables method (Finney, D. J. *In Statistical Methods in Biological Assays*, p. 72, 1978 (3rd edition, Charles Griffin & Co., London). Comparable results were obtained with dye exclusion assays (not shown).

RNAs derived from the human bcl-2 construct in 32D-BCL-2 cells were a target for bcl-2 AS oligomers, whereas RNAs from the BHRF-1 expression plasmid are not. Thus the chemosensitivity to cytotoxic drugs of 32D.C13 cells expressing BHRF-1 should have been unaffected by the AS treatment.

Preliminary experiments demonstrated that upon withdrawal of IL-3 from 32D.C13 cells, levels of endogenous mouse bcl-2 protein declined and the cells underwent apoptosis. bcl-2 and BHRF-1 comparably supported the survival of 32D.C13 cells in the absence of IL-3, and the proliferative rates of 32D.C13 cells containing high levels of these proteins were similar in the presence of IL-3, thus excluding these variables as explanations for any differences in chemosensitivity.

Figure 9A:
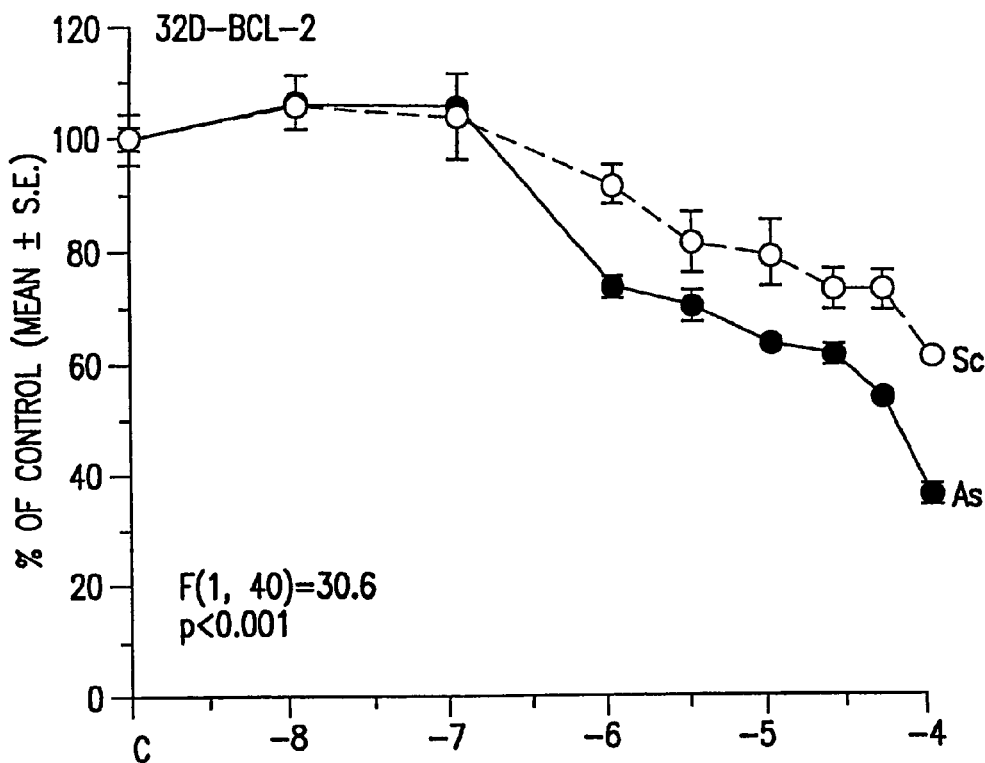
FIG. 9 demonstrates the differential effects of bcl-2 antisense oligomers on chemosensitivity of 32D-bcl-2 and 32D-BHRF-1 cells.
Figure 9B:
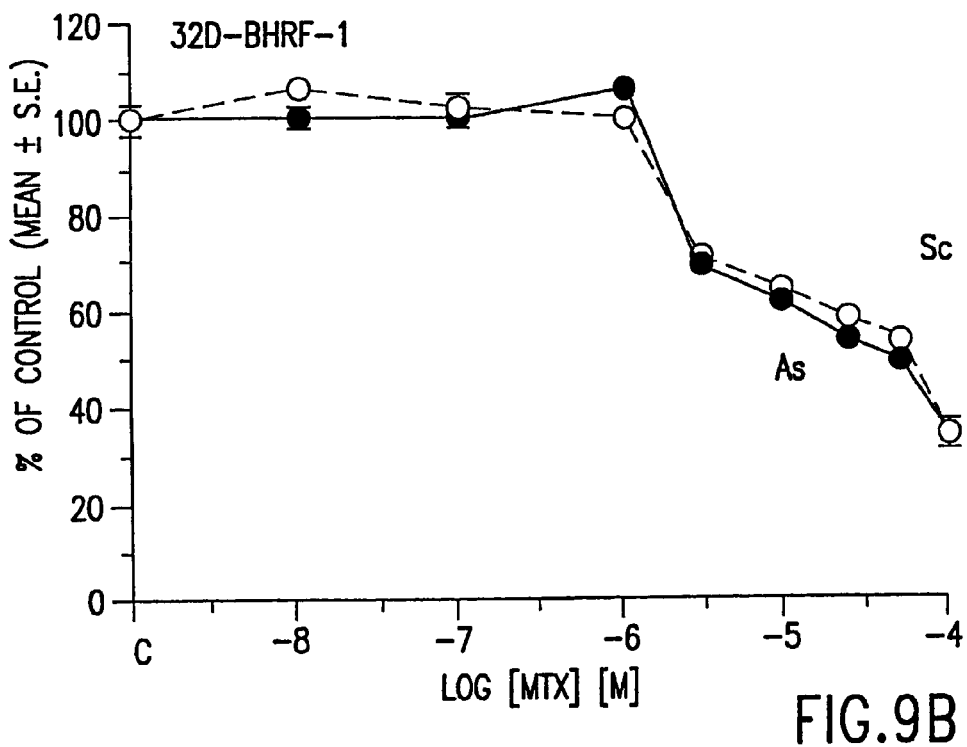

FIG. 9 compares the sensitivity of 32D-BCL-2 and 32D-BHRF-1 cells to various concentrations of MTX. Treatment with bcl-2 AS-oligomers resulted in sequence-specific increases in the sensitivity of 32D-BCL-2 cells to inhibition by MTX at concentrations of $10^{-6}$ to $10^{-4}$ M ($P \leq 0.001$ for AS versus SC). In contrast, treatment with bcl-2 AS oligomers produced no significant difference in the sensitivity of 32D-BHRF-1 cells to MTX, relative to control SC-oligomers (FIG. 9). These data indicate that the effects of bcl-2 AS oligomers on chemosensitivity to cytoxic agents drugs are sequence specific. Furthermore, several other control oligomers, including bcl-1 sense, other scrambled sequences with the same nucleoside composition as AS, and oligomers with totally unrelated sequences all had comparatively little effect on the chemosensitivity of the cells (Not shown).

The findings above demonstrated that bcl-2 AS oligomers produced sequence specific reductions in bcl-2 mRNA and bcl-2 protein levels and that these events were associated with increased sensitivity to chemotherapeutic agents such as anticancer drugs. The portion of tumor cells killed by the chemotherapeutic agents was greater than the portion killed by the same amount of chemotherapeutic agents in the absence of introducing the bcl-2 AS oligomers of the invention.

D. Effects of Transfecting Cells With Expression Plasmids Encoding Human bcl-2 Protein on Sensitivity of Lymphoma Cells to Chemotherapeutic Agents.

A different strategy was employed to determine if AS-mediated reductions in bcl-2 gene expression could be achieved with an inducible bcl-2 AS expression plasmid that used a heavy metal responsive the human metallothionein-IIA promoter in another translocation t(14:18)-containing lymphoma line, RS11846. RS11846 was obtained from Dr. Carlo Croce (Wistar Institute, Philadelphia, Pa.) (Tsujimoto and Croce, *Proc. Natl. Acad. Sci. USA* 83:5214 (1986)).

To prepare the expression plasmid a 0.91 kp bcl-2 cDNA (ibid) was subcloned in either antisense (AS) or sense (S) orientation into a HindIII site downstream of a human metalothionein-IIA promoter in the plasmid pMEP-4 (Invitrogen, Inc.), which contains a hygromycin phosphotransferase gene and the EBNA-1 gene and origin of DNA replication from Epstein-Barr Virus for high copy episomal maintenance.

RS11846 cells ($5 \times 10^{106}$) in Dulbecco's phosphate buffered saline containing 30 ug of plasmid DNA were electroporated (1500 uF, 270 V/cm) using a Cellject Electroporation System from EquiBio, Inc. Cells were returned to their usual culture media (RPMI-L 1640 supplemented with 10% fetal bovine serum, 1 mM L-glutamine, 50 Units/ml penicillin, and 100 ug/ml streptomycin) at $2 \times 10^5$ cells per ml and cultured for 2 days before seeding cells at $2 \times 10^5$ per ml in media containing 200 µg/ml hygromycin. After 3 weeks of culture, the resulting bulk cell lines were passaged in successively higher concentrations of hygromycin in 200 µg/ml increments until the concentration reached 1 mg/ml (about 4 weeks).

Hygromycin-resistant RS11846 cell were cultured in RPMI/10% serum media containing 0.5 µM $CdCl_2$ and 3 days later immunoblot assays were performed using 25 ug protein/lane essentially as described in Tanaka S, et al. *J. Biol. Chem.* 268, 10920 (1993) and in Reed et al. *Cancer Res.* 51:6529 (1991)).

Figure 10A:
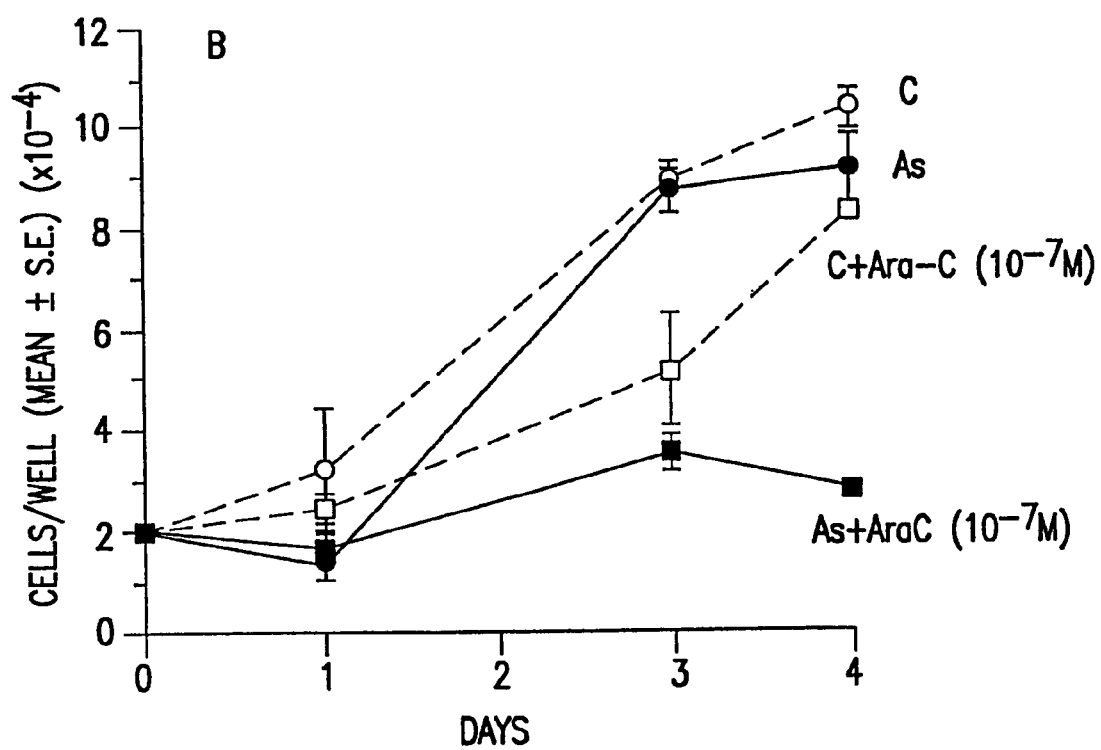
FIGS. 10 (a) and (b) show reduction of chemoresistance of RS11846 cells from inducible bcl-2 antisense expression from an expression plasmid.
Figure 11:
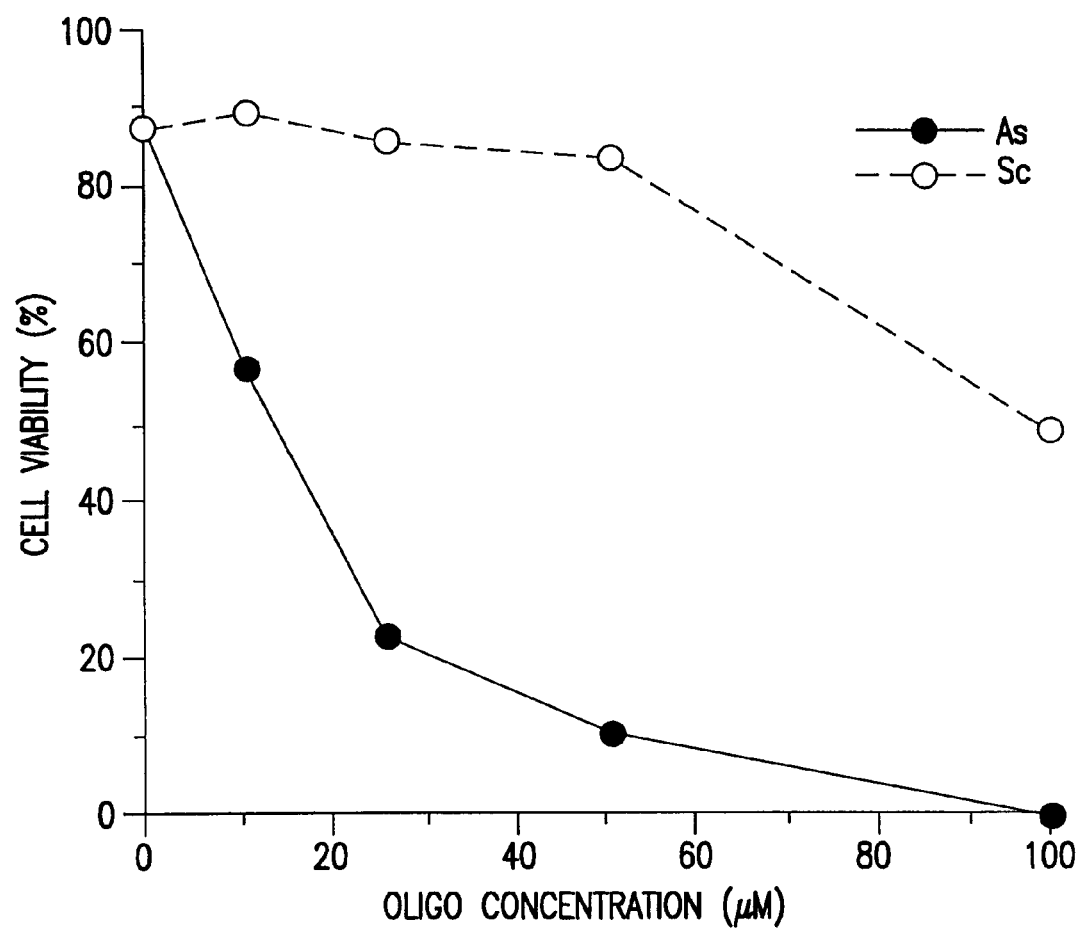
FIG. 11 shows methylphosphonate/phosphodiester bcl-2 antisense oligomers inducing death of DOHH2 lymphoma cells.
Figure 12:
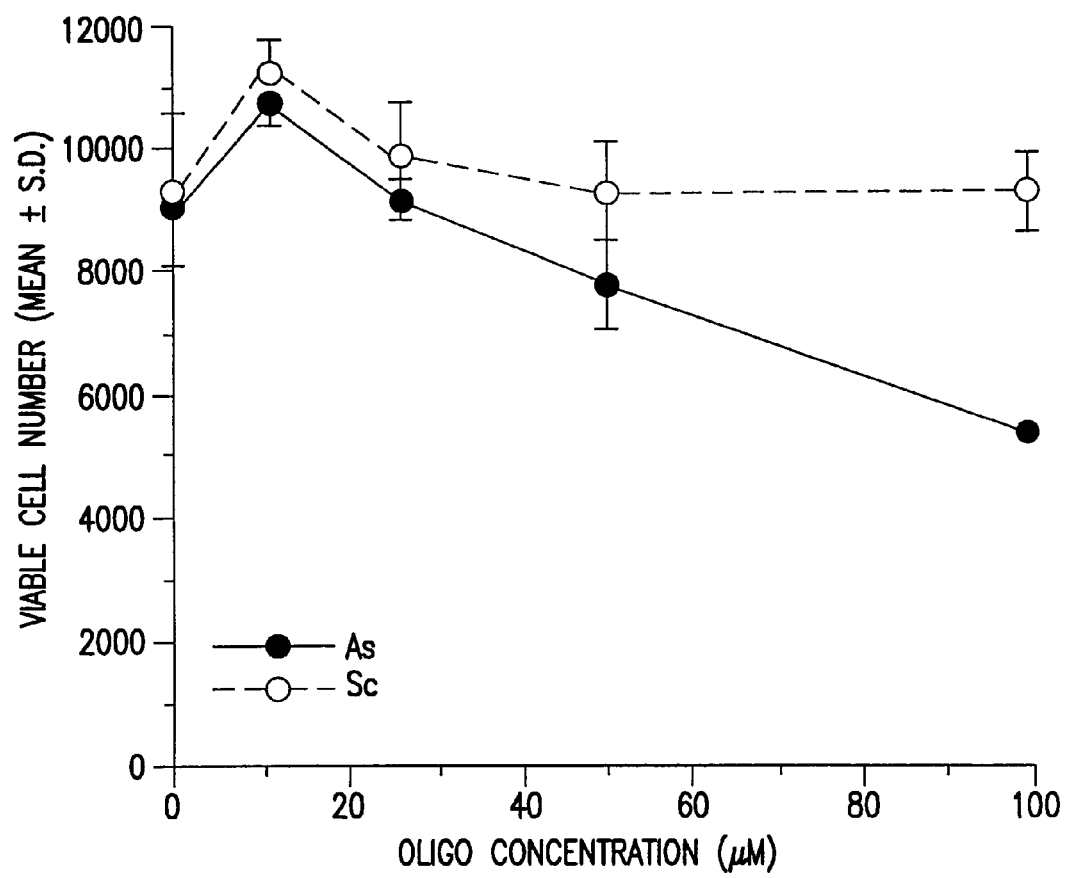
FIG. 12 shows methylphosphonate (MP)/Phosphodiester (PO) chimeric oligomers inhibiting growth of MCF-7 human breast cancer cells.

As summarized in FIG. 10, control ("c") and bcl-2-As ("As") plasmids were introduced into RS11846 cells and expression was induced with either 0.5 uM $CdCl_2$ or 50 uM $ZnCl_2$ for various times. As an additional control, RS11846 cells containing inducible plasmids with the bcl-2 cDNA in sense ("S") orientation were also analyzed. RS11846 cells were induced for 3 days and relative levels of Bcl-2 and $F_1$-β-ATPase proteins were assessed by immunoblot assay of Tanaka et al. *J. Biol. Chem.* 268:10920 (1993). In FIG. 10A, RS11846 cells were cultured at $10^5$ cells/ml in medium containing 0.5 uM $CdCl_2$ and 1 day later $10^{-7}$ M Ara-C or an equivalent volume of diluent control was added. Relative numbers of viable cells were estimated from MTT assays at various times and the mean±S.D. calculated for triplicate samples. In FIG. 10B, RS11846 cells were cultured as in FIG. 10A, except that various concentrations of Ara-C, MTX, or DEX were added. Data represent mean±S.D. for triplicate samples. Statistical calculations are by 2-way Analysis of Variables. DEX served as a negative control here since RS11846 cells have lost glucocorticoid receptors.

Preliminary experiments demonstrated that RS11846 cells tolerated the addition of up to 0.5 µM $CdCl_2$ or to 50 µM $ZnCl_2$ to cultures for one week, experiencing a slight decrease in growth rate but essentially no decline in percentage cell viability (Not shown).

In the absence of heavy metal induction, the relative levels of bcl-2 protein in RS11846 cells containing the control or bcl-2 AS plasmid were comparable, as determined by immunoblot assays (Not shown). When 0.5 µM $CdCl_2$ or 50 µM $ZnCl_2$ was added, reductions in bcl-2 protein became evident in the AS-expressing cells at 2 days and maximal inhibition of 30–40% was obtained at three to four days, relative to control RS11846 cells.

FIG. 10A shows an example of immunoblot lot data derived from RS11846 cells after three days of exposure of 0.5 mM $CdCl_2$, demonstrating reduced levels of bcl-2 protein in the AS-plasmid containing cells compared to RS11846 cells that harbored the control plasmid. The relative levels of a control mitochondrial protein $F_1$-beta-ATPase were comparable in all cell lines, consistent with sequence-specific alterations in bcl-2 protein levels.

When RS11846 cells containing either the control or bcl-2-As plasmids were cultured or various times in 0.5 µM CdCl$_2$, or 50 µM ZnCl$_2$, no significant difference in the growth rates of these two cell lines was observed (FIG. 8B). Thus, As-mediated reductions in Bcl-2 protein levels by themselves did not impair RS11846 cell proliferation or survival.

Inclusion of low-dose Ara-C (10$^{-7}$M) in the cultures of control RS11846 cells resulted in only a slight decline in the net numbers of viable cells, presumably because of the high levels of Bcl-2 protein found in these t(14;18)-containing lymphoma cells. In contrast, addition of 10$^{-7}$M Ara-C to cultures of bcl-2-AS expressing RS11846 cells was markedly inhibitory (FIG. 8B). Ara-C, however, had no effect on bcl-2 AS-expressing RS11846 cells in the absence of heavy metal induction of the MT promoter, when directly compared with RS11846 cells containing the control plasmid under the same conditions (not shown). FIG. 8C shows that the enhanced sensitivity to Ara-C observed for bcl-2-AS-expressing RS11846 cells occurred over a wide range of drug concentrations (P<0.001). Heavy-metal induction of the bcl-2-AS expression plasmid also significantly increased the relative sensitivity of RS11846 lymphoma cells to MTX (P<0.001), but not to DEX. Glucocorticoid receptor binding assays demonstrated that RS11846 cells have lost receptors for these steroid hormones [not shown], thus providing a specificity control showing that AS-mediated reductions in bcl-2 protein levels are by themselves insufficient to impair the growth or survival of these lymphoma cells.

Using a plurality of anticode approaches, the present invention demonstrated that average reductions of 30–40% in the relative levels of bcl-2 protein markedly enhanced the sensitivity of lymphoma cells, in particular, t(14;18)-containing lymphoma cell lines to chemotherapeutic agents such as conventional anticancer drugs. These examples demonstrated that introducing the claimed anticode oligomers into tumor cells achieves a reduction of bcl-2 expression and increases the chemosensitivity of neoplastic cells to chemotherapeutic agents or anticancer drugs.

Accordingly, the present invention achieved a method of killing tumor cells by introducing to tumor cells anticode oligomers which reduce bcl-2 gene expression or impair Bcl-2 protein function before contacting the cells with chemotherapeutic agents including anticancer drugs. The conventional anticancer drugs reduced the numbers of viable malignant cells, and the portion of tumor cells killed was greater than the portion which would have been killed by the same amount of drug in the absence of introducing the anticode oligomers into the cells.

Having thus disclosed exemplary embodiments of the present invention, it should be noted by those skilled in the art that this disclosure is exemplary only and that various other alternatives, adaptations, and modifications may be made within the scope of the present invention. Accordingly, the present invention is not limited to the specific embodiments as illustrated herein, but is only limited by the following claims.

SEQUENCE LISTING

<160> NUMBER OF SEQ ID NOS: 37

<210> SEQ ID NO 1
<211> LENGTH: 5084
<212> TYPE: DNA
<213> ORGANISM: Mus musculus

<400> SEQUENCE: 1

```
cggcacgagg aggagtggag cggcgcggga gggcgcgcag cttggttgct ccgtagtacg      60
gcggctcgca agggagcatc ccgagcgggc tccgggacgg ccgggaggca ggcaggcggg     120
cgggcgggga tggtgtgcgc ggctgcggac tcggcgttcc tcgcgcggcg tgcgggctgc     180
actgatttgt gtgaggggcg gccgcgcgca cccgcccgga gatgaggcgt cgatcagcaa     240
ggtgaacgta atagaaccat ggctcagttt cccacacctt tcggtggtag cctggatgtc     300
tgggccataa ctgtggagga aagggccaag catgaccagc agttccttag cctgaagccg     360
atagcgggat ttattactgg tgatcaagcg aggaactttt ttttccaatc tgggttacct     420
cagcctgtct tagcacaaat atgggcgcta gcggacatga ataacgatgg aaggatggat     480
caagtggaat tttccatagc catgaagctt atcaaactga agctacaagg atatcagctc     540
ccctccacac ttccccctgt catgaaacag caaccagtgg ctatttccag tgcaccagca     600
tttggtatag gagggattgc tagcatgcca ccactcacag ctgttgctcc tgtgccaatg     660
ggctccattc cagttgttgg aatgtctcca cccttagtat cttctgtccc tccagcagca     720
gtgcctcccc tggctaacgg ggctcctccc gtcatacagc ctctgcctgc gtttgcgcat     780
cctgcagcca catggccaaa gagttcttcc ttcagcagat ctggtccagg gtcacaatta     840
aacactaagt tacagaaggc acaatcattc gatgtcgcca gcgcccctcc agcagcagaa     900
```

```
tgggctgtgc ctcagtcatc aaggctgaaa tacaggcagt tattcaacag ccacgacaaa     960
actatgagtg gacacttaac aggtccccag gcaagaacta ttctcatgca atcaagttta    1020
ccccaggctc agctggcttc aatatggaat ctttctgaca ttgatcaaga tggaaaactc    1080
actgcagaag aatttatcct agctatgcac ctaattgatg ttgccatgtc tggtcagcca    1140
ctgccgcccg tcctgcctcc agaatacatc cctccttcct tcagaagagt tcgctccggc    1200
agtgggatgt ccgtcataag ctcttcttct gtggatcaga ggctgcctga ggagccgtcg    1260
tcagaggatg agcagcagcc agagaagaaa ctgcctgtga catttgaaga taagaagcgg    1320
gagaacttcg agcgaggcag tgtggagctg agaagcgcc gccaagcgct cttggagcag    1380
cagcgcaaag agcaggagcg gttggctcag ctggagcgcg ccgagcagga gaggaaagag    1440
cgggagcgcc aggagcagga ggccaagcgg cagctggagc tggagaagca gctggagaag    1500
cagcgggagc tggagcggca gcgagaggag gagaggagga aggagatcga gaggcgcgag    1560
gccgcaaaac gggaactgga aaggcagcga caacttgaat gggaacggaa ccggagacag    1620
gaactcctga atcagaggaa caaggagcag gagggcaccg tggtcctgaa ggcaaggagg    1680
aagactctgg agtttgagtt agaagctctg aatgacaaaa agcatcagct agaaggaaaa    1740
cttcaggata tcaggtgtcg actggcaacc cagaggcaag aaattgagag cacgaacaag    1800
tctagagagc taagaattgc tgaaatcacc cacttacagc agcagttgca ggaatctcag    1860
caaatgcttg gaagacttat tccagagaaa cagatactca gtgaccagtt aaaacaagtc    1920
cagcagaaca gtttgcatag agactcgctt cttaccctca aaagagcctt ggaagcaaag    1980
gagctggccc ggcagcagct ccgggagcag ctggacgagg tggagagaga gaccaggtca    2040
aagctgcagg agattgatgt tttcaacaac cagctgaagg aactgagaga gatacatagc    2100
aaacagcaac tccagaagca gaggtccctg gaggcagcgc gactgaagca gaaagagcag    2160
gagaggaaga gcctggagtt agagaagcaa aaggaagacg ctcagagacg agttcaggaa    2220
agggacaagc aatggctgga gcatgtgcag caggaggagc agccacgccc ccggaaaccc    2280
cacgaggagg acagactgaa gagggaagac agtgtcagga agaaggaggc ggaagagaga    2340
gccaagccgg aaatgcaaga caagcagagt cggcttttcc atccgcatca ggagccagct    2400
aagctggcca cccaggcacc ctggtctacc acagagaaag gcccgcttac catttctgca    2460
caggagagtg taaaagtggt atattaccga gcgctgtacc cctttgaatc cagaagtcac    2520
gatgagatca ccatccagcc aggagatata gtcatggtgg atgaaagcca gactggagag    2580
ccaggatggc ttgaggagga gctgaaaggg aagacgggat ggttccctgc aaactatgca    2640
gaaaagattc cagaaaatga ggttcccact ccagccaaac cagtgaccga tctgacatct    2700
gccccctgccc ccaaactggc tctgcgtgag acccctgctc ctttgccagt gacctcttct    2760
gagccctcca accccccaa caactgggca gacttcagtt ccacgtggcc cagcagctca    2820
aacgagaagc cagaaacgga caactgggat acgtgggcgg ctcagccttc tctgaccgta    2880
cctagtgctg gccagttacg gcagagatca gcctttaccc cagccacagc cactggctcc    2940
tccccatctc ccgtcctggg ccaggtgaa aggtggaag gctacaagc gcaagccctg    3000
tatccctgga gagccaaaaa agacaaccac ttaaatttta acaaaagtga cgtcatcacc    3060
gttctggaac agcaagacat gtggtggttt ggagaagttc aaggtcagaa gggttggttc    3120
cccaagtctt acgtgaaact catttcaggg cccgtaagga atccacaag catcgatact    3180
ggccctactg aaagtcctgc tagtctaaag agagtggctt ccccggccgc caagccagcc    3240
attcccggag aagagtttat tgccatgtac acatacgaga gttctgagca aggagattta    3300
```

-continued

```
accttttcagc aaggggatgt gattgtggtt accaagaaag atggtgactg gtggacggga    3360
acggtgggcg acaagtccgg agtcttccct tctaactatg tgaggcttaa agattcagag    3420
ggctctggaa ctgctgggaa aacagggagt ttaggaaaaa aacctgaaat tgcccaggtt    3480
attgcttcct acgctgctac tggtcccgaa caactcaccc tggctcctgg gcagctgatt    3540
ctgatccgga aaaagaaccc aggtggatgg tgggaaggag aactgcaagc tcgagggaaa    3600
aagcgccaga tagggtggtt tccagcaaat tatgtcaaac ttctaagccc cggaacaagc    3660
aaaatcaccc caactgagct acccaagacc gcagtgcagc cagcagtgtg ccaggtgatc    3720
gggatgtacg attacaccgc ccagaacgat gacgaactag ccttcagcaa aggccagatc    3780
atcaacgtcc tcaacaagga ggaccccgac tggtggaaag gagaagtcag tgggcaagtt    3840 ggctcttcc catccaatta tgtaaagctg accacagaca tggaccccag ccagcaatga    3900
atcatatgtt gtccatcccc ccctcaggct tgaaagtcct caaagagacc cactatccca    3960
tatcactgcc cagagggatg atgggagatg cagccttgat catgtgactt gcagcatgat    4020 caactgtag cttctgagta aagaactca ctgcagagca gtttacctca tttgacctta    4080
gttgcatgtg atcgaaatgt ctgagtcact gcgtgcagag cagaagcaa attgcagaac    4140 tgcacagggt ggtgggtcct ttgggggctt tcctagtcac tcagactgac cggccccgcc    4200
ttcacacggg cgctttcaat agttttaaga ttattttttaa atgtgtattt tagccttta    4260 ataaaaatct caatcaatta cttctttgcc tattttggtt ttacaaaaac acccactatc    4320
aaggagtgcc tgtctgcgga cgattaaaat gctgttccgg gcgtaccgta aactgagagc    4380
ttgctgtacc tttgccgttt gtccagtgtt cccaaccaca ttgtgtagtt tggggctgtt    4440
ccctgccgta gagcacagag gagatgggtg tacctgtttt gaaaatgtgt atgtagactg    4500
agcctgacta tggaaggggt tatgcttgtc tgtgaccatc acgtgtacct gtcgcgcatg    4560
taccatctgt accgaagaag tagctcttcc tccatggcta aacccaccac cgtgtacagt    4620
gctctcatct actgcattca ttttactttg cacagtgacc ttgtagccac ctgaggaagc    4680
acccatgttt ccgtttggtc tcagatgtac ctagttgtgc ccgtgttttg ttttatttt    4740 tcaatctggc atgtcttcac accataaact agtaagacgc caactgccca ggcggttacg    4800
atcatcagta cccaccgtct tagtctctgt tacgtgaagt ttattccagt tgcttttat    4860 ggaatatctt gaacaagtaa tcttcttgac aagaaagaat gtatagaagt ctccctgcaa    4920
ttaatttccc agtgtttaca ttttttaact agactgtggg ggttgctaca gattaatatg    4980
aaatggcgct cctggtccgt gtgtgtgtta acttgtgctg tagctgaagc cgtgtgtcct    5040
tagatattag ttggaagtcg ggaagagaat tcgatatcaa gctt                     5084
```

<210> SEQ ID NO 2
<211> LENGTH: 3642
<212> TYPE: DNA
<213> ORGANISM: Mus musculus
<220> FEATURE:
<221> NAME/KEY: CDS
<222> LOCATION: (1)..(3642)
<223> OTHER INFORMATION: Mouse Esel

<400> SEQUENCE: 2

```
atg gct cag ttt ccc aca cct ttc ggt ggt agc ctg gat gtc tgg gcc    48
Met Ala Gln Phe Pro Thr Pro Phe Gly Gly Ser Leu Asp Val Trp Ala
1               5                  10                  15 ata act gtg gag gaa agg gcc aag cat gac cag cag ttc ctt agc ctg    96
Ile Thr Val Glu Glu Arg Ala Lys His Asp Gln Gln Phe Leu Ser Leu
```

```
                   20                  25                  30
aag ccg ata gcg gga ttt att act ggt gat caa gcg agg aac ttt ttt         144
Lys Pro Ile Ala Gly Phe Ile Thr Gly Asp Gln Ala Arg Asn Phe Phe
         35                  40                  45 ttc caa tct ggg tta cct cag cct gtc tta gca caa ata tgg gcg cta         192
Phe Gln Ser Gly Leu Pro Gln Pro Val Leu Ala Gln Ile Trp Ala Leu
     50                  55                  60 gcg gac atg aat aac gat gga agg atg gat caa gtg gaa ttt tcc ata         240
Ala Asp Met Asn Asn Asp Gly Arg Met Asp Gln Val Glu Phe Ser Ile
 65                  70                  75                  80 gcc atg aag ctt atc aaa ctg aag cta caa gga tat cag ctc ccc tcc         288
Ala Met Lys Leu Ile Lys Leu Lys Leu Gln Gly Tyr Gln Leu Pro Ser
                 85                  90                  95 aca ctt ccc cct gtc atg aaa cag caa cca gtg gct att tcc agt gca         336
Thr Leu Pro Pro Val Met Lys Gln Gln Pro Val Ala Ile Ser Ser Ala
             100                 105                 110 cca gca ttt ggt ata gga ggg att gct agc atg cca cca ctc aca gct         384
Pro Ala Phe Gly Ile Gly Gly Ile Ala Ser Met Pro Pro Leu Thr Ala
         115                 120                 125 gtt gct cct gtg cca atg ggc tcc att cca gtt gtt gga atg tct cca         432
Val Ala Pro Val Pro Met Gly Ser Ile Pro Val Val Gly Met Ser Pro
     130                 135                 140 ccc tta gta tct tct gtc cct cca gca gca gtg cct ccc ctg gct aac         480
Pro Leu Val Ser Ser Val Pro Pro Ala Ala Val Pro Pro Leu Ala Asn
145                 150                 155                 160 ggg gct cct ccc gtc ata cag cct ctg cct gcg ttt gcg cat cct gca         528
Gly Ala Pro Pro Val Ile Gln Pro Leu Pro Ala Phe Ala His Pro Ala
                165                 170                 175 gcc aca tgg cca aag agt tct tcc ttc agc aga tct ggt cca ggg tca         576
Ala Thr Trp Pro Lys Ser Ser Ser Phe Ser Arg Ser Gly Pro Gly Ser
            180                 185                 190 caa tta aac act aag tta cag aag gca caa tca ttc gat gtc gcc agc         624
Gln Leu Asn Thr Lys Leu Gln Lys Ala Gln Ser Phe Asp Val Ala Ser
        195                 200                 205 gcc cct cca gca gca gaa tgg gct gtg cct cag tca tca agg ctg aaa         672
Ala Pro Pro Ala Ala Glu Trp Ala Val Pro Gln Ser Ser Arg Leu Lys
    210                 215                 220 tac agg cag tta ttc aac agc cac gac aaa act atg agt gga cac tta         720
Tyr Arg Gln Leu Phe Asn Ser His Asp Lys Thr Met Ser Gly His Leu
225                 230                 235                 240 aca ggt ccc cag gca aga act att ctc atg caa tca agt tta ccc cag         768
Thr Gly Pro Gln Ala Arg Thr Ile Leu Met Gln Ser Ser Leu Pro Gln
                245                 250                 255 gct cag ctg gct tca ata tgg aat ctt tct gac att gat caa gat gga         816
Ala Gln Leu Ala Ser Ile Trp Asn Leu Ser Asp Ile Asp Gln Asp Gly
            260                 265                 270 aaa ctc act gca gaa gaa ttt atc cta gct atg cac cta att gat gtt         864
Lys Leu Thr Ala Glu Glu Phe Ile Leu Ala Met His Leu Ile Asp Val
        275                 280                 285 gcc atg tct ggt cag cca ctg ccg ccc gtc ctg cct cca gaa tac atc         912
Ala Met Ser Gly Gln Pro Leu Pro Pro Val Leu Pro Pro Glu Tyr Ile
    290                 295                 300 cct cct tcc ttc aga aga gtt cgc tcc ggc agt ggg atg tcc gtc ata         960
Pro Pro Ser Phe Arg Arg Val Arg Ser Gly Ser Gly Met Ser Val Ile
305                 310                 315                 320 agc tct tct tct gtg gat cag agg ctg cct gag gag ccg tcg tca gag        1008
Ser Ser Ser Ser Val Asp Gln Arg Leu Pro Glu Glu Pro Ser Ser Glu
                325                 330                 335 gat gag cag cag cca gag aag aaa ctg cct gtg aca ttt gaa gat aag        1056
```

```
                     Asp Glu Gln Gln Pro Glu Lys Lys Leu Pro Val Thr Phe Glu Asp Lys
                                 340             345             350 aag cgg gag aac ttc gag cga ggc agt gtg gag ctg gag aag cgc cgc                   1104
Lys Arg Glu Asn Phe Glu Arg Gly Ser Val Glu Leu Glu Lys Arg Arg
            355             360             365 caa gcg ctc ttg gag cag cag cgc aaa gag cag gag cgg ttg gct cag                   1152
Gln Ala Leu Leu Glu Gln Gln Arg Lys Glu Gln Glu Arg Leu Ala Gln
370             375             380 ctg gag cgc gcc gag cag gag agg aaa gag cgg gag cgc cag gag cag                   1200
Leu Glu Arg Ala Glu Gln Glu Arg Lys Glu Arg Glu Arg Gln Glu Gln
385             390             395             400 gag gcc aag cgg cag ctg gag ctg gag aag cag ctg gag aag cag cgg                   1248
Glu Ala Lys Arg Gln Leu Glu Leu Glu Lys Gln Leu Glu Lys Gln Arg
                405             410             415 gag ctg gag cgg cag cga gag gag gag agg agg aag gag atc gag agg                   1296
Glu Leu Glu Arg Gln Arg Glu Glu Glu Arg Arg Lys Glu Ile Glu Arg
            420             425             430 cgc gag gcc gca aaa cgg gaa ctg gaa agg cag cga caa ctt gaa tgg                   1344
Arg Glu Ala Ala Lys Arg Glu Leu Glu Arg Gln Arg Gln Leu Glu Trp
                435             440             445 gaa cgg aac cgg aga cag gaa ctc ctg aat cag agg aac aag gag cag                   1392
Glu Arg Asn Arg Arg Gln Glu Leu Leu Asn Gln Arg Asn Lys Glu Gln
            450             455             460 gag ggc acc gtg gtc ctg aag gca agg agg aag act ctg gag ttt gag                   1440
Glu Gly Thr Val Val Leu Lys Ala Arg Arg Lys Thr Leu Glu Phe Glu
465             470             475             480 tta gaa gct ctg aat gac aaa aag cat cag cta gaa gga aaa ctt cag                   1488
Leu Glu Ala Leu Asn Asp Lys Lys His Gln Leu Glu Gly Lys Leu Gln
                485             490             495 gat atc agg tgt cga ctg gca acc cag agg caa gaa att gag agc acg                   1536
Asp Ile Arg Cys Arg Leu Ala Thr Gln Arg Gln Glu Ile Glu Ser Thr
            500             505             510 aac aag tct aga gag cta aga att gct gaa atc acc cac tta cag cag                   1584
Asn Lys Ser Arg Glu Leu Arg Ile Ala Glu Ile Thr His Leu Gln Gln
                515             520             525 cag ttg cag gaa tct cag caa atg ctt gga aga ctt att cca gag aaa                   1632
Gln Leu Gln Glu Ser Gln Gln Met Leu Gly Arg Leu Ile Pro Glu Lys
530             535             540 cag ata ctc agt gac cag tta aaa caa gtc cag cag aac agt ttg cat                   1680
Gln Ile Leu Ser Asp Gln Leu Lys Gln Val Gln Gln Asn Ser Leu His
545             550             555             560 aga gac tcg ctt ctt acc ctc aaa aga gcc ttg gaa gca aag gag ctg                   1728
Arg Asp Ser Leu Leu Thr Leu Lys Arg Ala Leu Glu Ala Lys Glu Leu
                565             570             575 gcc cgg cag cag ctc cgg gag cag ctg gac gag gtg gag aga gag acc                   1776
Ala Arg Gln Gln Leu Arg Glu Gln Leu Asp Glu Val Glu Arg Glu Thr
            580             585             590 agg tca aag ctg cag gag att gat gtt ttc aac aac cag ctg aag gaa                   1824
Arg Ser Lys Leu Gln Glu Ile Asp Val Phe Asn Asn Gln Leu Lys Glu
                595             600             605 ctg aga gag ata cat agc aaa cag caa ctc cag aag cag agg tcc ctg                   1872
Leu Arg Glu Ile His Ser Lys Gln Gln Leu Gln Lys Gln Arg Ser Leu
            610             615             620 gag gca gcg cga ctg aag cag aaa gag cag gag agg aag agc ctg gag                   1920
Glu Ala Ala Arg Leu Lys Gln Lys Glu Gln Glu Arg Lys Ser Leu Glu
625             630             635             640 tta gag aag caa aag gaa gac gct cag aga cga gtt cag gaa agg gac                   1968
Leu Glu Lys Gln Lys Glu Asp Ala Gln Arg Arg Val Gln Glu Arg Asp
                645             650             655
```

```
                                              -continued aag caa tgg ctg gag cat gtg cag cag gag gag cag cca cgc ccc cgg        2016
Lys Gln Trp Leu Glu His Val Gln Gln Glu Glu Gln Pro Arg Pro Arg
            660                 665                 670 aaa ccc cac gag gag gac aga ctg aag agg gaa gac agt gtc agg aag        2064
Lys Pro His Glu Glu Asp Arg Leu Lys Arg Glu Asp Ser Val Arg Lys
675                 680                 685 aag gag gcg gaa gag aga gcc aag ccg gaa atg caa gac aag cag agt        2112
Lys Glu Ala Glu Glu Arg Ala Lys Pro Glu Met Gln Asp Lys Gln Ser
        690                 695                 700 cgg ctt ttc cat ccg cat cag gag cca gct aag ctg gcc acc cag gca        2160
Arg Leu Phe His Pro His Gln Glu Pro Ala Lys Leu Ala Thr Gln Ala
705                 710                 715                 720 ccc tgg tct acc aca gag aaa ggc ccg ctt acc att tct gca cag gag        2208
Pro Trp Ser Thr Thr Glu Lys Gly Pro Leu Thr Ile Ser Ala Gln Glu
                725                 730                 735 agt gta aaa gtg gta tat tac cga gcg ctg tac ccc ttt gaa tcc aga        2256
Ser Val Lys Val Val Tyr Tyr Arg Ala Leu Tyr Pro Phe Glu Ser Arg
            740                 745                 750 agt cac gat gag atc acc atc cag cca gga gat ata gtc atg gtg gat        2304
Ser His Asp Glu Ile Thr Ile Gln Pro Gly Asp Ile Val Met Val Asp
        755                 760                 765 gaa agc cag act gga gag cca gga tgg ctt gga gga gag ctg aaa ggg        2352
Glu Ser Gln Thr Gly Glu Pro Gly Trp Leu Gly Gly Glu Leu Lys Gly
770                 775                 780 aag acg gga tgg ttc cct gca aac tat gca gaa aag att cca gaa aat        2400
Lys Thr Gly Trp Phe Pro Ala Asn Tyr Ala Glu Lys Ile Pro Glu Asn
785                 790                 795                 800 gag gtt ccc act cca gcc aaa cca gtg acc gat ctg aca tct gcc cct        2448
Glu Val Pro Thr Pro Ala Lys Pro Val Thr Asp Leu Thr Ser Ala Pro
                805                 810                 815 gcc ccc aaa ctg gct ctg cgt gag acc cct gct cct ttg cca gtg acc        2496
Ala Pro Lys Leu Ala Leu Arg Glu Thr Pro Ala Pro Leu Pro Val Thr
            820                 825                 830 tct tct gag ccc tcc aca acc ccc aac aac tgg gca gac ttc agt tcc        2544
Ser Ser Glu Pro Ser Thr Thr Pro Asn Asn Trp Ala Asp Phe Ser Ser
        835                 840                 845 acg tgg ccc agc agc tca aac gag aag cca gaa acg gac aac tgg gat        2592
Thr Trp Pro Ser Ser Ser Asn Glu Lys Pro Glu Thr Asp Asn Trp Asp
850                 855                 860 acg tgg gcg gct cag cct tct ctg acc gta cct agt gct ggc cag tta        2640
Thr Trp Ala Ala Gln Pro Ser Leu Thr Val Pro Ser Ala Gly Gln Leu
865                 870                 875                 880 cgg cag aga tca gcc ttt acc cca gcc aca gcc act ggc tcc tcc cca        2688
Arg Gln Arg Ser Ala Phe Thr Pro Ala Thr Ala Thr Gly Ser Ser Pro
                885                 890                 895 tct ccc gtc ctg ggc cag ggt gaa aag gtg gaa ggg cta caa gcg caa        2736
Ser Pro Val Leu Gly Gln Gly Glu Lys Val Glu Gly Leu Gln Ala Gln
            900                 905                 910 gcc ctg tat ccc tgg aga gcc aaa aaa gac aac cac tta aat ttt aac        2784
Ala Leu Tyr Pro Trp Arg Ala Lys Lys Asp Asn His Leu Asn Phe Asn
        915                 920                 925 aaa agt gac gtc atc acc gtt ctg gaa cag caa gac atg tgg tgg ttt        2832
Lys Ser Asp Val Ile Thr Val Leu Glu Gln Gln Asp Met Trp Trp Phe
930                 935                 940 gga gaa gtt caa ggt cag aag ggt tgg ttc ccc aag tct tac gtg aaa        2880
Gly Glu Val Gln Gly Gln Lys Gly Trp Phe Pro Lys Ser Tyr Val Lys
945                 950                 955                 960 ctc att tca ggg ccc gta agg aaa tcc aca agc atc gat act ggc cct        2928
Leu Ile Ser Gly Pro Val Arg Lys Ser Thr Ser Ile Asp Thr Gly Pro
                965                 970                 975
```

| | | |
|---|---|---|
| act gaa agt cct gct agt cta aag aga gtg gct tcc ccg gcc gcc aag<br>Thr Glu Ser Pro Ala Ser Leu Lys Arg Val Ala Ser Pro Ala Ala Lys<br>980 985 990 | 2976 | |
| cca gcc att ccc gga gaa gag ttt att gcc atg tac aca tac gag agt<br>Pro Ala Ile Pro Gly Glu Glu Phe Ile Ala Met Tyr Thr Tyr Glu Ser<br>995 1000 1005 | 3024 | |
| tct gag caa gga gat tta acc ttt cag caa ggg gat gtg att gtg<br>Ser Glu Gln Gly Asp Leu Thr Phe Gln Gln Gly Asp Val Ile Val<br>1010 1015 1020 | 3069 | |
| gtt acc aag aaa gat ggt gac tgg tgg acg gga acg gtg ggc gac<br>Val Thr Lys Lys Asp Gly Asp Trp Trp Thr Gly Thr Val Gly Asp<br>1025 1030 1035 | 3114 | |
| aag tcc gga gtc ttc cct tct aac tat gtg agg ctt aaa gat tca<br>Lys Ser Gly Val Phe Pro Ser Asn Tyr Val Arg Leu Lys Asp Ser<br>1040 1045 1050 | 3159 | |
| gag ggc tct gga act gct ggg aaa aca ggg agt tta gga aaa aaa<br>Glu Gly Ser Gly Thr Ala Gly Lys Thr Gly Ser Leu Gly Lys Lys<br>1055 1060 1065 | 3204 | |
| cct gaa att gcc cag gtt att gct tcc tac gct gct act ggt ccc<br>Pro Glu Ile Ala Gln Val Ile Ala Ser Tyr Ala Ala Thr Gly Pro<br>1070 1075 1080 | 3249 | |
| gaa caa ctc acc ctg gct cct ggg cag ctg att ctg atc cgg aaa<br>Glu Gln Leu Thr Leu Ala Pro Gly Gln Leu Ile Leu Ile Arg Lys<br>1085 1090 1095 | 3294 | |
| aag aac cca ggt gga tgg tgg gaa gga gaa ctg caa gct cga ggg<br>Lys Asn Pro Gly Gly Trp Trp Glu Gly Glu Leu Gln Ala Arg Gly<br>1100 1105 1110 | 3339 | |
| aaa aag cgc cag ata ggg tgg ttt cca gca aat tat gtc aaa ctt<br>Lys Lys Arg Gln Ile Gly Trp Phe Pro Ala Asn Tyr Val Lys Leu<br>1115 1120 1125 | 3384 | |
| cta agc ccc gga aca agc aaa atc acc cca act gag cta ccc aag<br>Leu Ser Pro Gly Thr Ser Lys Ile Thr Pro Thr Glu Leu Pro Lys<br>1130 1135 1140 | 3429 | |
| acc gca gtg cag cca gca gtg tgc cag gtg atc ggg atg tac gat<br>Thr Ala Val Gln Pro Ala Val Cys Gln Val Ile Gly Met Tyr Asp<br>1145 1150 1155 | 3474 | |
| tac acc gcc cag aac gat gac gaa cta gcc ttc agc aaa ggc cag<br>Tyr Thr Ala Gln Asn Asp Asp Glu Leu Ala Phe Ser Lys Gly Gln<br>1160 1165 1170 | 3519 | |
| atc atc aac gtc ctc aac aag gag gac ccg gac tgg tgg aaa gga<br>Ile Ile Asn Val Leu Asn Lys Glu Asp Pro Asp Trp Trp Lys Gly<br>1175 1180 1185 | 3564 | |
| gaa gtc agt ggg caa gtt ggg ctc ttc cca tcc aat tat gta aag<br>Glu Val Ser Gly Gln Val Gly Leu Phe Pro Ser Asn Tyr Val Lys<br>1190 1195 1200 | 3609 | |
| ctg acc aca gac atg gac ccc agc cag caa tga<br>Leu Thr Thr Asp Met Asp Pro Ser Gln Gln<br>1205 1210 | 3642 | |

<210> SEQ ID NO 3
<211> LENGTH: 1213
<212> TYPE: PRT
<213> ORGANISM: Mus musculus

<400> SEQUENCE: 3

Met Ala Gln Phe Pro Thr Pro Phe Gly Gly Ser Leu Asp Val Trp Ala
1               5                   10                  15

Ile Thr Val Glu Glu Arg Ala Lys His Asp Gln Gln Phe Leu Ser Leu
            20                  25                  30

-continued

```
Lys Pro Ile Ala Gly Phe Ile Thr Gly Asp Gln Ala Arg Asn Phe Phe
             35                  40                  45

Phe Gln Ser Gly Leu Pro Gln Pro Val Leu Ala Gln Ile Trp Ala Leu
         50                  55                  60

Ala Asp Met Asn Asn Asp Gly Arg Met Asp Gln Val Glu Phe Ser Ile
 65                  70                  75                  80

Ala Met Lys Leu Ile Lys Leu Lys Leu Gln Gly Tyr Gln Leu Pro Ser
                 85                  90                  95

Thr Leu Pro Pro Val Met Lys Gln Gln Pro Val Ala Ile Ser Ser Ala
             100                 105                 110

Pro Ala Phe Gly Ile Gly Gly Ile Ala Ser Met Pro Pro Leu Thr Ala
             115                 120                 125

Val Ala Pro Val Pro Met Gly Ser Ile Pro Val Val Gly Met Ser Pro
    130                 135                 140

Pro Leu Val Ser Ser Val Pro Pro Ala Ala Val Pro Pro Leu Ala Asn
145                 150                 155                 160

Gly Ala Pro Pro Val Ile Gln Pro Leu Pro Ala Phe Ala His Pro Ala
                165                 170                 175

Ala Thr Trp Pro Lys Ser Ser Ser Phe Ser Arg Ser Gly Pro Gly Ser
            180                 185                 190

Gln Leu Asn Thr Lys Leu Gln Lys Ala Gln Ser Phe Asp Val Ala Ser
        195                 200                 205

Ala Pro Pro Ala Ala Glu Trp Ala Val Pro Gln Ser Ser Arg Leu Lys
    210                 215                 220

Tyr Arg Gln Leu Phe Asn Ser His Asp Lys Thr Met Ser Gly His Leu
225                 230                 235                 240

Thr Gly Pro Gln Ala Arg Thr Ile Leu Met Gln Ser Ser Leu Pro Gln
                245                 250                 255

Ala Gln Leu Ala Ser Ile Trp Asn Leu Ser Asp Ile Asp Gln Asp Gly
            260                 265                 270

Lys Leu Thr Ala Glu Glu Phe Ile Leu Ala Met His Leu Ile Asp Val
        275                 280                 285

Ala Met Ser Gly Gln Pro Leu Pro Pro Val Leu Pro Pro Glu Tyr Ile
    290                 295                 300

Pro Pro Ser Phe Arg Arg Val Arg Ser Gly Ser Gly Met Ser Val Ile
305                 310                 315                 320

Ser Ser Ser Ser Val Asp Gln Arg Leu Pro Glu Glu Pro Ser Ser Glu
                325                 330                 335

Asp Glu Gln Gln Pro Glu Lys Lys Leu Pro Val Thr Phe Glu Asp Lys
            340                 345                 350

Lys Arg Glu Asn Phe Glu Arg Gly Ser Val Glu Leu Glu Lys Arg Arg
        355                 360                 365

Gln Ala Leu Leu Glu Gln Gln Arg Lys Glu Gln Glu Arg Leu Ala Gln
    370                 375                 380

Leu Glu Arg Ala Glu Gln Glu Arg Lys Glu Arg Glu Arg Gln Glu Gln
385                 390                 395                 400

Glu Ala Lys Arg Gln Leu Glu Leu Glu Lys Gln Leu Glu Lys Gln Arg
                405                 410                 415

Glu Leu Glu Arg Gln Arg Glu Glu Arg Lys Glu Ile Glu Arg
            420                 425                 430

Arg Glu Ala Ala Lys Arg Glu Leu Glu Arg Gln Arg Gln Leu Glu Trp
    435                 440                 445

Glu Arg Asn Arg Arg Gln Glu Leu Leu Asn Gln Arg Asn Lys Glu Gln
```

-continued

```
            450                 455                 460
Glu Gly Thr Val Val Leu Lys Ala Arg Arg Lys Thr Leu Glu Phe Glu
465                 470                 475                 480

Leu Glu Ala Leu Asn Asp Lys Lys His Gln Leu Glu Gly Lys Leu Gln
                485                 490                 495

Asp Ile Arg Cys Arg Leu Ala Thr Gln Arg Gln Glu Ile Glu Ser Thr
            500                 505                 510

Asn Lys Ser Arg Glu Leu Arg Ile Ala Glu Ile Thr His Leu Gln Gln
        515                 520                 525

Gln Leu Gln Glu Ser Gln Gln Met Leu Gly Arg Leu Ile Pro Glu Lys
        530                 535                 540

Gln Ile Leu Ser Asp Gln Leu Lys Gln Val Gln Gln Asn Ser Leu His
545                 550                 555                 560

Arg Asp Ser Leu Leu Thr Leu Lys Arg Ala Leu Glu Ala Lys Glu Leu
                565                 570                 575

Ala Arg Gln Gln Leu Arg Glu Gln Leu Asp Glu Val Glu Arg Glu Thr
                580                 585                 590

Arg Ser Lys Leu Gln Glu Ile Asp Val Phe Asn Asn Gln Leu Lys Glu
        595                 600                 605

Leu Arg Glu Ile His Ser Lys Gln Gln Leu Gln Lys Gln Arg Ser Leu
        610                 615                 620

Glu Ala Ala Arg Leu Lys Gln Lys Glu Gln Glu Arg Lys Ser Leu Glu
625                 630                 635                 640

Leu Glu Lys Gln Lys Glu Asp Ala Gln Arg Arg Val Gln Glu Arg Asp
                645                 650                 655

Lys Gln Trp Leu Glu His Val Gln Gln Glu Gln Pro Arg Pro Arg
                660                 665                 670

Lys Pro His Glu Glu Asp Arg Leu Lys Arg Glu Asp Ser Val Arg Lys
        675                 680                 685

Lys Glu Ala Glu Glu Arg Ala Lys Pro Glu Met Gln Asp Lys Gln Ser
        690                 695                 700

Arg Leu Phe His Pro His Gln Glu Pro Ala Lys Leu Ala Thr Gln Ala
705                 710                 715                 720

Pro Trp Ser Thr Thr Glu Lys Gly Pro Leu Thr Ile Ser Ala Gln Glu
                725                 730                 735

Ser Val Lys Val Val Tyr Tyr Arg Ala Leu Tyr Pro Phe Glu Ser Arg
                740                 745                 750

Ser His Asp Glu Ile Thr Ile Gln Pro Gly Asp Ile Val Met Val Asp
        755                 760                 765

Glu Ser Gln Thr Gly Glu Pro Gly Trp Leu Gly Gly Glu Leu Lys Gly
        770                 775                 780

Lys Thr Gly Trp Phe Pro Ala Asn Tyr Ala Glu Lys Ile Pro Glu Asn
785                 790                 795                 800

Glu Val Pro Thr Pro Ala Lys Pro Val Thr Asp Leu Thr Ser Ala Pro
                805                 810                 815

Ala Pro Lys Leu Ala Leu Arg Glu Thr Pro Ala Pro Leu Pro Val Thr
                820                 825                 830

Ser Ser Glu Pro Ser Thr Thr Pro Asn Asn Trp Ala Asp Phe Ser Ser
        835                 840                 845

Thr Trp Pro Ser Ser Ser Asn Glu Lys Pro Glu Thr Asp Asn Trp Asp
        850                 855                 860

Thr Trp Ala Ala Gln Pro Ser Leu Thr Val Pro Ser Ala Gly Gln Leu
865                 870                 875                 880
```

Arg Gln Arg Ser Ala Phe Thr Pro Ala Thr Ala Thr Gly Ser Ser Pro
            885                 890                 895

Ser Pro Val Leu Gly Gln Gly Glu Lys Val Glu Gly Leu Gln Ala Gln
            900                 905                 910

Ala Leu Tyr Pro Trp Arg Ala Lys Lys Asp Asn His Leu Asn Phe Asn
            915                 920                 925

Lys Ser Asp Val Ile Thr Val Leu Glu Gln Gln Asp Met Trp Trp Phe
    930                 935                 940

Gly Glu Val Gln Gly Gln Lys Gly Trp Phe Pro Lys Ser Tyr Val Lys
945                 950                 955                 960

Leu Ile Ser Gly Pro Val Arg Lys Ser Thr Ser Ile Asp Thr Gly Pro
            965                 970                 975

Thr Glu Ser Pro Ala Ser Leu Lys Arg Val Ala Ser Pro Ala Ala Lys
            980                 985                 990

Pro Ala Ile Pro Gly Glu Glu Phe Ile Ala Met Tyr Thr Tyr Glu Ser
            995                 1000                1005

Ser Glu Gln Gly Asp Leu Thr Phe Gln Gln Gly Asp Val Ile Val
            1010                1015                1020

Val Thr Lys Lys Asp Gly Asp Trp Trp Thr Gly Thr Val Gly Asp
            1025                1030                1035

Lys Ser Gly Val Phe Pro Ser Asn Tyr Val Arg Leu Lys Asp Ser
            1040                1045                1050

Glu Gly Ser Gly Thr Ala Gly Lys Thr Gly Ser Leu Gly Lys Lys
            1055                1060                1065

Pro Glu Ile Ala Gln Val Ile Ala Ser Tyr Ala Ala Thr Gly Pro
            1070                1075                1080

Glu Gln Leu Thr Leu Ala Pro Gly Gln Leu Ile Leu Ile Arg Lys
            1085                1090                1095

Lys Asn Pro Gly Gly Trp Trp Glu Gly Glu Leu Gln Ala Arg Gly
            1100                1105                1110

Lys Lys Arg Gln Ile Gly Trp Phe Pro Ala Asn Tyr Val Lys Leu
            1115                1120                1125

Leu Ser Pro Gly Thr Ser Lys Ile Thr Pro Thr Glu Leu Pro Lys
            1130                1135                1140

Thr Ala Val Gln Pro Ala Val Cys Gln Val Ile Gly Met Tyr Asp
            1145                1150                1155

Tyr Thr Ala Gln Asn Asp Asp Glu Leu Ala Phe Ser Lys Gly Gln
            1160                1165                1170

Ile Ile Asn Val Leu Asn Lys Glu Asp Pro Asp Trp Trp Lys Gly
            1175                1180                1185

Glu Val Ser Gly Gln Val Gly Leu Phe Pro Ser Asn Tyr Val Lys
            1190                1195                1200

Leu Thr Thr Asp Met Asp Pro Ser Gln Gln
            1205                1210

<210> SEQ ID NO 4
<211> LENGTH: 4625
<212> TYPE: DNA
<213> ORGANISM: Mus musculus

<400> SEQUENCE: 4
cccttccttt cctttttttg tgttcgcctt cggccgtgcc ggctgagagc ccagcagccg     60
tgacaggctg cgcaacaggt tcgctgcggc cggcctgacg actgacccgg cggcggcggc    120

-continued

| | |
|---|---|
| cgcggcacgg cagggtcttc ccggagcttg gccgcgccca cgcgccggtg tcgaggagcg | 180 |
| cgcggggtcg cgccgggacg tgcgcgaggc gccagatggc tgagagctgc aagaagaagt | 240 |
| caggatcatg atggctcagt ttcccacagc gatgaatgga gggccaaata tgtgggctat | 300 |
| tacatctgaa gaacgtacta agcatgataa acagtttgat aacctcaaac cttcaggagg | 360 |
| ttacataaca ggtgatcaag cccgtacttt tttcctacag tcaggtctgc cggccccggt | 420 |
| tttagctgaa atatgggcct tatcagatct gaacaaggat gggaagatgg accagcaaga | 480 |
| gttctctata gctatgaaac tcatcaagtt aaagttgcag ggccaacagc tgcctgtagt | 540 |
| cctccctcct atcatgaaac aaccccctat gttctctcca ctaatctctg ctcgttttgg | 600 |
| gatgggaagc atgcccaatc tgtccattca tcagccattg cctccagttg cacctatagc | 660 |
| aacacccttg tcttctgcta cgtcagggac cagtattcct cccctaatga tgcctgctcc | 720 |
| cctagtgcct tctgttagta catcctcatt accaaatgga actgccagtc tcattcagcc | 780 |
| tttatccatt ccttattctt cttcaacatt gcctcatgca tcatcttaca gcctgatgat | 840 |
| gggaggattt ggtggtgcta gtatccagaa ggcccagtct ctgattgatt taggatctag | 900 |
| tagctcaact tcctcaactg cttccctctc agggaactca cctaagacag ggacctcaga | 960 |
| gtgggcagtt cctcagcctt caagattaaa gtatcggcaa aaatttaata gtctagacaa | 1020 |
| aggcatgagc ggatacctct caggttttca agctagaaat gcccttcttc agtcaaatct | 1080 |
| ctctcaaact cagctagcta ctatttggac tctggctgac atcgatggtg acggacagtt | 1140 |
| gaaagctgaa gaatttattc tggcgatgca cctcactgac atggccaaag ctggacagcc | 1200 |
| actaccactg acgttgcctc ccgagcttgt ccctccatct ttcagagggg gaaagcaagt | 1260 |
| tgattctgtt aatggaactc tgccttcata tcagaaaaca caagaagaag agcctcagaa | 1320 |
| gaaactgcca gttacttttg aggacaaacg gaaagccaac tatgaacgag gaaacatgga | 1380 |
| gctggagaag cgacgccaag tgttgatgga gcagcagcag agggaggctg aacgcaaagc | 1440 |
| ccagaaagag aaggaagagt gggagcggaa acagagagaa ctgcaagagc aagaatggaa | 1500 |
| gaagcagctg gagttggaga aacgcttgga gaaacagaga gagctggaga gacagcggga | 1560 |
| ggaagagagg agaaaggaga tagaaagacg agaggcagca aaacaggagc ttgagagaca | 1620 |
| acgccgttta gaatgggaaa gactccgtcg gcaggagctg ctcagtcaga agaccaggga | 1680 |
| acaagaagac attgtcaggc tgagctccag aaagaaaagt ctccacctgg aactggaagc | 1740 |
| agtgaatgga aaacatcagc agatctcagg cagactacaa gatgtccaaa tcagaaagca | 1800 |
| aacacaaaag actgagctag aagttttgga taaacagtgt gacctggaaa ttatggaaat | 1860 |
| caaacaactt caacaagagc ttaaggaata tcaaaataag cttatctatc tggtccctga | 1920 |
| gaagcagcta ttaaacgaaa gaattaaaaa catgcagctc agtaacacac ctgattcagg | 1980 |
| gatcagttta cttcataaaa agtcatcaga aaaggaagaa ttatgccaaa gacttaaaga | 2040 |
| acaattagat gctcttgaaa aagaaactgc atctaagctc tcagaatgg attcattaa | 2100 |
| caatcagctg aaggaactca gagaaagcta taatacacag cagttagccc ttgaacaact | 2160 |
| tcataaaatc aaacgtgaca aattgaagga atcgaaaga aaagattag agcaaattca | 2220 |
| aaaaagaaa ctagaagatg aggctgcaag gaaagcaaag caaggaaaag aaaacttgtg | 2280 |
| gagagaaagt attagaaagg aagaagagga aagcaaaaa cgactccagg aagaaaagtc | 2340 |
| acaggacaaa actcaagaag aggaacgaaa agctgaggca aaacaaagtg agacagccag | 2400 |
| tgctttggtg aattacagag cactgtaccc ttttgaagca agaaaccatg atgagatgag | 2460 |
| ttttagttct ggggatataa ttcaggttga tgaaaaaact gtaggagagc ctggttggct | 2520 |

```
ttatggtagt tttcagggaa agtttggctg gttcccctgc aactatgtag aaaaagtgct    2580
gtcaagtgaa aaagctctgt ctcctaagaa ggccttactt cctcctacag tgtctctctc    2640
tgctacctca acttcttccc agccaccagc atcagtgact gattatcaca atgtatcctt    2700
ctcaaacctt actgttaata caacatggca gcagaagtca gcttttaccc gcactgtgtc    2760
ccctggatct gtgtccccca ttcacggaca ggggcaggct gtagaaaacc tgaaagccca    2820 ggcccttttgt tcctggacgg caaagaagga gaaccacctg aacttctcaa agcacgacgt    2880
catcactgtc ctggagcagc aggaaaaactg gtggtttggg gaggtgcacg gaggaagagg    2940
atggttcccc aagtcttatg tcaagctcat tcctgggaat gaagtacagc gaggagagcc    3000
agaagctttg tatgcagctg tgactaagaa acctacctcc acagcctatc cagttacctc    3060
cacagcctat ccagttggag aagactacat tgcactttat tcatactcaa gtgtagagcc    3120
cggggatttg actttcactg aaggtgaaga aattctagtg acccagaaag atggagagtg    3180
gtggacagga agtattggag agagaactgg aatcttcccg tccaactacg tcagaccaaa    3240
ggatcaagag aattttggga atgctagcaa atctggagca tcaaacaaaa acccgagat    3300 cgctcaagta acttcagcat atgctgcttc agggactgag cagctcagcc ttgcgccagg    3360
acagttaata ttaatcttaa agaaaaacac aagcgggtgg tggcaaggag agctacaggc    3420
cagagggaag aaacgacaga agggatggtt tcctgccagc catgtaaagc tgctaggtcc    3480
aagcagtgaa agaaccatgc ctacttttca cgctgtatgt caagtgattg ctatgtatga    3540
ctacatggcg aataacgaag atgagctcaa tttctccaaa ggacagctga ttaatgttat    3600
gaacaaagat gaccctgact ggtggcaagg agaaaccaat ggtctgactg gtctctttcc    3660
ttcaaactat gttaagatga caacagactc agatccaagt caacagtggt gtgctgacct    3720
ccaagccctg gacacaatgc agcctacgga gaggaagcga cagggctaca ttcacgagct    3780
cattcagaca gaggagcgt acatggacga cctgcaactt tttgaacaaa aaactctcct    3840
ttgagggcct ggggaagcca gaaccagggg agctgcccac aaggctgggt ctaaagacag    3900
attttgctct cccaggacag aggagcatca catcggcttc atccatccaa acaagccaca    3960
ctcgctgggc ctggtatttt attgcaccac taaaattgct agcaatctat gcaaacatga    4020 tcttttaaa caaacgccac agcacagtgc cttgtactag tgttaacctg ttcagctgtg    4080
ttagatgcca gggtttccat tttcagggct ataaagtat tatgtgggaa atgagacatc    4140
agaccaccgg acgttaccac ttggcaaatc tgtccactgt ggagttggtg atgttggaac    4200
cattccacac tatgtgacct ctgctgggtc acacactcag gaggtgaagg gctgagatga    4260
aatgctgcag ccttggggct tgtgcagcct gatactgaaa tagcatccac ttgtgcactg    4320
aataaataga aacttgatcg tttttattctg actagatatt atcattctct gctaagacaa    4380
tatagtttga aatattatag tttgaatata aggaggaaag cttgatgtac tttaaatata    4440
ctgtgaactc taataatgtg gggatatttt tcaactttaa ttttcttaag tataaattat    4500
ttatgtaaat tctttgtttt gcatatttca tagaacatgc atctttaagc tttatcattg    4560
ccaacaatgt acagaaagag aataaaagta taagtttatg aatgtaaaaa aaaaaaaaaa    4620
aaaaa                                                                4625

<210> SEQ ID NO 5
<211> LENGTH: 3594
<212> TYPE: DNA
<213> ORGANISM: Mus musculus
<220> FEATURE:
```

```
<221> NAME/KEY: CDS
<222> LOCATION: (1)..(3594)
<223> OTHER INFORMATION: Mouse Ese2

<400> SEQUENCE: 5 atg gct cag ttt ccc aca gcg atg aat gga ggg cca aat atg tgg gct      48
Met Ala Gln Phe Pro Thr Ala Met Asn Gly Gly Pro Asn Met Trp Ala
1               5                   10                  15 att aca tct gaa gaa cgt act aag cat gat aaa cag ttt gat aac ctc      96
Ile Thr Ser Glu Glu Arg Thr Lys His Asp Lys Gln Phe Asp Asn Leu
            20                  25                  30 aaa cct tca gga ggt tac ata aca ggt gat caa gcc cgt act ttt ttc     144
Lys Pro Ser Gly Gly Tyr Ile Thr Gly Asp Gln Ala Arg Thr Phe Phe
        35                  40                  45 cta cag tca ggt ctg ccg gcc ccg gtt tta gct gaa ata tgg gcc tta     192
Leu Gln Ser Gly Leu Pro Ala Pro Val Leu Ala Glu Ile Trp Ala Leu
    50                  55                  60 tca gat ctg aac aag gat ggg aag atg gac cag caa gag ttc tct ata     240
Ser Asp Leu Asn Lys Asp Gly Lys Met Asp Gln Gln Glu Phe Ser Ile
65                  70                  75                  80 gct atg aaa ctc atc aag tta aag ttg cag ggc caa cag ctg cct gta     288
Ala Met Lys Leu Ile Lys Leu Lys Leu Gln Gly Gln Gln Leu Pro Val
                85                  90                  95 gtc ctc cct cct atc atg aaa caa ccc cct atg ttc tct cca cta atc     336
Val Leu Pro Pro Ile Met Lys Gln Pro Pro Met Phe Ser Pro Leu Ile
            100                 105                 110 tct gct cgt ttt ggg atg gga agc atg ccc aat ctg tcc att cat cag     384
Ser Ala Arg Phe Gly Met Gly Ser Met Pro Asn Leu Ser Ile His Gln
        115                 120                 125 cca ttg cct cca gtt gca cct ata gca aca ccc ttg tct tct gct acg     432
Pro Leu Pro Pro Val Ala Pro Ile Ala Thr Pro Leu Ser Ser Ala Thr
    130                 135                 140 tca ggg acc agt att cct ccc cta atg atg cct gct ccc cta gtg cct     480
Ser Gly Thr Ser Ile Pro Pro Leu Met Met Pro Ala Pro Leu Val Pro
145                 150                 155                 160 tct gtt agt aca tcc tca tta cca aat gga act gcc agt ctc att cag     528
Ser Val Ser Thr Ser Ser Leu Pro Asn Gly Thr Ala Ser Leu Ile Gln
                165                 170                 175 cct tta tcc att cct tat tct tct tca aca ttg cct cat gca tca tct     576
Pro Leu Ser Ile Pro Tyr Ser Ser Ser Thr Leu Pro His Ala Ser Ser
            180                 185                 190 tac agc ctg atg atg gga gga ttt ggt ggt gct agt atc cag aag gcc     624
Tyr Ser Leu Met Met Gly Gly Phe Gly Gly Ala Ser Ile Gln Lys Ala
        195                 200                 205 cag tct ctg att gat tta gga tct agt agc tca act tcc tca act gct     672
Gln Ser Leu Ile Asp Leu Gly Ser Ser Ser Ser Thr Ser Ser Thr Ala
    210                 215                 220 tcc ctc tca ggg aac tca cct aag aca ggg acc tca gag tgg gca gtt     720
Ser Leu Ser Gly Asn Ser Pro Lys Thr Gly Thr Ser Glu Trp Ala Val
225                 230                 235                 240 cct cag cct tca aga tta aag tat cgg caa aaa ttt aat agt cta gac     768
Pro Gln Pro Ser Arg Leu Lys Tyr Arg Gln Lys Phe Asn Ser Leu Asp
                245                 250                 255 aaa ggc atg agc gga tac ctc tca ggt ttt caa gct aga aat gcc ctt     816
Lys Gly Met Ser Gly Tyr Leu Ser Gly Phe Gln Ala Arg Asn Ala Leu
            260                 265                 270 ctt cag tca aat ctc tct caa act cag cta gct act att tgg act ctg     864
Leu Gln Ser Asn Leu Ser Gln Thr Gln Leu Ala Thr Ile Trp Thr Leu
        275                 280                 285 gct gac atc gat ggt gac gga cag ttg aaa gct gaa gaa ttt att ctg     912
```

```
                Ala Asp Ile Asp Gly Asp Gly Gln Leu Lys Ala Glu Glu Phe Ile Leu
                    290                 295                 300 gcg atg cac ctc act gac atg gcc aaa gct gga cag cca cta cca ctg        960
Ala Met His Leu Thr Asp Met Ala Lys Ala Gly Gln Pro Leu Pro Leu
305                 310                 315                 320 acg ttg cct ccc gag ctt gtc cct cca tct ttc aga ggg gga aag caa       1008
Thr Leu Pro Pro Glu Leu Val Pro Pro Ser Phe Arg Gly Gly Lys Gln
                325                 330                 335 gtt gat tct gtt aat gga act ctg cct tca tat cag aaa aca caa gaa       1056
Val Asp Ser Val Asn Gly Thr Leu Pro Ser Tyr Gln Lys Thr Gln Glu
            340                 345                 350 gaa gag cct cag aag aaa ctg cca gtt act ttt gag gac aaa cgg aaa       1104
Glu Glu Pro Gln Lys Lys Leu Pro Val Thr Phe Glu Asp Lys Arg Lys
        355                 360                 365 gcc aac tat gaa cga gga aac atg gag ctg gag aag cga cgc caa gtg       1152
Ala Asn Tyr Glu Arg Gly Asn Met Glu Leu Glu Lys Arg Arg Gln Val
    370                 375                 380 ttg atg gag cag cag cag agg gag gct gaa cgc aaa gcc cag aaa gag       1200
Leu Met Glu Gln Gln Gln Arg Glu Ala Glu Arg Lys Ala Gln Lys Glu
385                 390                 395                 400 aag gaa gag tgg gag cgg aaa cag aga gaa ctg caa gag caa gaa tgg       1248
Lys Glu Glu Trp Glu Arg Lys Gln Arg Glu Leu Gln Glu Gln Glu Trp
                405                 410                 415 aag aag cag ctg gag ttg gag aaa cgc ttg gag aaa cag aga gag ctg       1296
Lys Lys Gln Leu Glu Leu Glu Lys Arg Leu Glu Lys Gln Arg Glu Leu
            420                 425                 430 gag aga cag cgg gag gaa gag agg aga aag gag ata gaa aga cga gag       1344
Glu Arg Gln Arg Glu Glu Glu Arg Arg Lys Glu Ile Glu Arg Arg Glu
        435                 440                 445 gca gca aaa cag gag ctt gag aga caa cgc cgt tta gaa tgg gaa aga       1392
Ala Ala Lys Gln Glu Leu Glu Arg Gln Arg Arg Leu Glu Trp Glu Arg
    450                 455                 460 ctc cgt cgg cag gag ctg ctc agt cag aag acc agg gaa caa gaa gac       1440
Leu Arg Arg Gln Glu Leu Leu Ser Gln Lys Thr Arg Glu Gln Glu Asp
465                 470                 475                 480 att gtc agg ctg agc tcc aga aag aaa agt ctc cac ctg gaa ctg gaa       1488
Ile Val Arg Leu Ser Ser Arg Lys Lys Ser Leu His Leu Glu Leu Glu
                485                 490                 495 gca gtg aat gga aaa cat cag cag atc tca ggc aga cta caa gat gtc       1536
Ala Val Asn Gly Lys His Gln Gln Ile Ser Gly Arg Leu Gln Asp Val
            500                 505                 510 caa atc aga aag caa aca caa aag act gag cta gaa gtt ttg gat aaa       1584
Gln Ile Arg Lys Gln Thr Gln Lys Thr Glu Leu Glu Val Leu Asp Lys
        515                 520                 525 cag tgt gac ctg gaa att atg gaa atc aaa caa ctt caa caa gag ctt       1632
Gln Cys Asp Leu Glu Ile Met Glu Ile Lys Gln Leu Gln Gln Glu Leu
    530                 535                 540 aag gaa tat caa aat aag ctt atc tat ctg gtc cct gag aag cag cta       1680
Lys Glu Tyr Gln Asn Lys Leu Ile Tyr Leu Val Pro Glu Lys Gln Leu
545                 550                 555                 560 tta aac gaa aga att aaa aac atg cag ctc agt aac aca cct gat tca       1728
Leu Asn Glu Arg Ile Lys Asn Met Gln Leu Ser Asn Thr Pro Asp Ser
                565                 570                 575 ggg atc agt tta ctt cat aaa aag tca tca gaa aag gaa gaa tta tgc       1776
Gly Ile Ser Leu Leu His Lys Lys Ser Ser Glu Lys Glu Glu Leu Cys
            580                 585                 590 caa aga ctt aaa gaa caa tta gat gct ctt gaa aaa gaa act gca tct       1824
Gln Arg Leu Lys Glu Gln Leu Asp Ala Leu Glu Lys Glu Thr Ala Ser
        595                 600                 605
```

-continued

| | | |
|---|---|---|
| aag ctc tca gaa atg gat tca ttt aac aat cag ctg aag gaa ctc aga<br>Lys Leu Ser Glu Met Asp Ser Phe Asn Asn Gln Leu Lys Glu Leu Arg<br>610                         615                               620 | 1872 |
| gaa agc tat aat aca cag cag tta gcc ctt gaa caa ctt cat aaa atc<br>Glu Ser Tyr Asn Thr Gln Gln Leu Ala Leu Glu Gln Leu His Lys Ile<br>625                         630                        635               640 | 1920 |
| aaa cgt gac aaa ttg aag gaa atc gaa aga aaa aga tta gag caa att<br>Lys Arg Asp Lys Leu Lys Glu Ile Glu Arg Lys Arg Leu Glu Gln Ile<br>                          645                        650                        655 | 1968 |
| caa aaa aag aaa cta gaa gat gag gct gca agg aaa gca aag caa gga<br>Gln Lys Lys Lys Leu Glu Asp Glu Ala Ala Arg Lys Ala Lys Gln Gly<br>                      660                        665                        670 | 2016 |
| aaa gaa aac ttg tgg aga gaa agt att aga aag gaa gag gaa aag<br>Lys Glu Asn Leu Trp Arg Glu Ser Ile Arg Lys Glu Glu Glu Lys<br>675                       680                        685 | 2064 |
| caa aaa cga ctc cag gaa gaa aag tca cag gac aaa act caa gaa gag<br>Gln Lys Arg Leu Gln Glu Glu Lys Ser Gln Asp Lys Thr Gln Glu Glu<br>                      690                        695                      700 | 2112 |
| gaa cga aaa gct gag gca aaa caa agt gag aca gcc agt gct ttg gtg<br>Glu Arg Lys Ala Glu Ala Lys Gln Ser Glu Thr Ala Ser Ala Leu Val<br>705                         710                        715               720 | 2160 |
| aat tac aga gca ctg tac cct ttt gaa gca aga aac cat gat gag atg<br>Asn Tyr Arg Ala Leu Tyr Pro Phe Glu Ala Arg Asn His Asp Glu Met<br>                        725                        730                       735 | 2208 |
| agt ttt agt tct ggg gat ata att cag gtt gat gaa aaa act gta gga<br>Ser Phe Ser Ser Gly Asp Ile Ile Gln Val Asp Glu Lys Thr Val Gly<br>                      740                        745                      750 | 2256 |
| gag cct ggt tgg ctt tat ggt agt ttt cag gga aag ttt ggc tgg ttc<br>Glu Pro Gly Trp Leu Tyr Gly Ser Phe Gln Gly Lys Phe Gly Trp Phe<br>755                       760                        765 | 2304 |
| ccc tgc aac tat gta gaa aaa gtg ctg tca agt gaa aaa gct ctg tct<br>Pro Cys Asn Tyr Val Glu Lys Val Leu Ser Ser Glu Lys Ala Leu Ser<br>770                       775                        780 | 2352 |
| cct aag aag gcc tta ctt cct cct aca gtg tct ctc tct gct acc tca<br>Pro Lys Lys Ala Leu Leu Pro Pro Thr Val Ser Leu Ser Ala Thr Ser<br>785                       790                        795               800 | 2400 |
| act tct tcc cag cca cca gca tca gtg act gat tat cac aat gta tcc<br>Thr Ser Ser Gln Pro Pro Ala Ser Val Thr Asp Tyr His Asn Val Ser<br>                      805                        810                      815 | 2448 |
| ttc tca aac ctt act gtt aat aca aca tgg cag cag aag tca gct ttt<br>Phe Ser Asn Leu Thr Val Asn Thr Thr Trp Gln Gln Lys Ser Ala Phe<br>                      820                        825                      830 | 2496 |
| acc cgc act gtg tcc cct gga tct gtg tcc ccc att cac gga cag ggg<br>Thr Arg Thr Val Ser Pro Gly Ser Val Ser Pro Ile His Gly Gln Gly<br>                      835                        840                      845 | 2544 |
| cag gct gta gaa aac ctg aaa gcc cag gcc ctt tgt tcc tgg acg gca<br>Gln Ala Val Glu Asn Leu Lys Ala Gln Ala Leu Cys Ser Trp Thr Ala<br>850                       855                        860 | 2592 |
| aag aag gag aac cac ctg aac ttc tca aag cac gac gtc atc act gtc<br>Lys Lys Glu Asn His Leu Asn Phe Ser Lys His Asp Val Ile Thr Val<br>865                       870                        875               880 | 2640 |
| ctg gag cag cag gaa aac tgg tgg ttt ggg gag gtg cac gga gga aga<br>Leu Glu Gln Gln Glu Asn Trp Trp Phe Gly Glu Val His Gly Gly Arg<br>                      885                        890                      895 | 2688 |
| gga tgg ttc ccc aag tct tat gtc aag ctc att cct ggg aat gaa gta<br>Gly Trp Phe Pro Lys Ser Tyr Val Lys Leu Ile Pro Gly Asn Glu Val<br>                      900                        905                      910 | 2736 |
| cag cga gga gag cca gaa gct ttg tat gca gct gtg act aag aaa cct<br>Gln Arg Gly Glu Pro Glu Ala Leu Tyr Ala Ala Val Thr Lys Lys Pro<br>915                       920                        925 | 2784 |

```
acc tcc aca gcc tat cca gtt acc tcc aca gcc tat cca gtt gga gaa      2832
Thr Ser Thr Ala Tyr Pro Val Thr Ser Thr Ala Tyr Pro Val Gly Glu
        930                 935                 940 gac tac att gca ctt tat tca tac tca agt gta gag ccc ggg gat ttg      2880
Asp Tyr Ile Ala Leu Tyr Ser Tyr Ser Ser Val Glu Pro Gly Asp Leu
945                 950                 955                 960 act ttc act gaa ggt gaa gaa att cta gtg acc cag aaa gat gga gag      2928
Thr Phe Thr Glu Gly Glu Glu Ile Leu Val Thr Gln Lys Asp Gly Glu
                965                 970                 975 tgg tgg aca gga agt att gga gag aga act gga atc ttc ccg tcc aac      2976
Trp Trp Thr Gly Ser Ile Gly Glu Arg Thr Gly Ile Phe Pro Ser Asn
            980                 985                 990 tac gtc aga cca aag gat caa gag  aat ttt ggg aat gct  agc aaa tct    3024
Tyr Val Arg Pro Lys Asp Gln Glu  Asn Phe Gly Asn Ala  Ser Lys Ser
            995                 1000                1005 gga gca tca aac aaa aaa ccc  gag atc gct caa gta  act tca gca        3069
Gly Ala Ser Asn Lys Lys Pro  Glu Ile Ala Gln Val  Thr Ser Ala
       1010                1015                1020 tat gct gct tca ggg act gag  cag ctc agc ctt gcg  cca gga cag        3114
Tyr Ala Ala Ser Gly Thr Glu  Gln Leu Ser Leu Ala  Pro Gly Gln
   1025                1030                1035 tta ata tta atc tta aag aaa  aac aca agc ggg tgg  tgg caa gga        3159
Leu Ile Leu Ile Leu Lys Lys  Asn Thr Ser Gly Trp  Trp Gln Gly
   1040                1045                1050 gag cta cag gcc aga ggg aag  aaa cga cag aag gga  tgg ttt cct        3204
Glu Leu Gln Ala Arg Gly Lys  Lys Arg Gln Lys Gly  Trp Phe Pro
   1055                1060                1065 gcc agc cat gta aag ctg cta  ggt cca agc agt gaa  aga acc atg        3249
Ala Ser His Val Lys Leu Leu  Gly Pro Ser Ser Glu  Arg Thr Met
   1070                1075                1080 cct act ttt cac gct gta tgt  caa gtg att gct atg  tat gac tac        3294
Pro Thr Phe His Ala Val Cys  Gln Val Ile Ala Met  Tyr Asp Tyr
   1085                1090                1095 atg gcg aat aac gaa gat gag  ctc aat ttc tcc aaa  gga cag ctg        3339
Met Ala Asn Asn Glu Asp Glu  Leu Asn Phe Ser Lys  Gly Gln Leu
   1100                1105                1110 att aat gtt atg aac aaa gat  gac cct gac tgg tgg  caa gga gaa        3384
Ile Asn Val Met Asn Lys Asp  Asp Pro Asp Trp Trp  Gln Gly Glu
   1115                1120                1125 acc aat ggt ctg act ggt ctc  ttt cct tca aac tat  gtt aag atg        3429
Thr Asn Gly Leu Thr Gly Leu  Phe Pro Ser Asn Tyr  Val Lys Met
   1130                1135                1140 aca aca gac tca gat cca agt  caa cag tgg tgt gct  gac ctc caa        3474
Thr Thr Asp Ser Asp Pro Ser  Gln Gln Trp Cys Ala  Asp Leu Gln
   1145                1150                1155 gcc ctg gac aca atg cag cct  acg gag agg aag cga  cag ggc tac        3519
Ala Leu Asp Thr Met Gln Pro  Thr Glu Arg Lys Arg  Gln Gly Tyr
   1160                1165                1170 att cac gag ctc att cag aca  gag gag cgg tac atg  gac gac ctg        3564
Ile His Glu Leu Ile Gln Thr  Glu Glu Arg Tyr Met  Asp Asp Leu
   1175                1180                1185 caa ctt ttt gaa caa aaa act ctc ctt tga                              3594
Gln Leu Phe Glu Gln Lys Thr Leu Leu
   1190                1195

<210> SEQ ID NO 6
<211> LENGTH: 1197
<212> TYPE: PRT
<213> ORGANISM: Mus musculus
```

<400> SEQUENCE: 6

```
Met Ala Gln Phe Pro Thr Ala Met Asn Gly Gly Pro Asn Met Trp Ala
1               5                   10                  15

Ile Thr Ser Glu Glu Arg Thr Lys His Asp Lys Gln Phe Asp Asn Leu
            20                  25                  30

Lys Pro Ser Gly Gly Tyr Ile Thr Gly Asp Gln Ala Arg Thr Phe Phe
        35                  40                  45

Leu Gln Ser Gly Leu Pro Ala Pro Val Leu Ala Glu Ile Trp Ala Leu
    50                  55                  60

Ser Asp Leu Asn Lys Asp Gly Lys Met Asp Gln Gln Glu Phe Ser Ile
65                  70                  75                  80

Ala Met Lys Leu Ile Lys Leu Lys Leu Gln Gly Gln Gln Leu Pro Val
                85                  90                  95

Val Leu Pro Pro Ile Met Lys Gln Pro Pro Met Phe Ser Pro Leu Ile
            100                 105                 110

Ser Ala Arg Phe Gly Met Gly Ser Met Pro Asn Leu Ser Ile His Gln
        115                 120                 125

Pro Leu Pro Pro Val Ala Pro Ile Ala Thr Pro Leu Ser Ser Ala Thr
130                 135                 140

Ser Gly Thr Ser Ile Pro Pro Leu Met Met Pro Ala Pro Leu Val Pro
145                 150                 155                 160

Ser Val Ser Thr Ser Ser Leu Pro Asn Gly Thr Ala Ser Leu Ile Gln
            165                 170                 175

Pro Leu Ser Ile Pro Tyr Ser Ser Thr Leu Pro His Ala Ser Ser
        180                 185                 190

Tyr Ser Leu Met Met Gly Gly Phe Gly Gly Ala Ser Ile Gln Lys Ala
        195                 200                 205

Gln Ser Leu Ile Asp Leu Gly Ser Ser Ser Thr Ser Ser Thr Ala
    210                 215                 220

Ser Leu Ser Gly Asn Ser Pro Lys Thr Gly Thr Ser Glu Trp Ala Val
225                 230                 235                 240

Pro Gln Pro Ser Arg Leu Lys Tyr Arg Gln Lys Phe Asn Ser Leu Asp
                245                 250                 255

Lys Gly Met Ser Gly Tyr Leu Ser Gly Phe Gln Ala Arg Asn Ala Leu
            260                 265                 270

Leu Gln Ser Asn Leu Ser Gln Thr Gln Leu Ala Thr Ile Trp Thr Leu
        275                 280                 285

Ala Asp Ile Asp Gly Asp Gly Gln Leu Lys Ala Glu Glu Phe Ile Leu
    290                 295                 300

Ala Met His Leu Thr Asp Met Ala Lys Ala Gly Gln Pro Leu Pro Leu
305                 310                 315                 320

Thr Leu Pro Pro Glu Leu Val Pro Pro Ser Phe Arg Gly Gly Lys Gln
                325                 330                 335

Val Asp Ser Val Asn Gly Thr Leu Pro Ser Tyr Gln Lys Thr Gln Glu
            340                 345                 350

Glu Glu Pro Gln Lys Lys Leu Pro Val Thr Phe Glu Asp Lys Arg Lys
        355                 360                 365

Ala Asn Tyr Glu Arg Gly Asn Met Glu Leu Glu Lys Arg Arg Gln Val
    370                 375                 380

Leu Met Glu Gln Gln Arg Glu Ala Glu Arg Lys Ala Gln Lys Glu
385                 390                 395                 400

Lys Glu Glu Trp Glu Arg Lys Gln Arg Glu Leu Gln Glu Gln Glu Trp
                405                 410                 415
```

```
Lys Lys Gln Leu Glu Leu Glu Lys Arg Leu Lys Gln Arg Glu Leu
        420                 425                 430
Glu Arg Gln Arg Glu Glu Arg Arg Lys Glu Ile Glu Arg Arg Glu
        435                 440                 445
Ala Ala Lys Gln Glu Leu Glu Arg Gln Arg Arg Leu Glu Trp Glu Arg
450                 455                 460
Leu Arg Arg Gln Glu Leu Leu Ser Gln Lys Thr Arg Glu Gln Glu Asp
465                 470                 475                 480
Ile Val Arg Leu Ser Ser Arg Lys Lys Ser Leu His Leu Glu Leu Glu
                485                 490                 495
Ala Val Asn Gly Lys His Gln Gln Ile Ser Gly Arg Leu Gln Asp Val
                500                 505                 510
Gln Ile Arg Lys Gln Thr Gln Lys Thr Glu Leu Glu Val Leu Asp Lys
                515                 520                 525
Gln Cys Asp Leu Glu Ile Met Glu Ile Lys Gln Leu Gln Gln Glu Leu
                530                 535                 540
Lys Glu Tyr Gln Asn Lys Leu Ile Tyr Leu Val Pro Glu Lys Gln Leu
545                 550                 555                 560
Leu Asn Glu Arg Ile Lys Asn Met Gln Leu Ser Asn Thr Pro Asp Ser
                565                 570                 575
Gly Ile Ser Leu Leu His Lys Lys Ser Ser Lys Glu Glu Leu Cys
                580                 585                 590
Gln Arg Leu Lys Glu Gln Leu Asp Ala Leu Lys Glu Thr Ala Ser
                595                 600                 605
Lys Leu Ser Glu Met Asp Ser Phe Asn Asn Gln Leu Lys Glu Leu Arg
                610                 615                 620
Glu Ser Tyr Asn Thr Gln Gln Leu Ala Leu Glu Gln Leu His Lys Ile
625                 630                 635                 640
Lys Arg Asp Lys Leu Lys Glu Ile Glu Arg Lys Arg Leu Glu Gln Ile
                645                 650                 655
Gln Lys Lys Lys Leu Glu Asp Glu Ala Ala Arg Lys Ala Lys Gln Gly
                660                 665                 670
Lys Glu Asn Leu Trp Arg Glu Ser Ile Arg Lys Glu Glu Glu Lys
                675                 680                 685
Gln Lys Arg Leu Gln Glu Glu Lys Ser Gln Asp Lys Thr Gln Glu Glu
                690                 695                 700
Glu Arg Lys Ala Glu Ala Lys Gln Ser Glu Thr Ala Ser Ala Leu Val
705                 710                 715                 720
Asn Tyr Arg Ala Leu Tyr Pro Phe Glu Ala Arg Asn His Asp Glu Met
                725                 730                 735
Ser Phe Ser Ser Gly Asp Ile Ile Gln Val Asp Glu Lys Thr Val Gly
                740                 745                 750
Glu Pro Gly Trp Leu Tyr Gly Ser Phe Gln Gly Lys Phe Gly Trp Phe
                755                 760                 765
Pro Cys Asn Tyr Val Glu Lys Val Leu Ser Ser Glu Lys Ala Leu Ser
                770                 775                 780
Pro Lys Lys Ala Leu Leu Pro Pro Thr Val Ser Leu Ser Ala Thr Ser
785                 790                 795                 800
Thr Ser Ser Gln Pro Pro Ala Ser Val Thr Asp Tyr His Asn Val Ser
                805                 810                 815
Phe Ser Asn Leu Thr Val Asn Thr Thr Trp Gln Gln Lys Ser Ala Phe
                820                 825                 830
```

-continued

Thr Arg Thr Val Ser Pro Gly Ser Val Ser Pro Ile His Gly Gln Gly
        835                 840                 845

Gln Ala Val Glu Asn Leu Lys Ala Gln Ala Leu Cys Ser Trp Thr Ala
850                 855                 860

Lys Lys Glu Asn His Leu Asn Phe Ser Lys His Asp Val Ile Thr Val
865                 870                 875                 880

Leu Glu Gln Gln Glu Asn Trp Trp Phe Gly Glu Val His Gly Gly Arg
                    885                 890                 895

Gly Trp Phe Pro Lys Ser Tyr Val Lys Leu Ile Pro Gly Asn Glu Val
            900                 905                 910

Gln Arg Gly Glu Pro Glu Ala Leu Tyr Ala Ala Val Thr Lys Lys Pro
        915                 920                 925

Thr Ser Thr Ala Tyr Pro Val Thr Ser Thr Ala Tyr Pro Val Gly Glu
    930                 935                 940

Asp Tyr Ile Ala Leu Tyr Ser Tyr Ser Ser Val Glu Pro Gly Asp Leu
945                 950                 955                 960

Thr Phe Thr Glu Gly Glu Glu Ile Leu Val Thr Gln Lys Asp Gly Glu
                965                 970                 975

Trp Trp Thr Gly Ser Ile Gly Glu Arg Thr Gly Ile Phe Pro Ser Asn
            980                 985                 990

Tyr Val Arg Pro Lys Asp Gln Glu  Asn Phe Gly Asn Ala  Ser Lys Ser
        995                 1000                1005

Gly Ala  Ser Asn Lys Lys Pro  Glu Ile Ala Gln Val  Thr Ser Ala
     1010                1015                1020

Tyr Ala  Ala Ser Gly Thr Glu  Gln Leu Ser Leu Ala  Pro Gly Gln
     1025                1030                1035

Leu Ile  Leu Ile Leu Lys Lys  Asn Thr Ser Gly Trp  Trp Gln Gly
     1040                1045                1050

Glu Leu  Gln Ala Arg Gly Lys  Lys Arg Gln Lys Gly  Trp Phe Pro
     1055                1060                1065

Ala Ser  His Val Lys Leu Leu  Gly Pro Ser Ser Glu  Arg Thr Met
     1070                1075                1080

Pro Thr  Phe His Ala Val Cys  Gln Val Ile Ala Met  Tyr Asp Tyr
     1085                1090                1095

Met Ala  Asn Asn Glu Asp Glu  Leu Asn Phe Ser Lys  Gly Gln Leu
     1100                1105                1110

Ile Asn  Val Met Asn Lys Asp  Asp Pro Asp Trp Trp  Gln Gly Glu
     1115                1120                1125

Thr Asn  Gly Leu Thr Gly Leu  Phe Pro Ser Asn Tyr  Val Lys Met
     1130                1135                1140

Thr Thr  Asp Ser Asp Pro Ser  Gln Gln Trp Cys Ala  Asp Leu Gln
     1145                1150                1155

Ala Leu  Asp Thr Met Gln Pro  Thr Glu Arg Lys Arg  Gln Gly Tyr
     1160                1165                1170

Ile His  Glu Leu Ile Gln Thr  Glu Glu Arg Tyr Met  Asp Asp Leu
     1175                1180                1185

Gln Leu  Phe Glu Gln Lys Thr  Leu Leu
     1190                1195

<210> SEQ ID NO 7
<211> LENGTH: 738
<212> TYPE: DNA
<213> ORGANISM: Mus musculus

<400> SEQUENCE: 7

-continued

```
ccgtcttcca catttcccac attgatcgtg tgtacacact ccgaacagac aacatcaacg      60
agaggacggc ctgggtccag aagatcaagg gtgcctcaga gcagtacatc gacactgaga     120 agaaaaacg ggaaaaggct taccaagccc gttctcaaaa gacttcaggt attgggcgtc      180
tgatggtgca tgtcattgaa gctacagaat taaaagcctg caaccaaac gggaaaagta     240 atccatactg tgaagtcagc atgggctccc aaagctatac caccaggacc ctgcaggaca     300
cactaaaccc caagtggaac ttcaactgcc agttcttcat caaggatctt taccaggacg     360
ttctgtgtct cactatgttt gacagagacc agttttctcc agatgacttc ttgggtcgta     420
ctgaagttcc agtggcaaaa atccgaacag aacaggaaag caaggcccc accacccgcc     480 gactactact gcacgaagtc cccactggag aagtctgggt ccgctttgac ctgcaacttt     540
ttgaacaaaa aactctcctt tgagggcctg gggaagccag aaccagggga gctgcccaca     600
aggctgggtc taaagacaga ttttgctctc ccaggacaga ggagcatcac atggcttcat     660
ccatcaaaca gccacactcg ctgggcctgt atttattgc acactaaatt gctagcaatc     720
tatgcaaaca tgatctttt                                                  738
```

<210> SEQ ID NO 8
<211> LENGTH: 186
<212> TYPE: PRT
<213> ORGANISM: Mus musculus

<400> SEQUENCE: 8

```
Val Phe His Ile Ser His Ile Asp Arg Val Tyr Thr Leu Arg Thr Asp
1               5                  10                  15

Asn Ile Asn Glu Arg Thr Ala Trp Val Gln Lys Ile Lys Gly Ala Ser
            20                  25                  30

Glu Gln Tyr Ile Asp Thr Glu Lys Lys Arg Glu Lys Ala Tyr Gln
        35                  40                  45

Ala Arg Ser Gln Lys Thr Ser Gly Ile Gly Arg Leu Met Val His Val
    50                  55                  60

Ile Glu Ala Thr Glu Leu Lys Ala Cys Lys Pro Asn Gly Lys Ser Asn
65                  70                  75                  80

Pro Tyr Cys Glu Val Ser Met Gly Ser Gln Ser Tyr Thr Thr Arg Thr
                85                  90                  95

Leu Gln Asp Thr Leu Asn Pro Lys Trp Asn Phe Asn Cys Gln Phe Phe
            100                 105                 110

Ile Lys Asp Leu Tyr Gln Asp Val Leu Cys Leu Thr Met Phe Asp Arg
        115                 120                 125

Asp Gln Phe Ser Pro Asp Asp Phe Leu Gly Arg Thr Glu Val Pro Val
    130                 135                 140

Ala Lys Ile Arg Thr Glu Gln Glu Ser Lys Gly Pro Thr Thr Arg Arg
145                 150                 155                 160

Leu Leu Leu His Glu Val Pro Thr Gly Glu Val Trp Val Arg Phe Asp
                165                 170                 175

Leu Gln Leu Phe Glu Gln Lys Thr Leu Leu
            180                 185
```

<210> SEQ ID NO 9
<211> LENGTH: 1078
<212> TYPE: DNA
<213> ORGANISM: Mus musculus

<400> SEQUENCE: 9

-continued

```
gaattcggca cgagggctga gagaagcgga ctccgaggac tctgatgctg aagagaagcc     60
tgttaagcag gaggacttcc cgaagattta ggaccaaaga agttaaagac gggtggcaat    120
tttaagccca gccagaaagg cttttcagga ggaaccaagt ccttcatgga ctttggcagc    180
tgggagagac acacgaaagg gatcgggcag aagctgctgc agaagatggg ctacgtccct    240
ggcgtggcc tggggaagaa cgcacagggg atcatcaacc ccatcgaagc caaacagaga    300
aaaggcaagg gagccgtggg ggcctatggc tcggagagga ccactcagtc tctgcaggac    360
ttccccgtgg ccgactcgga agaggaggca gaagaggagt tcagaagga gctgagccaa    420
tggaggaaag accccagcgg gagcaagaag aagccaaagt actcttacaa gactgtggag    480
gagctgaagg ccaagggcag ggtcagcaag aagctcacag cacctcagaa ggaactgtct    540
caggtcaagg tgatcgacat gacaggccgg gagcagaagg tgtactacag ctacagccaa    600
atcagccaca agcacagcgt gcccgatgaa ggggtgccat tgctggcgca gctgccccc    660
acagccggca aggaagccag gatgccgggc tttgcactgc ctgagctgga gcacaacctg    720
cagctgctca ttgagcgcac ggagcaggag atcatccaga gcgaccggca gctccagtat    780
gagcgggaca tggtggtcag cctgtcgcat gagctggaga agacggccga ggttcttgca    840
catgaggagc gtgtcatctc taacctcagc aaggtgctgg ccctggtgga ggaatgtgag    900
cgccgcatgc agccccatgg caccgacccc ctcactctgg atgagtgtgc ccgcatcttt    960
gagacactac aggacaagta ttatgaggag taccgcctgg cggaccgcgc agacctcgct   1020
gtggccattg tctacccgct cgtgaaggac tactttaagg attggcaccc ctcgaggg    1078
```

<210> SEQ ID NO 10
<211> LENGTH: 309
<212> TYPE: PRT
<213> ORGANISM: Mus musculus
<400> SEQUENCE: 10

```
Gly Thr Lys Ser Phe Met Asp Phe Gly Ser Trp Glu Arg His Thr Lys
 1               5                  10                  15

Gly Ile Gly Gln Lys Leu Leu Gln Lys Met Gly Tyr Val Pro Gly Arg
             20                  25                  30

Gly Leu Gly Lys Asn Ala Gln Gly Ile Ile Asn Pro Ile Glu Ala Lys
         35                  40                  45

Gln Arg Lys Gly Lys Gly Ala Val Gly Ala Tyr Gly Ser Glu Arg Thr
     50                  55                  60

Thr Gln Ser Leu Gln Asp Phe Pro Val Ala Asp Ser Glu Glu Glu Ala
 65                  70                  75                  80

Glu Glu Glu Phe Gln Lys Glu Leu Ser Gln Trp Arg Lys Asp Pro Ser
                 85                  90                  95

Gly Ser Lys Lys Lys Pro Lys Tyr Ser Tyr Lys Thr Val Glu Glu Leu
            100                 105                 110

Lys Ala Lys Gly Arg Val Ser Lys Lys Leu Thr Ala Pro Gln Lys Glu
        115                 120                 125

Leu Ser Gln Val Lys Val Ile Asp Met Thr Gly Arg Glu Gln Lys Val
    130                 135                 140

Tyr Tyr Ser Tyr Ser Gln Ile Ser His Lys His Ser Val Pro Asp Glu
145                 150                 155                 160

Gly Val Pro Leu Leu Ala Gln Leu Pro Pro Thr Ala Gly Lys Glu Ala
                165                 170                 175

Arg Met Pro Gly Phe Ala Leu Pro Glu Leu Glu His Asn Leu Gln Leu
            180                 185                 190
```

-continued

```
Leu Ile Glu Arg Thr Glu Gln Glu Ile Ile Gln Ser Asp Arg Gln Leu
            195                 200                 205
Gln Tyr Glu Arg Asp Met Val Val Ser Leu Ser His Glu Leu Glu Lys
        210                 215                 220
Thr Ala Glu Val Leu Ala His Glu Glu Arg Val Ile Ser Asn Leu Ser
225                 230                 235                 240
Lys Val Leu Ala Leu Val Glu Glu Cys Glu Arg Arg Met Gln Pro His
                245                 250                 255
Gly Thr Asp Pro Leu Thr Leu Asp Glu Cys Ala Arg Ile Phe Glu Thr
            260                 265                 270
Leu Gln Asp Lys Tyr Tyr Glu Glu Tyr Arg Leu Ala Asp Arg Ala Asp
        275                 280                 285
Leu Ala Val Ala Ile Val Tyr Pro Leu Val Lys Asp Tyr Phe Lys Asp
    290                 295                 300
Trp His Pro Ser Arg
305

<210> SEQ ID NO 11
<211> LENGTH: 97
<212> TYPE: DNA
<213> ORGANISM: Mus musculus

<400> SEQUENCE: 11
catggcggcg gctgcggagg gcgtcccggc gacgcgacgg aggacgagcc acctcgagat      60
gatgctgcgg tggagacagc cgaggaagca aggagc                               97

<210> SEQ ID NO 12
<211> LENGTH: 123
<212> TYPE: DNA
<213> ORGANISM: Mus musculus

<400> SEQUENCE: 12
cttgagtcta ctgaaaatac cctgcaggaa gctacatcat ccatgtcttt gatgacccaa      60
tttgaacagg aagtatctgg cctccaaaga ccatacgtga tattgagact agcgaagaga     120
tgc                                                                   123

<210> SEQ ID NO 13
<211> LENGTH: 140
<212> TYPE: DNA
<213> ORGANISM: Mus musculus

<400> SEQUENCE: 13
gaattcggca cgagggagtc tggttctgga agccgacag aagctgagct tgtcaactta       60
gatttcttgg gagatttgga tgttccggta tctgccccac ccctgtgtgt ctgagctcga     120
gtctctctgc tggactatgg                                                 140

<210> SEQ ID NO 14
<211> LENGTH: 2855
<212> TYPE: DNA
<213> ORGANISM: Mus musculus

<400> SEQUENCE: 14
ctttacgagc agagggagcc aaattcagag ccgttttaga taaagctgtg caagcggatg      60
gacaggtgaa ggagcgctac cagtcccatc gagacaccat cgcacttctg tgtaagccgg     120
agccagagct gaatgctgcc atcccctctg ctaacccagc aaagaccatg cagggcagcg     180
```

-continued

| | |
|---|---|
| aggttgtaag tgtcttaaag tccttattat caaatcttga tgaaatcaag aaggaaagag | 240 |
| agagtcttga gaatgacctg aagtcagtga attttgacat gacaagcaag tttttgacag | 300 |
| ctctggccca agatggcgtg ataaatgagg aggctctctc tgtcactgag ctggatcgga | 360 |
| tctatggcgg tctaacaagt aaagttcaag agtctctgaa gaaacaagag ggacttctaa | 420 |
| aaaatataca ggtctcacac caagaattct ccaaaatgaa gcaatctaac aacgaggcta | 480 |
| acttgagaga agaagttctg aagaacctag caactgcgta tgacaacttt gttgagcttg | 540 |
| tagctaactt gaaggagggc acaaagtttt acaatgagct gactgagatc ctggtcaggt | 600 |
| tccagaacaa atgcagtgac atagtgtttg cacggaagac agaaagagac gagctcttga | 660 |
| aggatctgca gcagagcatt gccagagagc ccagcgctcc ttcaatccct cctccagcct | 720 |
| atcagtcctc cccagcagcg gggcatgcag cagcgcctcc aactccagcc caagaaccca | 780 |
| tgccgcctgc taagccccag cctccagccc ggcctccacc tcctgtgctt cctgcaaacc | 840 |
| gagttcctcc tgcttctgct gctgctgccc ctgcaggcgt ggggacggct tcagcagcgc | 900 |
| cgccacagac ccctggctct gctcccccgc cacaggctca gggaccacca taccctacct | 960 |
| atccaggata tcccgggtat tgccaaatgc ccatgcccat gggctacaac ccctacgcat | 1020 |
| atggccagta caatatgccg tacccaccgg tgtatcacca gagccccgga caggctccat | 1080 |
| acccaggacc ccagcagcct acctacccct ccctcagcc cccgcagcag tcctactatc | 1140 |
| cacagcagta acgctgccac gtgctgctgg ttcagatcag agcgacagga cagcagctgc | 1200 |
| caccagctct aagccacgct ctggccactc gagagtatct tgctctattg attgctgtgg | 1260 |
| atgatttctg tctgtggcta aagccgaagg ctgggcccca cctccacatt tgatcgcact | 1320 |
| cgtgagattc tgctgctgtt gcagtataaa cgctagctat aatagcattt gaaaaaaatt | 1380 |
| acagttccat aaaatgctga aaatgagaaa ttaaacctgc aagtgaaaca tttgaaatta | 1440 |
| gcatacttta taagatgcag ttgggacaaa gatggcttaa gtactgatat ttaaggaaaa | 1500 |
| agttttcttt ctcttttggt ttattgattt agtttaattt ctattatgat attttgcata | 1560 |
| atcaaggcat tgtaaatctt ataatttaaa aataaaattac ttacgaacag ttgtcattgt | 1620 |
| tatgttttgt cattgattct cattgctgtc tagttccttt ctggtattag cctctccttc | 1680 |
| tgtatgttca caggctccat tactgtgttg aattgcgtga cgtcaggtga gcagtcaggg | 1740 |
| agggctgctc tgcggacgcc aagcgcacac cagcttgtct caggctcagc agtcagctca | 1800 |
| tctggacatt tctatttaaa agtcctttaa tgtggaagat acacacaatt gttaccaaag | 1860 |
| gttcttccaa ttaattttac aatttaaaaa gtatgtatta atgttttatt gttagatttt | 1920 |
| ccaaaaaaat gatgcaaatt ctggtaatat tcatttccct cacccataat ttggttaaaa | 1980 |
| tgagtagttt tagccataca gtctcatctg ctgtggagga acctggagaa agtcccctgt | 2040 |
| gcctttctag cccttgggtt ctattcttat cctgcaatgt ctactgcaca gtgtgtttga | 2100 |
| gcagatccta accctccttt tacagtttct tcttcttact tctttattct ttttgtggct | 2160 |
| cctgaaatct gaggttattt tgtaattcag gagcatgcag acaattgtt gggacatgtg | 2220 |
| cctagtccgg aatacagccc aggacagcaa ggagatgcgc cctgcaccag gaagccgtgc | 2280 |
| aggcaggagc tgtccaaggt cccggcggct ctgcctgtgt gaggcaggag aatgagcaga | 2340 |
| ttccctaatc tatgttctcg aagtttaatg ctgatgttgt cttgccttat cctcatttaa | 2400 |
| ctgatactgt cacccagtcc acctttgctc tcattgcaaa gtgatagtgt aatttcaaat | 2460 |
| gtaagactga agatacgatt gtaaaaggga gtaaactggt ttaaacgtgt tattctaaag | 2520 |
| caccttactt tgttgttgta tgcagaaaac acagatgcgc taattcagta taaatgactg | 2580 |

```
attgcctgga atttggacgt tggcttaaag tccgatagct aaaccttggc aaaacataac    2640
aaacatttca ttgctcagcc tcagtgctct ggagtattca gtgtatgaga caggtttatt    2700
tgagtcctct gtaaatggca tttgaatttt atattctccc ctcccgagta tcttataaga    2760
catcccctga gttagggagt tcccagactg ctactctatt ccttatgaat gcaaacaac     2820 caccaataga acaaaaaaaa aaaaaaaaac tcgag                               2855
```

<210> SEQ ID NO 15
<211> LENGTH: 1151
<212> TYPE: DNA
<213> ORGANISM: Mus musculus

<400> SEQUENCE: 15

```
ctttacgagc agagggagcc aaattcagag ccgttttaga taaagctgtg caagcggatg      60
gacaggtgaa ggagcgctac cagtcccatc gagacaccat cgcacttctg tgtaagccgg     120
agccagagct gaatgctgcc atcccctctg ctaacccagc aaagaccatg cagggcagcg     180
aggttgtaag tgtcttaaag tccttattat caaatcttga tgaaatcaag aaggaaagag     240
agagtcttga gaatgacctg aagtcagtga attttgacat gacaagcaag ttttttgacag    300 ctctggccca agatggcgtg ataaatgagg aggctctctc tgtcactgag ctggatcgga     360
tctatggcgg tctaacaagt aaagttcaag agtctctgaa gaaacaagag ggacttctaa     420
aaaatataca ggtctcacac caagaattct ccaaaatgaa gcaatctaac aacgaggcta     480
acttgagaga agaagttctg aagaacctag caactgcgta tgacaacttt gttgagcttg     540
tagctaactt gaaggagggc acaaagtttt acaatgagct gactgagatc ctggtcaggt     600
tccagaacaa atgcagtgac atagtgtttg cacggaagac agaaagagac gagctcttga     660
aggatctgca gcagagcatt gccagagagc ccagcgctcc ttcaatccct cctccagcct     720
atcagtcctc cccagcagcg gggcatgcag cagcgcctcc aactccagcc caagaaccca    780
tgccgcctgc taagccccag cctccagccc ggcctccacc tcctgtgctt cctgcaaacc    840
gagttcctcc tgcttctgct gctgctgccc ctgcaggcgt ggggacggct tcagcagcgc    900
cgccacagac ccctggctct gctccccgc cacaggctca gggaccacca taccctacct    960
atccaggata tcccgggtat tgccaaatgc ccatgcccat gggctacaac ccctacgcat   1020
atggccagta caatatgccg tacccaccgg tgtatcacca gagccccgga caggctccat   1080
acccaggacc ccagcagcct acctacccct ccctcagcc ccgcagcag tcctactatc    1140 cacagcagta a                                                        1151
```

<210> SEQ ID NO 16
<211> LENGTH: 382
<212> TYPE: PRT
<213> ORGANISM: Mus musculus

<400> SEQUENCE: 16

```
Leu Arg Ala Glu Gly Ala Lys Phe Arg Ala Val Leu Asp Lys Ala Val
 1               5                  10                  15

Gln Ala Asp Gly Gln Val Lys Glu Arg Tyr Gln Ser His Arg Asp Thr
            20                  25                  30

Ile Ala Leu Leu Cys Lys Pro Glu Pro Glu Leu Asn Ala Ala Ile Pro
        35                  40                  45

Ser Ala Asn Pro Ala Lys Thr Met Gln Gly Ser Glu Val Val Ser Val
    50                  55                  60
```

```
Leu Lys Ser Leu Leu Ser Asn Leu Asp Glu Ile Lys Lys Glu Arg Glu
 65                  70                  75                  80

Ser Leu Glu Asn Asp Leu Lys Ser Val Asn Phe Asp Met Thr Ser Lys
                 85                  90                  95

Phe Leu Thr Ala Leu Ala Gln Asp Gly Val Ile Asn Glu Glu Ala Leu
            100                 105                 110

Ser Val Thr Glu Leu Asp Arg Ile Tyr Gly Gly Leu Thr Ser Lys Val
        115                 120                 125

Gln Glu Ser Leu Lys Lys Gln Glu Gly Leu Leu Lys Asn Ile Gln Val
130                 135                 140

Ser His Gln Glu Phe Ser Lys Met Lys Gln Ser Asn Asn Glu Ala Asn
145                 150                 155                 160

Leu Arg Glu Glu Val Leu Lys Asn Leu Ala Thr Ala Tyr Asp Asn Phe
                165                 170                 175

Val Glu Leu Val Ala Asn Leu Lys Glu Gly Thr Lys Phe Tyr Asn Glu
            180                 185                 190

Leu Thr Glu Ile Leu Val Arg Phe Gln Asn Lys Cys Ser Asp Ile Val
        195                 200                 205

Phe Ala Arg Lys Thr Glu Arg Asp Glu Leu Leu Lys Asp Leu Gln Gln
    210                 215                 220

Ser Ile Ala Arg Glu Pro Ser Ala Pro Ser Ile Pro Pro Ala Tyr
225                 230                 235                 240

Gln Ser Ser Pro Ala Ala Gly His Ala Ala Ala Pro Pro Thr Pro Ala
                245                 250                 255

Pro Arg Thr Met Pro Pro Ala Lys Pro Gln Pro Pro Ala Arg Pro Pro
            260                 265                 270

Pro Pro Val Leu Pro Ala Asn Arg Val Pro Pro Ser Ala Ala Ala
        275                 280                 285

Ala Pro Ala Gly Val Gly Thr Ala Ser Ala Ala Pro Pro Gln Thr Pro
290                 295                 300

Gly Ser Ala Pro Pro Gln Ala Gln Gly Pro Pro Tyr Pro Thr Tyr
305                 310                 315                 320

Pro Gly Tyr Pro Gly Tyr Cys Gln Met Pro Met Pro Met Gly Tyr Asn
                325                 330                 335

Pro Tyr Ala Tyr Gly Gln Tyr Asn Met Pro Tyr Pro Pro Val Tyr His
            340                 345                 350

Gln Ser Pro Gly Gln Ala Pro Tyr Pro Gly Pro Gln Gln Pro Thr Tyr
        355                 360                 365

Pro Phe Pro Gln Pro Gln Gln Ser Tyr Tyr Pro Gln Gln
370                 375                 380

<210> SEQ ID NO 17
<211> LENGTH: 1738
<212> TYPE: DNA
<213> ORGANISM: Mus musculus

<400> SEQUENCE: 17
ggtcttggct agaattttaa atttcttctc atttgagtaa aatgttgcat tctgaagtcc    60
catgctacct gaagttgcat ttggagtccc aagctactgg aatgtttata tgtgaccgtt   120
tcccaggagg cttacactgc agaaggaaga atgaatctag gtgaggtggg cagctgcttg   180
gcagtcctct cttgtgcccc aactgtaaac cagatagaaa tgttcagggg aggatacttt   240
cattattgtg gtttgtagtg ttaagatgat tgcttctgcc ttggaaatac ctcaagctgt   300
tcttatttaa caggtaagtg actgagtata atattccaga aaaatttgaa atcctaattt   360
```

```
cttccatatt tcattaaatt ttttgcatac aggtctaaca aatatggata tgtatacaca      420
tcctctttaa tgaaggtatt attttggtta cttttcctaa gatataccct aaaagatgtt      480
ctatacattt cctacttaaa ttctgggggga tttggagtat gtacatgata aaaaagatta     540
taatatatcg attgaagtta ctttattttc taattagaat tatttaata gtcctttatt      600
gaataagtgc tgtaatttgt ttgctatgag acttattcct gatgtgaatg taaattattt     660
ttccacatgc atgaaaaaat gtatgtacta atcagagttg tctccattgc attgaaatta     720
cttgttttga actaaagtaa ctcatattta tgtagtagaa tgcttatgtt ttcagacttt     780
gtaatgattt cctttggatg tattttaaat caatcggtct gggtaacata tcagtttaga     840
ttaatatgtg cttaaaagaa gaaaaaaatt caatggttca tagtagaaat gtgccacact     900
taaataagct ctgtatgaca tgaaattctg ttaaaacatt gtaattcatg gtgacttta      960
acttataaaa atactacttg cacgggttac ttgatttatg gatatatgaa aacttctcag    1020
gacgaaagtt cttctttctc tagaactatt cttctgtcgg tcatgcagaa tgctgttatt    1080
ctgaaaagtg tccctgttgc atatgatggt cactttattt gggggattc ttcataagat     1140
gtgagatgtt gatgccagtc tttcccaagt aagtgctcgt aaaaaaggac tactaactag    1200
cctgcatctg tctctaactg ggaccaaggg gtctgctgaa ggaaactgaa gagctctaac    1260
attttcacag cttggagaag atagaatctt taaaagtaca actgaagctt gatctatttt    1320
acaagtgcat tgatggcccc tgtccttctc tggttcctgt catttgaaac caactcctgt    1380
tgtaaatagg aagaatatgg gacattcata tttaagaaaa tttgatgtca ttaggtgact    1440
aagtagaagg cttagaaaaa tgtattcatt tgcaagtatt ttggcacaag aaattttcca    1500
actgaatagt aagcaaaagc taagttgttt cattgaaatc ataaggcagt ttaagataaa    1560
ctggagaaga taactgttct aatagaggat aatcgaattg attgtcaagt ggatgttatt    1620
tattggatag tgacagagtt tatttgtaac cttaattata ttaaaagtta ttctgttagg    1680
atgttttgta ttaataaacg tgaacaaaat taaaaaaaaa aaaaaaaaa ctcgaggg       1738
```

<210> SEQ ID NO 18
<211> LENGTH: 1521
<212> TYPE: DNA
<213> ORGANISM: Mus musculus
<220> FEATURE:
<221> NAME/KEY: misc_feature
<222> LOCATION: (102)..(103)
<223> OTHER INFORMATION: "n" represents any nucleotide.

<400> SEQUENCE: 18

```
gagaaggcgg cctgccgcag cgggacaacc tagagcgcga cgtggaggcg cgtagcggag       60
ctggagcaac tgcgcaccga ggtggatgtg cgcattagcg cnntggacac ctgcgtcaag      120
gccaagtcgc tgccagccgt cccgccgaga gtctcaggcc cacccccgaa ccctccaccc      180
attgatccag ctagcctgga ggaattcaag aaaaggatcc tggagtctca gcggctccct      240
gtagtcaacc ctgcwgccca acccagcggt tgagracccca gctgccgcag gacgctgggt     300
gccagaatcg cccacctgtg gatgggggca gccaggtgcc cacagtgctg gacacccgcc      360
gtgcctgccg gcagcctcca cccccagcgc cttctctggc accccttcac tgtcccstgc     420
atcccccrcca ttcsscasws askggattta aggcacacac agctgtgaga tgacttcaca     480
tcgacccctt gtgcagtgac ccggatggtg ccccacccac acatgaagca cccacagctc     540
agctgccacc ctaggcaact cctccggttt cctatcactc tgctcctgac ccgggaggtg      600
```

```
agaacaggaa gcccagcctt cagctccctt gggagtttcc agcctccctc ttaaaggcca      660
ctagggtttc cagatcctat ttgagagtct ccaggcctcc cctgaagggt tctagccacc      720
acgcccacag gattcccatt aggttttaaa gtcttttcca gagtccgctg gttccctcc       780 tcctcacaag gaagggcctc aattgtagat gagcgttccg ggtggatctt agagccctag      840
agggaggctt ttgcttgtar cccctaaag atattactgg cacataataa atatgaaagt       900
cctttgaaag ttggacactg cgcaaatggg gctctccatg gaccgcagcc catacgcccg      960 cacggggggac cagcagcgcg gctctggttc tacctgcgct atttcttcct cttcgtgtcg    1020
ctcattcagt tcctcatcat cctgggcctg gtcctcttca tgatctatgg caatgtgcac     1080
gccaccactg agtccagcct gcgcgccacg gagatccgcg ccgacagcct gtacagccag     1140
gtggttggac tatcggcctc acaggctaac ctgagcaaac agctgaacat cagcttgctt     1200
gtcaaggaaa cagtcatgca gcaactgttg actacgcgac gtgagatgga gcgcatcaac     1260
gccagcttcc gccagtgcca aggcgacctg atcacctaca taaactataa tcgcttcatc     1320
gccgctatca tcctgagcga gaagcagtgc caggaacagc tgaaggaggt caacaagacc     1380
tgcgaacttt actcttcaag ctgggagaaa aagttaagac actggagatg gaggtggcca     1440
aggagaaggc agtgtgctcc aaggacaagg agagcctgct ggcaggaaag cggcagacgg     1500
aagagcagct ggaggcctgt g                                                1521

<210> SEQ ID NO 19
<211> LENGTH: 720
<212> TYPE: DNA
<213> ORGANISM: Mus musculus

<400> SEQUENCE: 19
tgtgcgccgc ctctagaact agtggatccc ccgggcctgc aggaattccg gcacgacggc       60
cgagcgccgc ggaccacccg cggctgcccg ccgagccgtc gacatgtggg gggactgggg      120
tgggagcggc cggagcagcg ccaggtaccc gggcgcgcag aaccatggct ctcgctcgcc      180
tgtcctgacc tggcttgctc gccccaccga agaatgtcag ccaagtccaa ggggaaccct     240
cctcgtcctc cgcagccgag ggaccgccgg cagcctccaa aaccaaggtg aaggagcaga      300
tcaagatcat agtggaggat ctggaattag tcctgggcga cctgaaggac gtggccaaag      360
aacttaagga ggtggttgac cagattgaca ccctgacctc tgatctacag ctggaagatg      420
agatgaccga cagctccaaa acagacactc tgaacagcag ctccagtggg acaacagcct     480
ccagcataga gaagatcaaa gaacaggcca atgctcccct cattaaacct ccagcacacc     540
cgtctgctat cctgactgtc ctgagaaagc caaaccctcc accgcctcct ccaaggttga      600
cacccgtgag gtgtgaagag cctcagagag tggtgccgac tgccaaccct gtaaagacca      660
atggcactct tctgcggaat ggaggcttag cggggaggcc caacaaaatt ccaaatggag      720

<210> SEQ ID NO 20
<211> LENGTH: 801
<212> TYPE: DNA
<213> ORGANISM: Mus musculus

<400> SEQUENCE: 20
ctcgagtttt tttttttttt tttttttttt tttcattatt tactattatt tattgacata       60
tttccaaagc tcaaaatatt ttattataca tatagttgaa catatgtttc aaattgtata      120
gtatagaaaa taaacttttt tgtagtgtcc tcagcatttc atgatgcaaa actattgaca      180
aacatcttta gaaaataat aaaatagtcc ttcggtatta aaattcttat taaaaagcat      240
```

```
tagatcaaag ggagaactat gacatcatca atgcatagat gagataggca tgaatggaat      300
gagttgccct ggctttatca acaaatcaaa atatctgaca tcccagctct tataatagac      360
caaaatactt ggaatcagaa ggtcacagtt tgttttaggt caatcacaaa aaataaaat       420 tcattcatac tttctcaatt ttccgcagtt tctgatgatg aacatagaa acaatgtac        480 gtccaggaca gaggcgctac tctgcatact taccacgtga ttttttatgc cactttgttg     540
aatgcagatt aatatatttg ggcttttat tgcttgagta gaaagtgctc attacttatt     600
attttacgtt tatcatatag aaaattaaaa acaaacagaa cgttttctta aatggcagat     660
atcacactgt ggtagtggtg gatttcctca ggatggtctt ctgtggtttt ggtgcagcgg     720
gaggaggcac ggttgcaggt gtgggagggg ggaaactgtt actgtggctt attcccagtc     780
ccccattttc taatgggaaa t                                               801
```

```
<210> SEQ ID NO 21
<211> LENGTH: 119
<212> TYPE: DNA
<213> ORGANISM: Mus musculus

<400> SEQUENCE: 21
gcacagcccc cctccatcct gaagaaaacc tcagcgtatg ggcctccagc ttcgggccgt       60
gtctatcctt cctctcctgg gacatggtgt tccccgcttg ccccccctggc agaaaaccg     119

<210> SEQ ID NO 22
<211> LENGTH: 5738
<212> TYPE: DNA
<213> ORGANISM: Mus musculus

<400> SEQUENCE: 22
cggcacgagg aggagtggag cggcgcgggg agggcgcgca gcttggttgc tccgtagtac       60
ggcggctcgc aagggagcat cccgagcggg ctccggacg gccggaggc aggcaggcgg      120 gcgggcgggg atggtgtgcg cggctgcgga ctcggcgttc ctcgcgcggc gtgcgggctg      180
cactgatttg tgtgaggggc ggccgcgcgc acccgcccgg agatgaggcg tcgatcagca      240
aggtgaacgt aatagaacca tggctcagtt tcccacacct ttcggtggta gcctggatgt      300
ctgggccata actgtggagg aaagggccaa gcatgaccag cagttcctta gcctgaagcc      360
gatagcggga tttattactg gtgatcaagc gaggaacttt ttttttccaat ctgggttacc      420 tcagcctgtc ttagcacaaa tatgggcgct agcggacatg aataacgatg aaggatgga      480 tcaagtggaa ttttccatag ccatgaagct tatcaaactg aagctacaag gatatcagct      540
cccctccaca cttccccctg tcatgaaaca gcaaccagtg gctatttcca gtgcaccagc      600
atttggtata ggagggattg ctagcatgcc accactcaca gctgttgctc ctgtgccaat      660
gggctccatt ccagttgttg gaatgtctcc acccttagta tcttctgtcc ctccagcagc      720
agtgcctccc ctggctaacg gggctcctcc cgtcatacag cctctgcctg cgtttgcgca      780
tcctgcagcc acatggccaa agagttcttc cttcagcaga tctggtccag ggtcacaatt      840
aaacactaag ttacagaagg cacaatcatt cgatgtcgcc agcgcccctc cagcagcaga      900
atgggctgtg cctcagtcat caaggctgaa atacaggcag ttattcaaca gccacgacaa      960
aactatgagt ggacacttaa caggtcccca ggcaagaact attctcatgc aatcaagttt     1020
accccaggct cagctggctt caatatggaa tctttctgac attgatcaag atggaaaact     1080
cactgcagaa gaatttatcc tagctatgca cctaattgat gttgccatgt ctggtcagcc     1140
```

-continued

```
actgccgccc gtcctgcctc cagaatacat ccctccttcc ttcagaagag ttcgctccgg    1200
cagtgggatg tccgtcataa gctcttcttc tgtggatcag aggctgcctg aggagccgtc    1260
gtcagaggat gagcagcagc cagagaagaa actgcctgtg acatttgaag ataagaagcg    1320
ggagaacttc gagcgaggca gtgtggagct ggagaagcgc cggcaagcgc tcttggagca    1380
gcagcgcaaa gagcaggagc ggttggctca gctggagcgc gccgagcagg agaggaaaga    1440
gcgggagcgc caggagcagg aggccaagcg gcagctggag ctggagaagc agctggagaa    1500
gcagcgggag ctggagcggc agcgagagga ggagaggagg aaggagatcg agaggcgcga    1560
ggccgcaaaa cgggaactgg aaaggcagcg acaacttgaa tgggaacgga accggagaca    1620
ggaactcctg aatcagagga acaaggagca ggagggcacc gtggtcctga aggcaaggag    1680
gaagactctg gagtttgagt tagaagctct gaatgacaaa aagcatcagc tagaaggaaa    1740
acttcaggat atcaggtgtc gactggcaac ccagaggcaa gaaattgaga gcacgaacaa    1800
gtctagagag ctaagaattg ctgaaatcac ccacttacag cagcagttgc aggaatctca    1860
gcaaatgctt ggaagactta ttccagagaa acagatactc agtgaccagt taaaacaagt    1920
ccagcagaac agtttgcata gagactcgct tcttaccctc aaaagagcct tggaagcaaa    1980
ggagctggcc cggcagcagc tccgggagca gctggacgag gtggagagag agaccaggtc    2040
aaagctgcag gagattgatg ttttcaacaa ccagctgaag gaactgagag agatacatag    2100
caaacagcaa ctccagaagc agaggtccct ggaggcagcg cgactgaagc agaaagagca    2160
ggagaggaag agcctggagt tagagaagca aaaggaagac gctcagagac gagttcagga    2220
aagggacaag caatggctgg agcatgtgca gcaggaggag cagccacgcc cccggaaacc    2280
ccacgaggag gacagactga agagggaaga cagtgtcagg aagaaggagg cggaagagag    2340
agccaagccg gaaatgcaag acaagcagag tcggcttttc catccgcatc aggagccagc    2400
taagctggcc acccaggcac cctggtctac cacagagaaa ggcccgctta ccatttctgc    2460
acaggagagt gtaaaagtgg tatattaccg agcgctgtac ccctttgaat ccagaagtca    2520
cgatgagatc accatccagc caggagatat agtcatggtg gatgaaagcc agactggaga    2580
gccaggatgg cttggaggag agctgaaagg gaagacggga tggttccctg caaactatgc    2640
agaaaagatt ccagaaaatg aggttcccac tccagccaaa ccagtgaccg atctgacatc    2700
tgcccctgcc cccaaactgg ctctgcgtga gacccctgct cctttgccag tgacctcttc    2760
tgagccctcc acaaccccca caactgggc agacttcagt tccacgtggc ccagcagctc    2820
aaacgagaag ccagaaacgg acaactggga tacgtgggcg gctcagcctt ctctgaccgt    2880
acctagtgct ggccagttac ggcagagatc agcctttacc ccagccacag ccactggctc    2940
ctccccatct cccgtcctgg gccagggtga aaggtggaa gggctacaag cgcaagccct    3000
gtatccctgg agagccaaaa aagacaacca cttaaatttt aacaaaagtg acgtcatcac    3060
cgttctggaa cagcaagaca tgtggtggtt tggagaagtt caaggtcaga agggttggtt    3120
ccccaagtct tacgtgaaac tcatttcagg gcccgtaagg aaatccacaa gcatcgatac    3180
tggccctact gaaagtcctg ctagtctaaa gagagtggct tccccggccg ccaagccagc    3240
cattcccgga gaagagttta ttgccatgta cacatacgag agttctgagc aaggagattt    3300
aaccttccag caagggatg tgattgtggt taccaagaaa gatggtgact ggtggacggg    3360
aacggtgggc gacaagtccg gagtcttccc ttctaactat gtgaggctta agattcaga    3420 gggctctgga actgctggga aaacaggag tttaggaaaa aaacctgaaa ttgcccaggt    3480
tattgcttcc tacgctgcta ctggtcccga acaactcacc ctggctcctg gcagctgat    3540
```

-continued

```
tctgatccgg aaaaagaacc caggtggatg gtgggaagga gaactgcaag ctcgagggaa      3600
aaagcgccag ataggatggt ttccagcaaa ttatgtcaaa cttctaagcc ccggaacaag      3660
caaaatcacc ccaactgagc tacccaagac cgcagtgcag ccagcagtgt gccaggtgat      3720
cgggatgtac gattacaccg cccagaacga tgacgaacta gccttcagca aaggccagat      3780
catcaacgtc ctcaacaagg aggacccgga ctggtggaaa ggagaagtca gtgggcaagt      3840
tgggctcttc ccatccaatt atgtaaagct gaccacagac atggacccca gccagcaatg      3900
gtgctcagac ctgcatctct tagatatgct gaccccgact gagaggaagc ggcaaggcta      3960
catccatgaa ctcattgtca cggaggagaa ctacgtgaac gacttgcagc tggtcacaga      4020
gatctttcag aaaccctga cggagtctga gctgctgaca gaaaagagg ttgctatgat       4080 ttttgttaac tggaaggagc tgatcatgtg taatatcaaa ctgctgaaag cgctgagagt      4140
ccgcaagaag atgtctgggg agaagatgcc ggtgaagatg attggcgaca tcctgagcgc      4200
ccagctgccg cacatgcagc cttacatccg cttctgcagc tgccagctca atgggctgc       4260 cctcatccag cagaagacgg acgaggctcc agacttcaag gagttcgtca aaagactggc      4320
aatggaccct cggtgcaaag gaatgcctct gtccagcttt atactgaagc ctatgcagcg      4380
tgtcacaaga tacccgctga tcattaaaaa catcctggaa aacactcctg agaaccatcc      4440
agaccacagc cacctgaagc atgccctgga aaaggcggag gagctgtgct cccaggtgaa      4500
cgagggagtt cgagagaagg agaactcaga ccggctggag tggatccaag cccacgtgca      4560
gtgtgaaggc ctttctgagc aactggtgtt caattcagtg accaactgct gggaccacg       4620 caagttctg cacagcggga agctctacaa ggccaagagc aataaagaac tgtatggctt       4680
cctcttcaac gacttcctcc tgctgaccca atcacaaag cccttaggct cttccggcac       4740
cgacaaagtc ttcagcccca aatctaacct tcagtataaa atgtacaaaa cgcccatttt      4800
cttaaatgag gttctagtaa aattgcccac ggacccttct ggagatgagc ctatcttcca      4860
catttcccac atcgaccggg tctacaccct ccgagcagag agcataaatg agaggactgc      4920
ctgggtgcag aaaatcaagg cggcgtctga gctctacata gagacggaga aaagaagcg       4980 agagaaggcg tacctggtcc gttcccagcg ggcgaccggt attggaaggt tgatggtgaa      5040
cgtggtagaa ggcattgagc tgaagccctg tcggtcacat ggaaagagca cccgtactg       5100 tgaggtgacc atgggctctc agtgccacat caccaagaca atccaggaca cgctaaaccc      5160
caagtggaat tctaactgcc agttcttcat cagagacctg gagcaggagg ttctctgcat      5220
cacagtgttt gagagggacc agttctcgcc tgatgatttt ttgggtcgga cagagatccg      5280
agtggccgac atcaagaaag accagggctc caaggggccg gttacgaagt gtctcctgct      5340
gcatgaggtc cccacgggag agattgtggt ccgccttgac ctgcagttgt tgatgagcc       5400 gtagcagccc tgcgatgatc gtagatgact tcctcctcaa ggccccgtgc gggcgtgctg      5460
tctggtggtc agcctcagag caacggggat gaagcaaaga cgaagcccct cgaggctgct      5520
aggagtcgtt ctcgacaatc ctgcccttca aaccatgtct catttttatga atccaaattc     5580 tcttttcctt tgctctccct atggtctcat catggcttct agagtctctg aaatctgtga      5640
cctttaacta ggttccattg ggagcctggc tccttccctg gctggaggt gtgggtctgg       5700 tttctataaa atagattata aactcgagaa tcactagt                              5738
```

<210> SEQ ID NO 23
<211> LENGTH: 5145
<212> TYPE: DNA

-continued

```
<213> ORGANISM: Mus musculus
<220> FEATURE:
<221> NAME/KEY: CDS
<222> LOCATION: (1)..(5145)
<223> OTHER INFORMATION: Mouse Esel1L

<400> SEQUENCE: 23 atg gct cag ttt ccc aca cct ttc ggt ggt agc ctg gat gtc tgg gcc      48
Met Ala Gln Phe Pro Thr Pro Phe Gly Gly Ser Leu Asp Val Trp Ala
1               5                   10                  15 ata act gtg gag gaa agg gcc aag cat gac cag cag ttc ctt agc ctg      96
Ile Thr Val Glu Glu Arg Ala Lys His Asp Gln Gln Phe Leu Ser Leu
            20                  25                  30 aag ccg ata gcg gga ttt att act ggt gat caa gcg agg aac ttt ttt     144
Lys Pro Ile Ala Gly Phe Ile Thr Gly Asp Gln Ala Arg Asn Phe Phe
        35                  40                  45 ttc caa tct ggg tta cct cag cct gtc tta gca caa ata tgg gcg cta     192
Phe Gln Ser Gly Leu Pro Gln Pro Val Leu Ala Gln Ile Trp Ala Leu
    50                  55                  60 gcg gac atg aat aac gat gga agg atg gat caa gtg gaa ttt tcc ata     240
Ala Asp Met Asn Asn Asp Gly Arg Met Asp Gln Val Glu Phe Ser Ile
65              70                  75                  80 gcc atg aag ctt atc aaa ctg aag cta caa gga tat cag ctc ccc tcc     288
Ala Met Lys Leu Ile Lys Leu Lys Leu Gln Gly Tyr Gln Leu Pro Ser
                85                  90                  95 aca ctt ccc cct gtc atg aaa cag caa cca gtg gct att tcc agt gca     336
Thr Leu Pro Pro Val Met Lys Gln Gln Pro Val Ala Ile Ser Ser Ala
            100                 105                 110 cca gca ttt ggt ata gga ggg att gct agc atg cca cca ctc aca gct     384
Pro Ala Phe Gly Ile Gly Gly Ile Ala Ser Met Pro Pro Leu Thr Ala
        115                 120                 125 gtt gct cct gtg cca atg ggc tcc att cca gtt gtt gga atg tct cca     432
Val Ala Pro Val Pro Met Gly Ser Ile Pro Val Val Gly Met Ser Pro
    130                 135                 140 ccc tta gta tct tct gtc cct cca gca gca gtg cct ccc ctg gct aac     480
Pro Leu Val Ser Ser Val Pro Pro Ala Ala Val Pro Pro Leu Ala Asn
145                 150                 155                 160 ggg gct cct ccc gtc ata cag cct ctg cct gcg ttt gcg cat cct gca     528
Gly Ala Pro Pro Val Ile Gln Pro Leu Pro Ala Phe Ala His Pro Ala
                165                 170                 175 gcc aca tgg cca aag agt tct tcc ttc agc aga tct ggt cca ggg tca     576
Ala Thr Trp Pro Lys Ser Ser Ser Phe Ser Arg Ser Gly Pro Gly Ser
            180                 185                 190 caa tta aac act aag tta cag aag gca caa tca ttc gat gtc gcc agc     624
Gln Leu Asn Thr Lys Leu Gln Lys Ala Gln Ser Phe Asp Val Ala Ser
        195                 200                 205 gcc cct cca gca gca gaa tgg gct gtg cct cag tca tca agg ctg aaa     672
Ala Pro Pro Ala Ala Glu Trp Ala Val Pro Gln Ser Ser Arg Leu Lys
    210                 215                 220 tac agg cag tta ttc aac agc cac gac aaa act atg agt gga cac tta     720
Tyr Arg Gln Leu Phe Asn Ser His Asp Lys Thr Met Ser Gly His Leu
225                 230                 235                 240 aca ggt ccc cag gca aga act att ctc atg caa tca agt tta ccc cag     768
Thr Gly Pro Gln Ala Arg Thr Ile Leu Met Gln Ser Ser Leu Pro Gln
                245                 250                 255 gct cag ctg gct tca ata tgg aat ctt tct gac att gat caa gat gga     816
Ala Gln Leu Ala Ser Ile Trp Asn Leu Ser Asp Ile Asp Gln Asp Gly
            260                 265                 270 aaa ctc act gca gaa gaa ttt atc cta gct atg cac cta att gat gtt     864
Lys Leu Thr Ala Glu Glu Phe Ile Leu Ala Met His Leu Ile Asp Val
        275                 280                 285
```

```
gcc atg tct ggt cag cca ctg ccg ccc gtc ctg cct cca gaa tac atc      912
Ala Met Ser Gly Gln Pro Leu Pro Pro Val Leu Pro Pro Glu Tyr Ile
290                 295                 300 cct cct tcc ttc aga aga gtt cgc tcc ggc agt ggg atg tcc gtc ata      960
Pro Pro Ser Phe Arg Arg Val Arg Ser Gly Ser Gly Met Ser Val Ile
305                 310                 315                 320 agc tct tct tct gtg gat cag agg ctg cct gag gag ccg tcg tca gag     1008
Ser Ser Ser Ser Val Asp Gln Arg Leu Pro Glu Glu Pro Ser Ser Glu
                325                 330                 335 gat gag cag cag cca gag aag aaa ctg cct gtg aca ttt gaa gat aag     1056
Asp Glu Gln Gln Pro Glu Lys Lys Leu Pro Val Thr Phe Glu Asp Lys
    340                 345                 350 aag cgg gag aac ttc gag cga ggc agt gtg gag ctg gag aag cgc cgg     1104
Lys Arg Glu Asn Phe Glu Arg Gly Ser Val Glu Leu Glu Lys Arg Arg
355                 360                 365 caa gcg ctc ttg gag cag cag cgc aaa gag cag gag cgg ttg gct cag     1152
Gln Ala Leu Leu Glu Gln Gln Arg Lys Glu Gln Glu Arg Leu Ala Gln
370                 375                 380 ctg gag cgc gcc gag cag gag agg aaa gag cgg gag cgc cag gag cag     1200
Leu Glu Arg Ala Glu Gln Glu Arg Lys Glu Arg Glu Arg Gln Glu Gln
385                 390                 395                 400 gag gcc aag cgg cag ctg gag ctg gag aag cag ctg gag aag cag cgg     1248
Glu Ala Lys Arg Gln Leu Glu Leu Glu Lys Gln Leu Glu Lys Gln Arg
                405                 410                 415 gag ctg gag cgg cag cga gag gag gag agg agg aag gag atc gag agg     1296
Glu Leu Glu Arg Gln Arg Glu Glu Glu Arg Arg Lys Glu Ile Glu Arg
            420                 425                 430 cgc gag gcc gca aaa cgg gaa ctg gaa agg cag cga caa ctt gaa tgg     1344
Arg Glu Ala Ala Lys Arg Glu Leu Glu Arg Gln Arg Gln Leu Glu Trp
                435                 440                 445 gaa cgg aac cgg aga cag gaa ctc ctg aat cag agg aac aag gag cag     1392
Glu Arg Asn Arg Arg Gln Glu Leu Leu Asn Gln Arg Asn Lys Glu Gln
450                 455                 460 gag ggc acc gtg gtc ctg aag gca agg agg aag act ctg gag ttt gag     1440
Glu Gly Thr Val Val Leu Lys Ala Arg Arg Lys Thr Leu Glu Phe Glu
465                 470                 475                 480 tta gaa gct ctg aat gac aaa aag cat cag cta gaa gga aaa ctt cag     1488
Leu Glu Ala Leu Asn Asp Lys Lys His Gln Leu Glu Gly Lys Leu Gln
                485                 490                 495 gat atc agg tgt cga ctg gca acc cag agg caa gaa att gag agc acg     1536
Asp Ile Arg Cys Arg Leu Ala Thr Gln Arg Gln Glu Ile Glu Ser Thr
            500                 505                 510 aac aag tct aga gag cta aga att gct gaa atc acc cac tta cag cag     1584
Asn Lys Ser Arg Glu Leu Arg Ile Ala Glu Ile Thr His Leu Gln Gln
                515                 520                 525 cag ttg cag gaa tct cag caa atg ctt gga aga ctt att cca gag aaa     1632
Gln Leu Gln Glu Ser Gln Gln Met Leu Gly Arg Leu Ile Pro Glu Lys
530                 535                 540 cag ata ctc agt gac cag tta aaa caa gtc cag cag aac agt ttg cat     1680
Gln Ile Leu Ser Asp Gln Leu Lys Gln Val Gln Gln Asn Ser Leu His
545                 550                 555                 560 aga gac tcg ctt ctt acc ctc aaa aga gcc ttg gaa gca aag gag ctg     1728
Arg Asp Ser Leu Leu Thr Leu Lys Arg Ala Leu Glu Ala Lys Glu Leu
                565                 570                 575 gcc cgg cag cag ctc cgg gag cag ctg gac gag gtg gag aga gag acc     1776
Ala Arg Gln Gln Leu Arg Glu Gln Leu Asp Glu Val Glu Arg Glu Thr
            580                 585                 590 agg tca aag ctg cag gag att gat gtt ttc aac aac cag ctg aag gaa     1824
Arg Ser Lys Leu Gln Glu Ile Asp Val Phe Asn Asn Gln Leu Lys Glu
```

-continued

```
            595                 600                 605
ctg aga gag ata cat agc aaa cag caa ctc cag aag cag agg tcc ctg     1872
Leu Arg Glu Ile His Ser Lys Gln Gln Leu Gln Lys Gln Arg Ser Leu
    610                 615                 620 gag gca gcg cga ctg aag cag aaa gag cag gag agg aag agc ctg gag     1920
Glu Ala Arg Leu Lys Gln Lys Glu Gln Glu Arg Lys Ser Leu Glu
625                 630                 635                 640 tta gag aag caa aag gaa gac gct cag aga cga gtt cag gaa agg gac     1968
Leu Glu Lys Gln Lys Glu Asp Ala Gln Arg Arg Val Gln Glu Arg Asp
                645                 650                 655 aag caa tgg ctg gag cat gtg cag cag gag gag cag cca cgc ccc cgg     2016
Lys Gln Trp Leu Glu His Val Gln Gln Glu Glu Gln Pro Arg Pro Arg
            660                 665                 670 aaa ccc cac gag gag gac aga ctg aag agg gaa gac agt gtc agg aag     2064
Lys Pro His Glu Glu Asp Arg Leu Lys Arg Glu Asp Ser Val Arg Lys
        675                 680                 685 aag gag gcg gaa gag aga gcc aag ccg gaa atg caa gac aag cag agt     2112
Lys Glu Ala Glu Glu Arg Ala Lys Pro Glu Met Gln Asp Lys Gln Ser
    690                 695                 700 cgg ctt ttc cat ccg cat cag gag cca gct aag ctg gcc acc cag gca     2160
Arg Leu Phe His Pro His Gln Glu Pro Ala Lys Leu Ala Thr Gln Ala
705                 710                 715                 720 ccc tgg tct acc aca gag aaa ggc ccg ctt acc att tct gca cag gag     2208
Pro Trp Ser Thr Thr Glu Lys Gly Pro Leu Thr Ile Ser Ala Gln Glu
                725                 730                 735 agt gta aaa gtg gta tat tac cga gcg ctg tac ccc ttt gaa tcc aga     2256
Ser Val Lys Val Val Tyr Tyr Arg Ala Leu Tyr Pro Phe Glu Ser Arg
            740                 745                 750 agt cac gat gag atc acc atc cag cca gga gat ata gtc atg gtg gat     2304
Ser His Asp Glu Ile Thr Ile Gln Pro Gly Asp Ile Val Met Val Asp
        755                 760                 765 gaa agc cag act gga gag cca gga tgg ctt gga gga gag ctg aaa ggg     2352
Glu Ser Gln Thr Gly Glu Pro Gly Trp Leu Gly Gly Glu Leu Lys Gly
    770                 775                 780 aag acg gga tgg ttc cct gca aac tat gca gaa aag att cca gaa aat     2400
Lys Thr Gly Trp Phe Pro Ala Asn Tyr Ala Glu Lys Ile Pro Glu Asn
785                 790                 795                 800 gag gtt ccc act cca gcc aaa cca gtg acc gat ctg aca tct gcc cct     2448
Glu Val Pro Thr Pro Ala Lys Pro Val Thr Asp Leu Thr Ser Ala Pro
                805                 810                 815 gcc ccc aaa ctg gct ctg cgt gag acc cct gct cct ttg cca gtg acc     2496
Ala Pro Lys Leu Ala Leu Arg Glu Thr Pro Ala Pro Leu Pro Val Thr
            820                 825                 830 tct tct gag ccc tcc aca acc ccc aac aac tgg gca gac ttc agt tcc     2544
Ser Ser Glu Pro Ser Thr Thr Pro Asn Asn Trp Ala Asp Phe Ser Ser
        835                 840                 845 acg tgg ccc agc agc tca aac gag aag cca gaa acg gac aac tgg gat     2592
Thr Trp Pro Ser Ser Ser Asn Glu Lys Pro Glu Thr Asp Asn Trp Asp
    850                 855                 860 acg tgg gcg gct cag cct tct ctg acc gta cct agt gct ggc cag tta     2640
Thr Trp Ala Ala Gln Pro Ser Leu Thr Val Pro Ser Ala Gly Gln Leu
865                 870                 875                 880 cgg cag aga tca gcc ttt acc cca gcc aca gcc act ggc tcc tcc cca     2688
Arg Gln Arg Ser Ala Phe Thr Pro Ala Thr Ala Thr Gly Ser Ser Pro
                885                 890                 895 tct ccc gtc ctg ggc cag ggt gaa aag gtg gaa ggg cta caa gcg caa     2736
Ser Pro Val Leu Gly Gln Gly Glu Lys Val Glu Gly Leu Gln Ala Gln
            900                 905                 910 gcc ctg tat ccc tgg aga gcc aaa aaa gac aac cac tta aat ttt aac     2784
```

```
                     Ala Leu Tyr Pro Trp Arg Ala Lys Lys Asp Asn His Leu Asn Phe Asn
                             915                 920                 925 aaa agt gac gtc atc acc gtt ctg gaa cag caa gac atg tgg tgg ttt        2832
Lys Ser Asp Val Ile Thr Val Leu Glu Gln Gln Asp Met Trp Trp Phe
        930                 935                 940 gga gaa gtt caa ggt cag aag ggt tgg ttc ccc aag tct tac gtg aaa        2880
Gly Glu Val Gln Gly Gln Lys Gly Trp Phe Pro Lys Ser Tyr Val Lys
945                 950                 955                 960 ctc att tca ggg ccc gta agg aaa tcc aca agc atc gat act ggc cct        2928
Leu Ile Ser Gly Pro Val Arg Lys Ser Thr Ser Ile Asp Thr Gly Pro
                965                 970                 975 act gaa agt cct gct agt cta aag aga gtg gct tcc ccg gcc gcc aag        2976
Thr Glu Ser Pro Ala Ser Leu Lys Arg Val Ala Ser Pro Ala Ala Lys
        980                 985                 990 cca gcc att ccc gga gaa gag ttt att gcc atg tac aca tac gag agt        3024
Pro Ala Ile Pro Gly Glu Glu Phe Ile Ala Met Tyr Thr Tyr Glu Ser
                995                 1000                1005 tct gag caa gga gat tta acc ttt cag caa ggg gat gtg att gtg            3069
Ser Glu Gln Gly Asp Leu Thr Phe Gln Gln Gly Asp Val Ile Val
        1010                1015                1020 gtt acc aag aaa gat ggt gac tgg tgg acg gga acg gtg ggc gac            3114
Val Thr Lys Lys Asp Gly Asp Trp Trp Thr Gly Thr Val Gly Asp
        1025                1030                1035 aag tcc gga gtc ttc cct tct aac tat gtg agg ctt aaa gat tca            3159
Lys Ser Gly Val Phe Pro Ser Asn Tyr Val Arg Leu Lys Asp Ser
        1040                1045                1050 gag ggc tct gga act gct ggg aaa aca ggg agt tta gga aaa aaa            3204
Glu Gly Ser Gly Thr Ala Gly Lys Thr Gly Ser Leu Gly Lys Lys
        1055                1060                1065 cct gaa att gcc cag gtt att gct tcc tac gct gct act ggt ccc            3249
Pro Glu Ile Ala Gln Val Ile Ala Ser Tyr Ala Ala Thr Gly Pro
        1070                1075                1080 gaa caa ctc acc ctg gct cct ggg cag ctg att ctg atc cgg aaa            3294
Glu Gln Leu Thr Leu Ala Pro Gly Gln Leu Ile Leu Ile Arg Lys
        1085                1090                1095 aag aac cca ggt gga tgg tgg gaa gga gaa ctg caa gct cga ggg            3339
Lys Asn Pro Gly Gly Trp Trp Glu Gly Glu Leu Gln Ala Arg Gly
        1100                1105                1110 aaa aag cgc cag ata ggg tgg ttt cca gca aat tat gtc aaa ctt            3384
Lys Lys Arg Gln Ile Gly Trp Phe Pro Ala Asn Tyr Val Lys Leu
        1115                1120                1125 cta agc ccc gga aca agc aaa atc acc cca act gag cta ccc aag            3429
Leu Ser Pro Gly Thr Ser Lys Ile Thr Pro Thr Glu Leu Pro Lys
        1130                1135                1140 acc gca gtg cag cca gca gtg tgc cag gtg atc ggg atg tac gat            3474
Thr Ala Val Gln Pro Ala Val Cys Gln Val Ile Gly Met Tyr Asp
        1145                1150                1155 tac acc gcc cag aac gat gac gaa cta gcc ttc agc aaa ggc cag            3519
Tyr Thr Ala Gln Asn Asp Asp Glu Leu Ala Phe Ser Lys Gly Gln
        1160                1165                1170 atc atc aac gtc ctc aac aag gag gac ccg gac tgg tgg aaa gga            3564
Ile Ile Asn Val Leu Asn Lys Glu Asp Pro Asp Trp Trp Lys Gly
        1175                1180                1185 gaa gtc agt ggg caa gtt ggg ctc ttc cca tcc aat tat gta aag            3609
Glu Val Ser Gly Gln Val Gly Leu Phe Pro Ser Asn Tyr Val Lys
        1190                1195                1200 ctg acc aca gac atg gac ccc agc cag caa tgg tgc tca gac ctg            3654
Leu Thr Thr Asp Met Asp Pro Ser Gln Gln Trp Cys Ser Asp Leu
        1205                1210                1215
```

```
cat ctc tta gat atg ctg acc ccg act gag agg aag cgg caa ggc    3699
His Leu Leu Asp Met Leu Thr Pro Thr Glu Arg Lys Arg Gln Gly
    1220            1225                1230 tac atc cat gaa ctc att gtc acg gag gag aac tac gtg aac gac    3744
Tyr Ile His Glu Leu Ile Val Thr Glu Glu Asn Tyr Val Asn Asp
1235            1240                1245 ttg cag ctg gtc aca gag atc ttt cag aaa ccc ctg acg gag tct    3789
Leu Gln Leu Val Thr Glu Ile Phe Gln Lys Pro Leu Thr Glu Ser
    1250            1255                1260 gag ctg ctg aca gaa aaa gag gtt gct atg att ttt gtt aac tgg    3834
Glu Leu Leu Thr Glu Lys Glu Val Ala Met Ile Phe Val Asn Trp
    1265            1270                1275 aag gag ctg atc atg tgt aat atc aaa ctg ctg aaa gcg ctg aga    3879
Lys Glu Leu Ile Met Cys Asn Ile Lys Leu Leu Lys Ala Leu Arg
    1280            1285                1290 gtc cgc aag aag atg tct ggg gag aag atg ccg gtg aag atg att    3924
Val Arg Lys Lys Met Ser Gly Glu Lys Met Pro Val Lys Met Ile
    1295            1300                1305 ggc gac atc ctg agc gcc cag ctg ccg cac atg cag cct tac atc    3969
Gly Asp Ile Leu Ser Ala Gln Leu Pro His Met Gln Pro Tyr Ile
    1310            1315                1320 cgc ttc tgc agc tgc cag ctc aat ggg gct gcc ctc atc cag cag    4014
Arg Phe Cys Ser Cys Gln Leu Asn Gly Ala Ala Leu Ile Gln Gln
    1325            1330                1335 aag acg gac gag gct cca gac ttc aag gag ttc gtc aaa aga ctg    4059
Lys Thr Asp Glu Ala Pro Asp Phe Lys Glu Phe Val Lys Arg Leu
    1340            1345                1350 gca atg gac cct cgg tgc aaa gga atg cct ctg tcc agc ttt ata    4104
Ala Met Asp Pro Arg Cys Lys Gly Met Pro Leu Ser Ser Phe Ile
    1355            1360                1365 ctg aag cct atg cag cgt gtc aca aga tac ccg ctg atc att aaa    4149
Leu Lys Pro Met Gln Arg Val Thr Arg Tyr Pro Leu Ile Ile Lys
    1370            1375                1380 aac atc ctg gaa aac act cct gag aac cat cca gac cac agc cac    4194
Asn Ile Leu Glu Asn Thr Pro Glu Asn His Pro Asp His Ser His
    1385            1390                1395 ctg aag cat gcc ctg gaa aag gcg gag gag ctg tgc tcc cag gtg    4239
Leu Lys His Ala Leu Glu Lys Ala Glu Glu Leu Cys Ser Gln Val
    1400            1405                1410 aac gag gga gtt cga gag aag gag aac tca gac cgg ctg gag tgg    4284
Asn Glu Gly Val Arg Glu Lys Glu Asn Ser Asp Arg Leu Glu Trp
    1415            1420                1425 atc caa gcc cac gtg cag tgt gaa ggc ctt tct gag caa ctg gtg    4329
Ile Gln Ala His Val Gln Cys Glu Gly Leu Ser Glu Gln Leu Val
    1430            1435                1440 ttc aat tca gtg acc aac tgc ttg gga cca cgc aag ttt ctg cac    4374
Phe Asn Ser Val Thr Asn Cys Leu Gly Pro Arg Lys Phe Leu His
    1445            1450                1455 agc ggg aag ctc tac aag gcc aag agc aat aaa gaa ctg tat ggc    4419
Ser Gly Lys Leu Tyr Lys Ala Lys Ser Asn Lys Glu Leu Tyr Gly
    1460            1465                1470 ttc ctc ttc aac gac ttc ctc ctg ctg acc caa atc aca aag ccc    4464
Phe Leu Phe Asn Asp Phe Leu Leu Leu Thr Gln Ile Thr Lys Pro
    1475            1480                1485 tta ggc tct tcc ggc acc gac aaa gtc ttc agc ccc aaa tct aac    4509
Leu Gly Ser Ser Gly Thr Asp Lys Val Phe Ser Pro Lys Ser Asn
    1490            1495                1500 ctt cag tat aaa atg tac aaa acg ccc att ttc tta aat gag gtt    4554
Leu Gln Tyr Lys Met Tyr Lys Thr Pro Ile Phe Leu Asn Glu Val
    1505            1510                1515
```

```
cta gta aaa ttg ccc acg gac cct tct gga gat gag cct atc ttc      4599
Leu Val Lys Leu Pro Thr Asp Pro Ser Gly Asp Glu Pro Ile Phe
    1520                1525                1530 cac att tcc cac atc gac cgg gtc tac acc ctc cga gca gag agc      4644
His Ile Ser His Ile Asp Arg Val Tyr Thr Leu Arg Ala Glu Ser
1535                1540                1545 ata aat gag agg act gcc tgg gtg cag aaa atc aag gcg gcg tct      4689
Ile Asn Glu Arg Thr Ala Trp Val Gln Lys Ile Lys Ala Ala Ser
    1550                1555                1560 gag ctc tac ata gag acg gag aaa aag aag cga gag aag gcg tac      4734
Glu Leu Tyr Ile Glu Thr Glu Lys Lys Lys Arg Glu Lys Ala Tyr
    1565                1570                1575 ctg gtc cgt tcc cag cgg gcg acc ggt att gga agg ttg atg gtg      4779
Leu Val Arg Ser Gln Arg Ala Thr Gly Ile Gly Arg Leu Met Val
    1580                1585                1590 aac gtg gta gaa ggc att gag ctg aag ccc tgt cgg tca cat gga      4824
Asn Val Val Glu Gly Ile Glu Leu Lys Pro Cys Arg Ser His Gly
    1595                1600                1605 aag agc aac ccg tac tgt gag gtg acc atg ggc tct cag tgc cac      4869
Lys Ser Asn Pro Tyr Cys Glu Val Thr Met Gly Ser Gln Cys His
    1610                1615                1620 atc acc aag aca atc cag gac acg cta aac ccc aag tgg aat tct      4914
Ile Thr Lys Thr Ile Gln Asp Thr Leu Asn Pro Lys Trp Asn Ser
    1625                1630                1635 aac tgc cag ttc ttc atc aga gac ctg gag cag gag gtt ctc tgc      4959
Asn Cys Gln Phe Phe Ile Arg Asp Leu Glu Gln Glu Val Leu Cys
    1640                1645                1650 atc aca gtg ttt gag agg gac cag ttc tcg cct gat gat ttt ttg      5004
Ile Thr Val Phe Glu Arg Asp Gln Phe Ser Pro Asp Asp Phe Leu
    1655                1660                1665 ggt cgg aca gag atc cga gtg gcc gac atc aag aaa gac cag ggc      5049
Gly Arg Thr Glu Ile Arg Val Ala Asp Ile Lys Lys Asp Gln Gly
    1670                1675                1680 tcc aag ggg ccg gtt acg aag tgt ctc ctg ctg cat gag gtc ccc      5094
Ser Lys Gly Pro Val Thr Lys Cys Leu Leu Leu His Glu Val Pro
    1685                1690                1695 acg gga gag att gtg gtc cgc ctt gac ctg cag ttg ttt gat gag      5139
Thr Gly Glu Ile Val Val Arg Leu Asp Leu Gln Leu Phe Asp Glu
    1700                1705                1710 ccg tag                                                          5145
Pro

<210> SEQ ID NO 24
<211> LENGTH: 1714
<212> TYPE: PRT
<213> ORGANISM: Mus musculus

<400> SEQUENCE: 24

Met Ala Gln Phe Pro Thr Pro Phe Gly Gly Ser Leu Asp Val Trp Ala
1               5                   10                  15

Ile Thr Val Glu Glu Arg Ala Lys His Asp Gln Gln Phe Leu Ser Leu
            20                  25                  30

Lys Pro Ile Ala Gly Phe Ile Thr Gly Asp Gln Ala Arg Asn Phe Phe
        35                  40                  45

Phe Gln Ser Gly Leu Pro Gln Pro Val Leu Ala Gln Ile Trp Ala Leu
    50                  55                  60

Ala Asp Met Asn Asn Asp Gly Arg Met Asp Gln Val Glu Phe Ser Ile
65                  70                  75                  80
```

-continued

```
Ala Met Lys Leu Ile Lys Leu Lys Leu Gln Gly Tyr Gln Leu Pro Ser
            85                  90                  95
Thr Leu Pro Pro Val Met Lys Gln Gln Pro Val Ala Ile Ser Ser Ala
            100                 105                 110
Pro Ala Phe Gly Ile Gly Gly Ile Ala Ser Met Pro Pro Leu Thr Ala
            115                 120                 125
Val Ala Pro Val Pro Met Gly Ser Ile Pro Val Gly Met Ser Pro
130                 135                 140
Pro Leu Val Ser Ser Val Pro Ala Ala Val Pro Pro Leu Ala Asn
145                 150                 155                 160
Gly Ala Pro Pro Val Ile Gln Pro Leu Pro Ala Phe Ala His Pro Ala
            165                 170                 175
Ala Thr Trp Pro Lys Ser Ser Ser Phe Ser Arg Ser Gly Pro Gly Ser
            180                 185                 190
Gln Leu Asn Thr Lys Leu Gln Lys Ala Gln Ser Phe Asp Val Ala Ser
            195                 200                 205
Ala Pro Pro Ala Ala Glu Trp Ala Val Pro Gln Ser Ser Arg Leu Lys
            210                 215                 220
Tyr Arg Gln Leu Phe Asn Ser His Asp Lys Thr Met Ser Gly His Leu
225                 230                 235                 240
Thr Gly Pro Gln Ala Arg Thr Ile Leu Met Gln Ser Ser Leu Pro Gln
            245                 250                 255
Ala Gln Leu Ala Ser Ile Trp Asn Leu Ser Asp Ile Asp Gln Asp Gly
            260                 265                 270
Lys Leu Thr Ala Glu Glu Phe Ile Leu Ala Met His Leu Ile Asp Val
            275                 280                 285
Ala Met Ser Gly Gln Pro Leu Pro Pro Val Leu Pro Pro Glu Tyr Ile
            290                 295                 300
Pro Pro Ser Phe Arg Arg Val Arg Ser Gly Ser Gly Met Ser Val Ile
305                 310                 315                 320
Ser Ser Ser Ser Val Asp Gln Arg Leu Pro Glu Pro Ser Ser Glu
            325                 330                 335
Asp Glu Gln Gln Pro Glu Lys Lys Leu Pro Val Thr Phe Glu Asp Lys
            340                 345                 350
Lys Arg Glu Asn Phe Glu Arg Gly Ser Val Glu Leu Glu Lys Arg Arg
            355                 360                 365
Gln Ala Leu Leu Glu Gln Gln Arg Lys Glu Gln Glu Arg Leu Ala Gln
            370                 375                 380
Leu Glu Arg Ala Glu Gln Gln Arg Lys Glu Arg Glu Arg Gln Glu Gln
385                 390                 395                 400
Glu Ala Lys Arg Gln Leu Glu Leu Glu Lys Gln Leu Glu Lys Gln Arg
            405                 410                 415
Glu Leu Glu Arg Gln Arg Glu Glu Arg Lys Glu Ile Glu Arg
            420                 425                 430
Arg Glu Ala Ala Lys Arg Glu Leu Glu Arg Gln Arg Gln Leu Glu Trp
            435                 440                 445
Glu Arg Asn Arg Arg Gln Glu Leu Leu Asn Gln Arg Asn Lys Glu Gln
            450                 455                 460
Glu Gly Thr Val Val Leu Lys Ala Arg Arg Lys Thr Leu Glu Phe Glu
465                 470                 475                 480
Leu Glu Ala Leu Asn Asp Lys Lys His Gln Leu Glu Gly Lys Leu Gln
            485                 490                 495
Asp Ile Arg Cys Arg Leu Ala Thr Gln Arg Gln Glu Ile Glu Ser Thr
```

-continued

```
                500              505              510
Asn Lys Ser Arg Glu Leu Arg Ile Ala Glu Ile Thr His Leu Gln Gln
        515                  520                  525
Gln Leu Gln Glu Ser Gln Gln Met Leu Gly Arg Leu Ile Pro Glu Lys
    530                  535                  540
Gln Ile Leu Ser Asp Gln Leu Lys Gln Val Gln Gln Asn Ser Leu His
545                  550                  555                  560
Arg Asp Ser Leu Leu Thr Leu Lys Arg Ala Leu Glu Ala Lys Glu Leu
                565                  570                  575
Ala Arg Gln Gln Leu Arg Glu Gln Leu Asp Glu Val Glu Arg Glu Thr
            580                  585                  590
Arg Ser Lys Leu Gln Glu Ile Asp Val Phe Asn Asn Gln Leu Lys Glu
        595                  600                  605
Leu Arg Glu Ile His Ser Lys Gln Gln Leu Gln Lys Gln Arg Ser Leu
    610                  615                  620
Glu Ala Ala Arg Leu Lys Gln Lys Glu Gln Arg Lys Ser Leu Glu
625                  630                  635                  640
Leu Glu Lys Gln Lys Glu Asp Ala Gln Arg Arg Val Gln Glu Arg Asp
                645                  650                  655
Lys Gln Trp Leu Glu His Val Gln Gln Glu Gln Pro Arg Pro Arg
            660                  665                  670
Lys Pro His Glu Glu Asp Arg Leu Arg Glu Asp Ser Val Arg Lys
        675                  680                  685
Lys Glu Ala Glu Glu Arg Ala Lys Pro Glu Met Gln Asp Lys Gln Ser
    690                  695                  700
Arg Leu Phe His Pro His Gln Glu Pro Ala Lys Leu Ala Thr Gln Ala
705                  710                  715                  720
Pro Trp Ser Thr Thr Glu Lys Gly Pro Leu Thr Ile Ser Ala Gln Glu
                725                  730                  735
Ser Val Lys Val Val Tyr Tyr Arg Ala Leu Tyr Pro Phe Glu Ser Arg
            740                  745                  750
Ser His Asp Glu Ile Thr Ile Gln Pro Gly Asp Ile Val Met Val Asp
        755                  760                  765
Glu Ser Gln Thr Gly Glu Pro Gly Trp Leu Gly Gly Glu Leu Lys Gly
    770                  775                  780
Lys Thr Gly Trp Phe Pro Ala Asn Tyr Ala Glu Lys Ile Pro Glu Asn
785                  790                  795                  800
Glu Val Pro Thr Pro Ala Lys Pro Val Thr Asp Leu Thr Ser Ala Pro
                805                  810                  815
Ala Pro Lys Leu Ala Leu Arg Glu Thr Pro Ala Pro Leu Pro Val Thr
            820                  825                  830
Ser Ser Glu Pro Ser Thr Thr Pro Asn Asn Trp Ala Asp Phe Ser Ser
        835                  840                  845
Thr Trp Pro Ser Ser Asn Glu Lys Pro Glu Thr Asp Asn Trp Asp
    850                  855                  860
Thr Trp Ala Ala Gln Pro Ser Leu Thr Val Pro Ser Ala Gly Gln Leu
865                  870                  875                  880
Arg Gln Arg Ser Ala Phe Thr Pro Ala Thr Ala Thr Gly Ser Ser Pro
                885                  890                  895
Ser Pro Val Leu Gly Gln Gly Glu Lys Val Glu Gly Leu Gln Ala Gln
            900                  905                  910
Ala Leu Tyr Pro Trp Arg Ala Lys Lys Asp Asn His Leu Asn Phe Asn
        915                  920                  925
```

```
Lys Ser Asp Val Ile Thr Val Leu Glu Gln Gln Asp Met Trp Trp Phe
    930                 935                 940

Gly Glu Val Gln Gly Gln Lys Gly Trp Phe Pro Lys Ser Tyr Val Lys
945                 950                 955                 960

Leu Ile Ser Gly Pro Val Arg Lys Ser Thr Ser Ile Asp Thr Gly Pro
                965                 970                 975

Thr Glu Ser Pro Ala Ser Leu Arg Val Ala Ser Pro Ala Ala Lys
            980                 985                 990

Pro Ala Ile Pro Gly Glu Glu Phe Ile Ala Met Tyr Thr Tyr Glu Ser
        995                 1000                1005

Ser Glu Gln Gly Asp Leu Thr Phe Gln Gln Gly Asp Val Ile Val
    1010                1015                1020

Val Thr Lys Lys Asp Gly Asp Trp Trp Thr Gly Thr Val Gly Asp
    1025                1030                1035

Lys Ser Gly Val Phe Pro Ser Asn Tyr Val Arg Leu Lys Asp Ser
    1040                1045                1050

Glu Gly Ser Gly Thr Ala Gly Lys Thr Gly Ser Leu Gly Lys Lys
    1055                1060                1065

Pro Glu Ile Ala Gln Val Ile Ala Ser Tyr Ala Ala Thr Gly Pro
    1070                1075                1080

Glu Gln Leu Thr Leu Ala Pro Gly Gln Leu Ile Leu Ile Arg Lys
    1085                1090                1095

Lys Asn Pro Gly Gly Trp Trp Glu Gly Glu Leu Gln Ala Arg Gly
    1100                1105                1110

Lys Lys Arg Gln Ile Gly Trp Phe Pro Ala Asn Tyr Val Lys Leu
    1115                1120                1125

Leu Ser Pro Gly Thr Ser Lys Ile Thr Pro Thr Glu Leu Pro Lys
    1130                1135                1140

Thr Ala Val Gln Pro Ala Val Cys Gln Val Ile Gly Met Tyr Asp
    1145                1150                1155

Tyr Thr Ala Gln Asn Asp Asp Glu Leu Ala Phe Ser Lys Gly Gln
    1160                1165                1170

Ile Ile Asn Val Leu Asn Lys Glu Asp Pro Asp Trp Trp Lys Gly
    1175                1180                1185

Glu Val Ser Gly Gln Val Gly Leu Phe Pro Ser Asn Tyr Val Lys
    1190                1195                1200

Leu Thr Thr Asp Met Asp Pro Ser Gln Gln Trp Cys Ser Asp Leu
    1205                1210                1215

His Leu Leu Asp Met Leu Thr Pro Thr Glu Arg Lys Arg Gln Gly
    1220                1225                1230

Tyr Ile His Glu Leu Ile Val Thr Glu Glu Asn Tyr Val Asn Asp
    1235                1240                1245

Leu Gln Leu Val Thr Glu Ile Phe Gln Lys Pro Leu Thr Glu Ser
    1250                1255                1260

Glu Leu Leu Thr Glu Lys Glu Val Ala Met Ile Phe Val Asn Trp
    1265                1270                1275

Lys Glu Leu Ile Met Cys Asn Ile Lys Leu Leu Lys Ala Leu Arg
    1280                1285                1290

Val Arg Lys Lys Met Ser Gly Glu Lys Met Pro Val Lys Met Ile
    1295                1300                1305

Gly Asp Ile Leu Ser Ala Gln Leu Pro His Met Gln Pro Tyr Ile
    1310                1315                1320
```

-continued

```
Arg Phe Cys Ser Cys Gln Leu Asn Gly Ala Ala Leu Ile Gln Gln
1325                1330                1335

Lys Thr Asp Glu Ala Pro Asp Phe Lys Glu Phe Val Lys Arg Leu
    1340                1345                1350

Ala Met Asp Pro Arg Cys Lys Gly Met Pro Leu Ser Ser Phe Ile
    1355                1360                1365

Leu Lys Pro Met Gln Arg Val Thr Arg Tyr Pro Leu Ile Ile Lys
    1370                1375                1380

Asn Ile Leu Glu Asn Thr Pro Glu Asn His Pro Asp His Ser His
    1385                1390                1395

Leu Lys His Ala Leu Glu Lys Ala Glu Glu Leu Cys Ser Gln Val
    1400                1405                1410

Asn Glu Gly Val Arg Glu Lys Glu Asn Ser Asp Arg Leu Glu Trp
    1415                1420                1425

Ile Gln Ala His Val Gln Cys Glu Gly Leu Ser Glu Gln Leu Val
    1430                1435                1440

Phe Asn Ser Val Thr Asn Cys Leu Gly Pro Arg Lys Phe Leu His
    1445                1450                1455

Ser Gly Lys Leu Tyr Lys Ala Lys Ser Asn Lys Glu Leu Tyr Gly
    1460                1465                1470

Phe Leu Phe Asn Asp Phe Leu Leu Leu Thr Gln Ile Thr Lys Pro
    1475                1480                1485

Leu Gly Ser Ser Gly Thr Asp Lys Val Phe Ser Pro Lys Ser Asn
    1490                1495                1500

Leu Gln Tyr Lys Met Tyr Lys Thr Pro Ile Phe Leu Asn Glu Val
    1505                1510                1515

Leu Val Lys Leu Pro Thr Asp Pro Ser Gly Asp Glu Pro Ile Phe
    1520                1525                1530

His Ile Ser His Ile Asp Arg Val Tyr Thr Leu Arg Ala Glu Ser
    1535                1540                1545

Ile Asn Glu Arg Thr Ala Trp Val Gln Lys Ile Lys Ala Ala Ser
    1550                1555                1560

Glu Leu Tyr Ile Glu Thr Glu Lys Lys Lys Arg Glu Lys Ala Tyr
    1565                1570                1575

Leu Val Arg Ser Gln Arg Ala Thr Gly Ile Gly Arg Leu Met Val
    1580                1585                1590

Asn Val Val Glu Gly Ile Glu Leu Lys Pro Cys Arg Ser His Gly
    1595                1600                1605

Lys Ser Asn Pro Tyr Cys Glu Val Thr Met Gly Ser Gln Cys His
    1610                1615                1620

Ile Thr Lys Thr Ile Gln Asp Thr Leu Asn Pro Lys Trp Asn Ser
    1625                1630                1635

Asn Cys Gln Phe Phe Ile Arg Asp Leu Glu Gln Glu Val Leu Cys
    1640                1645                1650

Ile Thr Val Phe Glu Arg Asp Gln Phe Ser Pro Asp Asp Phe Leu
    1655                1660                1665

Gly Arg Thr Glu Ile Arg Val Ala Asp Ile Lys Lys Asp Gln Gly
    1670                1675                1680

Ser Lys Gly Pro Val Thr Lys Cys Leu Leu Leu His Glu Val Pro
    1685                1690                1695

Thr Gly Glu Ile Val Val Arg Leu Asp Leu Gln Leu Phe Asp Glu
    1700                1705                1710

Pro
```

<210> SEQ ID NO 25
<211> LENGTH: 6014
<212> TYPE: DNA
<213> ORGANISM: Mus musculus

<400> SEQUENCE: 25

```
cccttccttt cctttttttg tgttcgcctt cggccgtgcc ggctgagagc ccagcagccg      60
tgacaggctg cgcaacaggt tcgctgcggc cggcctgacg actgacccgg cggcggcggc     120
cgcggcacgg cagggtcttc ccggagcttg gccgcgccca cgcgccggtg tcgaggagcg     180
cgcggggtcg cgccgggacg tgcgcgaggc gccagatggc tgagagctgc aagaagaagt     240
caggatcatg atggctcagt ttcccacagc gatgaatgga gggccaaata tgtgggctat     300
tacatctgaa gaacgtacta agcatgataa acagtttgat aacctcaaac cttcaggagg     360
ttacataaca ggtgatcaag cccgtacttt tttcctacag tcaggtctgc cggcccggt      420
tttagctgaa atatgggcct tatcagatct gaacaaggat gggaagatgg accagcaaga     480
gttctctata gctatgaaac tcatcaagtt aaagttgcag gccaacagc tgcctgtagt       540
cctccctcct atcatgaaac aaccccctat gttctctcca ctaatctctg ctcgttttgg     600
gatgggaagc atgcccaatc tgtccattca tcagccattg cctccagttg cacctatagc     660
aacacccttg tcttctgcta cgtcagggac cagtattcct cccctaatga tgcctgctcc     720
cctagtgcct tctgttagta catcctcatt accaaatgga actgccagtc tcattcagcc     780
tttatccatt ccttattctt cttcaacatt gcctcatgca tcatcttaca gcctgatgat     840
gggaggattt ggtggtgcta gtatccagaa ggcccagtct ctgattgatt taggatctag     900
tagctcaact tcctcaactg cttccctctc agggaactca cctaagacag ggacctcaga     960
gtgggcagtt cctcagcctt caagattaaa gtatcggcaa aaatttaata gtctagacaa    1020
aggcatgagc ggatacctct caggtttttca agctagaaat gcccttcttc agtcaaatct    1080
ctctcaaact cagctagcta ctatttggac tctggctgac atcgatggtg acggacagtt    1140
gaaagctgaa gaatttattc tggcgatgca cctcactgac atggccaaag ctggacagcc    1200
actaccactg acgttgcctc ccgagcttgt ccctccatct ttcagagggg gaaagcaagt    1260
tgattctgtt aatggaactc tgccttcata tcagaaaaca caagaagaag agcctcagaa    1320
gaaactgcca gttacttttg aggacaaacg gaaagccaac tatgaacgag gaaacatgga    1380
gctggagaag cgacgccaag tgttgatgga gcagcagcag agggaggctg aacgcaaagc    1440
ccagaaagag aaggaagagt gggagcggaa acagagagaa ctgcaagagc aagaatggaa    1500
gaagcagctg gagttggaga aacgcttgga gaaacagaga gagctggaga cagcgggga    1560
ggaagagagg agaaaggaga tagaaagacg agaggcagca aaacaggagc ttgagagaca    1620
acgccgttta gaatgggaaa gactccgtcg gcaggagctg ctcagtcaga agaccaggga    1680
acaagaagac attgtcaggc tgagctccag aaagaaaagt ctccacctgg aactggaagc    1740
agtgaatgga aaacatcagc agatctcagg cagactacaa gatgtccaaa tcagaaagca    1800
aacacaaaag actgagctag aagttttgga taaacagtgt gacctggaaa ttatggaaat    1860
caaacaactt caacaagagc ttaaggaata tcaaaataag cttatctatc tggtccctga    1920
gaagcagcta ttaaacgaaa gaattaaaaa catgcagctc agtaacacac ctgattcagg    1980
gatcagttta cttcataaaa agtcatcaga aaaggaagaa ttatgccaaa gacttaaaga    2040
acaattagat gctcttgaaa aagaaactgc atctaagctc tcagaaatgg attcatttaa    2100
```

-continued

```
caatcagctg aaggaactca gagaaagcta taatacacag cagttagccc ttgaacaact      2160
tcataaaatc aaacgtgaca aattgaagga aatcgaaaga aaaagattag agcaaattca      2220
aaaaaagaaa ctagaagatg aggctgcaag gaaagcaaag caaggaaaag aaaacttgtg      2280
gagagaaagt attagaaagg aagaagagga aaagcaaaaa cgactccagg aagaaaagtc      2340
acaggacaaa actcaagaag aggaacgaaa agctgaggca aaacaaagtg agacagccag      2400
tgctttggtg aattacagag cactgtaccc ttttgaagca agaaaccatg atgagatgag      2460
ttttagttct ggggatataa ttcaggttga tgaaaaaact gtaggagagc ctggttggct      2520
ttatggtagt tttcagggaa agtttggctg gttcccctgc aactatgtag aaaaagtgct      2580
gtcaagtgaa aaagctctgt ctcctaagaa ggccttactt cctcctacag tgtctctctc      2640
tgctacctca acttcttccc agccaccagc atcagtgact gattatcaca atgtatcctt      2700
ctcaaacctt actgttaata caacatggca gcagaagtca gcttttaccc gcactgtgtc      2760
ccctggatct gtgtccccca ttcacggaca ggggcaggct gtagaaaacc tgaaagccca      2820
ggccctttgt tcctggacgg caaagaagga gaaccacctg aacttctcaa agcacgacgt      2880
catcactgtc ctggagcagc aggaaaaactg gtggtttggg gaggtgcacg gaggaagagg      2940
atggttcccc aagtcttatg tcaagctcat tcctgggaat gaagtacagc gaggagagcc      3000
agaagctttg tatgcagctg tgactaagaa acctacctcc acagcctatc agttacctc      3060
cacagcctat ccagttggag aagactacat tgcactttat tcatactcaa gtgtagagcc      3120
cggggatttg actttcactg aaggtgaaga aattctagtg acccagaaag atggagagtg      3180
gtggacagga agtattggag agagaactgg aatcttcccg tccaactacg tcagaccaaa      3240
ggatcaagaa aattttggga atgctagcaa atctggagca tcaaacaaaa aacccgagat      3300
cgctcaagta acttcagcat atgctgcttc agggactgag cagctcagcc ttgcgccagg      3360
acagttaata ttaatcttaa agaaaaacac aagcgggtgg tggcaaggag agctacaggc      3420
cagagggaag aaacgacaga agggatggtt tcctgccagc catgtaaagc tgctaggtcc      3480
aagcagtgaa agaaccatgc ctactttca cgctgtatgt caagtgattg ctatgtatga      3540
ctacatggcg aataacgaag atgagctcaa tttctccaaa ggacagctga ttaatgttat      3600
gaacaaagat gaccctgact ggtggcaagg agaaaccaat ggtctgactg gtctcttcc      3660
ttcaaactat gttaagatga caacagactc agatccaagt caacagtggt gtgctgacct      3720
ccaagccctg gacacaatgc agcctacgga gaggaagcga cagggctaca ttcacgagct      3780
cattcagaca gaggagcggt acatggacga cgacctgcag ctggtcatcg aggtcttcca      3840
gaaacgatg gctgaggaag gcttcctcac tgaagcagac atggctctga tctttgtgaa      3900
ctggaaagag ctcatcatgt ccaacacgaa gctgctgagg gccttgcggg tgaggaagaa      3960
gactgggggt gagaagatgc cagttcagat gattggagac atcctggcgg cagagctgtc      4020
ccacatgcag gcctacatcc gcttctgcag ctgtcagctt aatggggcaa ccctgttaca      4080
gcagaagaca gacgaggaca cggacttcaa ggaatttcta agaagttgg catcagaccc      4140
acgatgcaaa gggatgcccc tctccagctt cctgctgaag cccatgcaga ggatcactcg      4200
ctacccgctg ctcatccgaa gtatcctgga gaacactcca cagagtcatg ttgaccactc      4260
ctccctgaag ctgccctag aacgtgctga ggagctgtgc tctcaggtga acagggagt      4320
ccgggagaag gaaaattcag accggctgga gtggatccag gcacacgtgc agtgcgaagg      4380
cttggcagag caacttattt tcaactccct caccaactgc ctgggccccc ggaagcttct      4440
gcacagcggg aagctgtaca agaccaagag caataaggag ctgcacgcct tcctcttcaa      4500
```

-continued

```
cgacttcctg ctgctcacct acctggtcag gcagtttgcc gccgcctctg gccacgagaa    4560
gctcttcaac tccaagtcca gtgctcagtt ccggatgtac aaaacgccca ttttcctgaa    4620
tgaagtgttg gtgaaacttc ccacagaccc ttccggcgat gagcccgtct tccacatttc    4680
ccacattgat cgtgtgtaca cactccgaac agacaacatc aacgagagga cggcctgggt    4740
ccagaagatc aagggtgcct cagagcagta catcgacact gagaagaaga acgggaaaa    4800 ggcttaccaa gcccgttctc aaaagacttc aggtattggg cgtctgatgg tgcatgtcat    4860
tgaagctaca gaattaaaag cctgcaaacc aaacgggaaa agtaatccat actgtgaagt    4920
cagcatgggc tcccaaagct ataccaccag gaccctgcag gacacactaa accccaagtg    4980
gaacttcaac tgccagttct tcatcaagga tctttaccag gacgttctgt gtctcactat    5040
gtttgacaga gaccagtttt ctccagatga cttcttgggt cgtactgaag ttccagtggc    5100
aaaaatccga acagaacagg aaagcaaagg ccccaccacc cgccgactac tactgcacga    5160
agtccccact ggagaagtct gggtccgctt tgacctgcaa cttttttgaac aaaaaactct    5220 cctttgaggg cctggggaag ccagaaccag gggagctgcc cacaaggctg ggtctaaaga    5280
cagattttgc tctcccagga cagaggagca tcacatggct tcatccatca aacagccaca    5340
ctcgctgggc ctgtatttta ttgcacacta aattgctagc aatctatgca acatgatct    5400 tttaaacaaa cgccacagca cagtgccttg tactagtgtt aacctgttca gctgtgttag    5460
atgccagggt ttccattttc agggctataa agtattatg tggaaatgag gcatcagacc    5520
accggacgtt accacttggc aaatctgtcc actgtggagt tggtgatgtt ggaaccattc    5580
cacactatgt gacctctgct gggtcacaca ctcaggaggt gaagggctga gatgaaatgc    5640
tgcagccttg gggcttgtgc agcctgatac tgaaatagca tccacttgtg cactgaataa    5700
atagaaactt gatcgtttta ttctgactag atattatcat tctctgctaa gacaatatag    5760
tttgaaatat tatagtttga atataaggag gaaagcttga tgtactttaa atatactgtg    5820
aactctaata atgtggggat attttttcaac tttaattttc ttaagtataa attatttatg    5880
taaattcttt gttttgcata tttcatagaa catgcatctt taagctttat cattgccaac    5940
aatgtacaga aagagaataa agtataagt ttatgaatgt aaaaaaaaaa aaaaaaaaa    6000 aaaaaaaaaa aaaa                                                       6014
```

<210> SEQ ID NO 26
<211> LENGTH: 4977
<212> TYPE: DNA
<213> ORGANISM: Mus musculus
<220> FEATURE:
<221> NAME/KEY: CDS
<222> LOCATION: (1)..(4977)
<223> OTHER INFORMATION: Mouse Ese2L

<400> SEQUENCE: 26

```
atg gct cag ttt ccc aca gcg atg aat gga ggg cca aat atg tgg gct      48
Met Ala Gln Phe Pro Thr Ala Met Asn Gly Gly Pro Asn Met Trp Ala
1               5                   10                  15 att aca tct gaa gaa cgt act aag cat gat aaa cag ttt gat aac ctc      96
Ile Thr Ser Glu Glu Arg Thr Lys His Asp Lys Gln Phe Asp Asn Leu
                20                  25                  30 aaa cct tca gga ggt tac ata aca ggt gat caa gcc cgt act ttt ttc     144
Lys Pro Ser Gly Gly Tyr Ile Thr Gly Asp Gln Ala Arg Thr Phe Phe
            35                  40                  45 cta cag tca ggt ctg ccg gcc ccg gtt tta gct gaa ata tgg gcc tta     192
Leu Gln Ser Gly Leu Pro Ala Pro Val Leu Ala Glu Ile Trp Ala Leu
```

```
              50                  55                  60
tca gat ctg aac aag gat ggg aag atg gac cag caa gag ttc tct ata    240
Ser Asp Leu Asn Lys Asp Gly Lys Met Asp Gln Gln Glu Phe Ser Ile
 65                  70                  75                  80 gct atg aaa ctc atc aag tta aag ttg cag ggc caa cag ctg cct gta    288
Ala Met Lys Leu Ile Lys Leu Lys Leu Gln Gly Gln Gln Leu Pro Val
                 85                  90                  95 gtc ctc cct cct atc atg aaa caa ccc cct atg ttc tct cca cta atc    336
Val Leu Pro Pro Ile Met Lys Gln Pro Pro Met Phe Ser Pro Leu Ile
            100                 105                 110 tct gct cgt ttt ggg atg gga agc atg ccc aat ctg tcc att cat cag    384
Ser Ala Arg Phe Gly Met Gly Ser Met Pro Asn Leu Ser Ile His Gln
        115                 120                 125 cca ttg cct cca gtt gca cct ata gca aca ccc ttg tct tct gct acg    432
Pro Leu Pro Pro Val Ala Pro Ile Ala Thr Pro Leu Ser Ser Ala Thr
    130                 135                 140 tca ggg acc agt att cct ccc cta atg atg cct gct ccc cta gtg cct    480
Ser Gly Thr Ser Ile Pro Pro Leu Met Met Pro Ala Pro Leu Val Pro
145                 150                 155                 160 tct gtt agt aca tcc tca tta cca aat gga act gcc agt ctc att cag    528
Ser Val Ser Thr Ser Ser Leu Pro Asn Gly Thr Ala Ser Leu Ile Gln
                165                 170                 175 cct tta tcc att cct tat tct tct tca aca ttg cct cat gca tca tct    576
Pro Leu Ser Ile Pro Tyr Ser Ser Ser Thr Leu Pro His Ala Ser Ser
            180                 185                 190 tac agc ctg atg atg gga gga ttt ggt ggt gct agt atc cag aag gcc    624
Tyr Ser Leu Met Met Gly Gly Phe Gly Gly Ala Ser Ile Gln Lys Ala
        195                 200                 205 cag tct ctg att gat tta gga tct agt agc tca act tcc tca act gct    672
Gln Ser Leu Ile Asp Leu Gly Ser Ser Ser Ser Thr Ser Ser Thr Ala
    210                 215                 220 tcc ctc tca ggg aac tca cct aag aca ggg acc tca gag tgg gca gtt    720
Ser Leu Ser Gly Asn Ser Pro Lys Thr Gly Thr Ser Glu Trp Ala Val
225                 230                 235                 240 cct cag cct tca aga tta aag tat cgg caa aaa ttt aat agt cta gac    768
Pro Gln Pro Ser Arg Leu Lys Tyr Arg Gln Lys Phe Asn Ser Leu Asp
                245                 250                 255 aaa ggc atg agc gga tac ctc tca ggt ttt caa gct aga aat gcc ctt    816
Lys Gly Met Ser Gly Tyr Leu Ser Gly Phe Gln Ala Arg Asn Ala Leu
            260                 265                 270 ctt cag tca aat ctc tct caa act cag cta gct act att tgg act ctg    864
Leu Gln Ser Asn Leu Ser Gln Thr Gln Leu Ala Thr Ile Trp Thr Leu
        275                 280                 285 gct gac atc gat ggt gac gga cag ttg aaa gct gaa gaa ttt att ctg    912
Ala Asp Ile Asp Gly Asp Gly Gln Leu Lys Ala Glu Glu Phe Ile Leu
    290                 295                 300 gcg atg cac ctc act gac atg gcc aaa gct gga cag cca cta cca ctg    960
Ala Met His Leu Thr Asp Met Ala Lys Ala Gly Gln Pro Leu Pro Leu
305                 310                 315                 320 acg ttg cct ccc gag ctt gtc cct cca tct ttc aga ggg gga aag caa   1008
Thr Leu Pro Pro Glu Leu Val Pro Pro Ser Phe Arg Gly Gly Lys Gln
                325                 330                 335 gtt gat tct gtt aat gga act ctg cct tca tat cag aaa aca caa gaa   1056
Val Asp Ser Val Asn Gly Thr Leu Pro Ser Tyr Gln Lys Thr Gln Glu
            340                 345                 350 gaa gag cct cag aag aaa ctg cca gtt act ttt gag gac aaa cgg aaa   1104
Glu Glu Pro Gln Lys Lys Leu Pro Val Thr Phe Glu Asp Lys Arg Lys
        355                 360                 365 gcc aac tat gaa cga gga aac atg gag ctg gag aag cga cgc caa gtg   1152
```

-continued

```
Ala Asn Tyr Glu Arg Gly Asn Met Glu Leu Glu Lys Arg Arg Gln Val
    370             375             380 ttg atg gag cag cag cag agg gag gct gaa cgc aaa gcc cag aaa gag      1200
Leu Met Glu Gln Gln Gln Arg Glu Ala Glu Arg Lys Ala Gln Lys Glu
385             390             395             400 aag gaa gag tgg gag cgg aaa cag aga gaa ctg caa gag caa gaa tgg      1248
Lys Glu Glu Trp Glu Arg Lys Gln Arg Glu Leu Gln Glu Gln Glu Trp
            405             410             415 aag aag cag ctg gag ttg gag aaa cgc ttg gag aaa cag aga gag ctg      1296
Lys Lys Gln Leu Glu Leu Glu Lys Arg Leu Glu Lys Gln Arg Glu Leu
        420             425             430 gag aga cag cgg gag gaa gag agg aga aag gag ata gaa aga cga gag      1344
Glu Arg Gln Arg Glu Glu Arg Arg Lys Glu Ile Glu Arg Arg Glu
            435             440             445 gca gca aaa cag gag ctt gag aga caa cgc cgt tta gaa tgg gaa aga      1392
Ala Ala Lys Gln Glu Leu Glu Arg Gln Arg Arg Leu Glu Trp Glu Arg
450             455             460 ctc cgt cgg cag gag ctg ctc agt cag aag acc agg gaa caa gaa gac      1440
Leu Arg Arg Gln Glu Leu Leu Ser Gln Lys Thr Arg Glu Gln Glu Asp
465             470             475             480 att gtc agg ctg agc tcc aga aag aaa agt ctc cac ctg gaa ctg gaa      1488
Ile Val Arg Leu Ser Ser Arg Lys Lys Ser Leu His Leu Glu Leu Glu
            485             490             495 gca gtg aat gga aaa cat cag cag atc tca ggc aga cta caa gat gtc      1536
Ala Val Asn Gly Lys His Gln Gln Ile Ser Gly Arg Leu Gln Asp Val
        500             505             510 caa atc aga aag caa aca caa aag act gag cta gaa gtt ttg gat aaa      1584
Gln Ile Arg Lys Gln Thr Gln Lys Thr Glu Leu Glu Val Leu Asp Lys
            515             520             525 cag tgt gac ctg gaa att atg gaa atc aaa caa ctt caa caa gag ctt      1632
Gln Cys Asp Leu Glu Ile Met Glu Ile Lys Gln Leu Gln Gln Glu Leu
530             535             540 aag gaa tat caa aat aag ctt atc tat ctg gtc cct gag aag cag cta      1680
Lys Glu Tyr Gln Asn Lys Leu Ile Tyr Leu Val Pro Glu Lys Gln Leu
545             550             555             560 tta aac gaa aga att aaa aac atg cag ctc agt aac aca cct gat tca      1728
Leu Asn Glu Arg Ile Lys Asn Met Gln Leu Ser Asn Thr Pro Asp Ser
            565             570             575 ggg atc agt tta ctt cat aaa aag tca tca gaa aag gaa gaa tta tgc      1776
Gly Ile Ser Leu Leu His Lys Lys Ser Ser Glu Lys Glu Glu Leu Cys
        580             585             590 caa aga ctt aaa gaa caa tta gat gct ctt gaa aaa gaa act gca tct      1824
Gln Arg Leu Lys Glu Gln Leu Asp Ala Leu Glu Lys Glu Thr Ala Ser
            595             600             605 aag ctc tca gaa atg gat tca ttt aac aat cag ctg aag gaa ctc aga      1872
Lys Leu Ser Glu Met Asp Ser Phe Asn Asn Gln Leu Lys Glu Leu Arg
610             615             620 gaa agc tat aat aca cag cag tta gcc ctt gaa caa ctt cat aaa atc      1920
Glu Ser Tyr Asn Thr Gln Gln Leu Ala Leu Glu Gln Leu His Lys Ile
625             630             635             640 aaa cgt gac aaa ttg aag gaa atc gaa aga aaa aga tta gag caa att      1968
Lys Arg Asp Lys Leu Lys Glu Ile Glu Arg Lys Arg Leu Glu Gln Ile
            645             650             655 caa aaa aag aaa cta gaa gat gag gct gca agg aaa gca aag caa gga      2016
Gln Lys Lys Lys Leu Glu Asp Glu Ala Ala Arg Lys Ala Lys Gln Gly
        660             665             670 aaa gaa aac ttg tgg aga gaa agt att aga aag gaa gaa gag gaa aag      2064
Lys Glu Asn Leu Trp Arg Glu Ser Ile Arg Lys Glu Glu Glu Glu Lys
            675             680             685
```

-continued

| | |
|---|---|
| caa aaa cga ctc cag gaa gaa aag tca cag gac aaa act caa gaa gag<br>Gln Lys Arg Leu Gln Glu Glu Lys Ser Gln Asp Lys Thr Gln Glu Glu<br>690                          695                    700 | 2112 |
| gaa cga aaa gct gag gca aaa caa agt gag aca gcc agt gct ttg gtg<br>Glu Arg Lys Ala Glu Ala Lys Gln Ser Glu Thr Ala Ser Ala Leu Val<br>705                      710                    715                    720 | 2160 |
| aat tac aga gca ctg tac cct ttt gaa gca aga aac cat gat gag atg<br>Asn Tyr Arg Ala Leu Tyr Pro Phe Glu Ala Arg Asn His Asp Glu Met<br>                      725                    730                    735 | 2208 |
| agt ttt agt tct ggg gat ata att cag gtt gat gaa aaa act gta gga<br>Ser Phe Ser Ser Gly Asp Ile Ile Gln Val Asp Glu Lys Thr Val Gly<br>                740                    745                    750 | 2256 |
| gag cct ggt tgg ctt tat ggt agt ttt cag gga aag ttt ggc tgg ttc<br>Glu Pro Gly Trp Leu Tyr Gly Ser Phe Gln Gly Lys Phe Gly Trp Phe<br>755                      760                    765 | 2304 |
| ccc tgc aac tat gta gaa aaa gtg ctg tca agt gaa aaa gct ctg tct<br>Pro Cys Asn Tyr Val Glu Lys Val Leu Ser Ser Glu Lys Ala Leu Ser<br>770                      775                    780 | 2352 |
| cct aag aag gcc tta ctt cct cct aca gtg tct ctc tct gct acc tca<br>Pro Lys Lys Ala Leu Leu Pro Pro Thr Val Ser Leu Ser Ala Thr Ser<br>785                      790                    795                    800 | 2400 |
| act tct tcc cag cca cca gca tca gtg act gat tat cac aat gta tcc<br>Thr Ser Ser Gln Pro Pro Ala Ser Val Thr Asp Tyr His Asn Val Ser<br>                          805                    810                    815 | 2448 |
| ttc tca aac ctt act gtt aat aca aca tgg cag cag aag tca gct ttt<br>Phe Ser Asn Leu Thr Val Asn Thr Thr Trp Gln Gln Lys Ser Ala Phe<br>                820                    825                    830 | 2496 |
| acc cgc act gtg tcc cct gga tct gtg tcc ccc att cac gga cag ggg<br>Thr Arg Thr Val Ser Pro Gly Ser Val Ser Pro Ile His Gly Gln Gly<br>                835                    840                    845 | 2544 |
| cag gct gta gaa aac ctg aaa gcc cag gcc ctt tgt tcc tgg acg gca<br>Gln Ala Val Glu Asn Leu Lys Ala Gln Ala Leu Cys Ser Trp Thr Ala<br>850                      855                    860 | 2592 |
| aag aag gag aac cac ctg aac ttc tca aag cac gac gtc atc act gtc<br>Lys Lys Glu Asn His Leu Asn Phe Ser Lys His Asp Val Ile Thr Val<br>865                      870                    875                    880 | 2640 |
| ctg gag cag cag gaa aac tgg tgg ttt ggg gag gtg cac gga gga aga<br>Leu Glu Gln Gln Glu Asn Trp Trp Phe Gly Glu Val His Gly Gly Arg<br>                          885                    890                    895 | 2688 |
| gga tgg ttc ccc aag tct tat gtc aag ctc att cct ggg aat gaa gta<br>Gly Trp Phe Pro Lys Ser Tyr Val Lys Leu Ile Pro Gly Asn Glu Val<br>                900                    905                    910 | 2736 |
| cag cga gga gag cca gaa gct ttg tat gca gct gtg act aag aaa cct<br>Gln Arg Gly Glu Pro Glu Ala Leu Tyr Ala Ala Val Thr Lys Lys Pro<br>                915                    920                    925 | 2784 |
| acc tcc aca gcc tat cca gtt acc tcc aca gcc tat cca gtt gga gaa<br>Thr Ser Thr Ala Tyr Pro Val Thr Ser Thr Ala Tyr Pro Val Gly Glu<br>930                      935                    940 | 2832 |
| gac tac att gca ctt tat tca tac tca agt gta gag ccc ggg gat ttg<br>Asp Tyr Ile Ala Leu Tyr Ser Tyr Ser Ser Val Glu Pro Gly Asp Leu<br>945                      950                    955                    960 | 2880 |
| act ttc act gaa ggt gaa gaa att cta gtg acc cag aaa gat gga gag<br>Thr Phe Thr Glu Gly Glu Glu Ile Leu Val Thr Gln Lys Asp Gly Glu<br>                          965                    970                    975 | 2928 |
| tgg tgg aca gga agt att gga gag aga act gga atc ttc ccg tcc aac<br>Trp Trp Thr Gly Ser Ile Gly Glu Arg Thr Gly Ile Phe Pro Ser Asn<br>                980                    985                    990 | 2976 |
| tac gtc aga cca aag gat caa gag aat ttt ggg aat gct agc aaa tct<br>Tyr Val Arg Pro Lys Asp Gln Glu Asn Phe Gly Asn Ala Ser Lys Ser<br>                      995                    1000                  1005 | 3024 |

```
gga gca tca aac aaa aaa ccc gag atc gct caa gta act tca gca      3069
Gly Ala Ser Asn Lys Lys Pro Glu Ile Ala Gln Val Thr Ser Ala
    1010                1015                1020 tat gct gct tca ggg act gag cag ctc agc ctt gcg cca gga cag      3114
Tyr Ala Ala Ser Gly Thr Glu Gln Leu Ser Leu Ala Pro Gly Gln
    1025                1030                1035 tta ata tta atc tta aag aaa aac aca agc ggg tgg tgg caa gga      3159
Leu Ile Leu Ile Leu Lys Lys Asn Thr Ser Gly Trp Trp Gln Gly
    1040                1045                1050 gag cta cag gcc aga ggg aag aaa cga cag aag gga tgg ttt cct      3204
Glu Leu Gln Ala Arg Gly Lys Lys Arg Gln Lys Gly Trp Phe Pro
    1055                1060                1065 gcc agc cat gta aag ctg cta ggt cca agc agt gaa aga acc atg      3249
Ala Ser His Val Lys Leu Leu Gly Pro Ser Ser Glu Arg Thr Met
    1070                1075                1080 cct act ttt cac gct gta tgt caa gtg att gct atg tat gac tac      3294
Pro Thr Phe His Ala Val Cys Gln Val Ile Ala Met Tyr Asp Tyr
    1085                1090                1095 atg gcg aat aac gaa gat gag ctc aat ttc tcc aaa gga cag ctg      3339
Met Ala Asn Asn Glu Asp Glu Leu Asn Phe Ser Lys Gly Gln Leu
    1100                1105                1110 att aat gtt atg aac aaa gat gac cct gac tgg tgg caa gga gaa      3384
Ile Asn Val Met Asn Lys Asp Asp Pro Asp Trp Trp Gln Gly Glu
    1115                1120                1125 acc aat ggt ctg act ggt ctc ttt cct tca aac tat gtt aag atg      3429
Thr Asn Gly Leu Thr Gly Leu Phe Pro Ser Asn Tyr Val Lys Met
    1130                1135                1140 aca aca gac tca gat cca agt caa cag tgg tgt gct gac ctc caa      3474
Thr Thr Asp Ser Asp Pro Ser Gln Gln Trp Cys Ala Asp Leu Gln
    1145                1150                1155 gcc ctg gac aca atg cag cct acg gag agg aag cga cag ggc tac      3519
Ala Leu Asp Thr Met Gln Pro Thr Glu Arg Lys Arg Gln Gly Tyr
    1160                1165                1170 att cac gag ctc att cag aca gag gag cgg tac atg gac gac gac      3564
Ile His Glu Leu Ile Gln Thr Glu Glu Arg Tyr Met Asp Asp Asp
    1175                1180                1185 ctg cag ctg gtc atc gag gtc ttc cag aaa cgg atg gct gag gaa      3609
Leu Gln Leu Val Ile Glu Val Phe Gln Lys Arg Met Ala Glu Glu
    1190                1195                1200 ggc ttc ctc act gaa gca gac atg gct ctg atc ttt gtg aac tgg      3654
Gly Phe Leu Thr Glu Ala Asp Met Ala Leu Ile Phe Val Asn Trp
    1205                1210                1215 aaa gag ctc atc atg tcc aac acg aag ctg ctg agg gcc ttg cgg      3699
Lys Glu Leu Ile Met Ser Asn Thr Lys Leu Leu Arg Ala Leu Arg
    1220                1225                1230 gtg agg aag aag act ggg ggt gag aag atg cca gtt cag atg att      3744
Val Arg Lys Lys Thr Gly Gly Glu Lys Met Pro Val Gln Met Ile
    1235                1240                1245 gga gac atc ctg gcg gca gag ctg tcc cac atg cag gcc tac atc      3789
Gly Asp Ile Leu Ala Ala Glu Leu Ser His Met Gln Ala Tyr Ile
    1250                1255                1260 cgc ttc tgc agc tgt cag ctt aat ggg gca acc ctg tta cag cag      3834
Arg Phe Cys Ser Cys Gln Leu Asn Gly Ala Thr Leu Leu Gln Gln
    1265                1270                1275 aag aca gac gag gac acg gac ttc aag gaa ttt cta aag aag ttg      3879
Lys Thr Asp Glu Asp Thr Asp Phe Lys Glu Phe Leu Lys Lys Leu
    1280                1285                1290 gca tca gac cca cga tgc aaa ggg atg ccc ctc tcc agc ttc ctg      3924
Ala Ser Asp Pro Arg Cys Lys Gly Met Pro Leu Ser Ser Phe Leu
```

-continued

```
            1295                1300                1305
ctg aag ccc atg cag agg atc act cgc tac ccg ctg ctc atc cga       3969
Leu Lys Pro Met Gln Arg Ile Thr Arg Tyr Pro Leu Leu Ile Arg
1310                1315                1320 agt atc ctg gag aac act cca cag agt cat gtt gac cac tcc tcc       4014
Ser Ile Leu Glu Asn Thr Pro Gln Ser His Val Asp His Ser Ser
1325                1330                1335 ctg aag ctg gcc cta gaa cgt gct gag gag ctg tgc tct cag gtg       4059
Leu Lys Leu Ala Leu Glu Arg Ala Glu Glu Leu Cys Ser Gln Val
1340                1345                1350 aac gag gga gtc cgg gag aag gaa aat tca gac cgg ctg gag tgg       4104
Asn Glu Gly Val Arg Glu Lys Glu Asn Ser Asp Arg Leu Glu Trp
1355                1360                1365 atc cag gca cac gtg cag tgc gaa ggc ttg gca gag caa ctt att       4149
Ile Gln Ala His Val Gln Cys Glu Gly Leu Ala Glu Gln Leu Ile
1370                1375                1380 ttc aac tcc ctc acc aac tgc ctg ggc ccc cgg aag ctt ctg cac       4194
Phe Asn Ser Leu Thr Asn Cys Leu Gly Pro Arg Lys Leu Leu His
1385                1390                1395 agc ggg aag ctg tac aag acc aag agc aat aag gag ctg cac gcc       4239
Ser Gly Lys Leu Tyr Lys Thr Lys Ser Asn Lys Glu Leu His Ala
1400                1405                1410 ttc ctc ttc aac gac ttc ctg ctc acc tac ctg gtc agg cag           4284
Phe Leu Phe Asn Asp Phe Leu Leu Leu Thr Tyr Leu Val Arg Gln
1415                1420                1425 ttt gcc gcc gcc tct ggc cac gag aag ctc ttc aac tcc aag tcc       4329
Phe Ala Ala Ala Ser Gly His Glu Lys Leu Phe Asn Ser Lys Ser
1430                1435                1440 agt gct cag ttc cgg atg tac aaa acg ccc att ttc ctg aat gaa       4374
Ser Ala Gln Phe Arg Met Tyr Lys Thr Pro Ile Phe Leu Asn Glu
1445                1450                1455 gtg ttg gtg aaa ctt ccc aca gac cct tcc ggc gat gag ccc gtc       4419
Val Leu Val Lys Leu Pro Thr Asp Pro Ser Gly Asp Glu Pro Val
1460                1465                1470 ttc cac att tcc cac att gat cgt gtg tac aca ctc cga aca gac       4464
Phe His Ile Ser His Ile Asp Arg Val Tyr Thr Leu Arg Thr Asp
1475                1480                1485 aac atc aac gag agg acg gcc tgg gtc cag aag atc aag ggt gcc       4509
Asn Ile Asn Glu Arg Thr Ala Trp Val Gln Lys Ile Lys Gly Ala
1490                1495                1500 tca gag cag tac atc gac act gag aag aag aaa cgg gaa aag gct       4554
Ser Glu Gln Tyr Ile Asp Thr Glu Lys Lys Lys Arg Glu Lys Ala
1505                1510                1515 tac caa gcc cgt tct caa aag act tca ggt att ggg cgt ctg atg       4599
Tyr Gln Ala Arg Ser Gln Lys Thr Ser Gly Ile Gly Arg Leu Met
1520                1525                1530 gtg cat gtc att gaa gct aca gaa tta aaa gcc tgc aaa cca aac       4644
Val His Val Ile Glu Ala Thr Glu Leu Lys Ala Cys Lys Pro Asn
1535                1540                1545 ggg aaa agt aat cca tac tgt gaa gtc agc atg ggc tcc caa agc       4689
Gly Lys Ser Asn Pro Tyr Cys Glu Val Ser Met Gly Ser Gln Ser
1550                1555                1560 tat acc acc agg acc ctg cag gac aca cta aac ccc aag tgg aac       4734
Tyr Thr Thr Arg Thr Leu Gln Asp Thr Leu Asn Pro Lys Trp Asn
1565                1570                1575 ttc aac tgc cag ttc ttc atc aag gat ctt tac cag gac gtt ctg       4779
Phe Asn Cys Gln Phe Phe Ile Lys Asp Leu Tyr Gln Asp Val Leu
1580                1585                1590 tgt ctc act atg ttt gac aga gac cag ttt tct cca gat gac ttc       4824
```

```
Cys Leu Thr Met Phe Asp Arg Asp Gln Phe Ser Pro Asp Asp Phe
    1595                1600                1605 ttg ggt cgt act gaa gtt cca gtg gca aaa atc cga aca gaa cag       4869
Leu Gly Arg Thr Glu Val Pro Val Ala Lys Ile Arg Thr Glu Gln
1610                1615                1620 gaa agc aaa ggc ccc acc acc cgc cga cta cta ctg cac gaa gtc       4914
Glu Ser Lys Gly Pro Thr Thr Arg Arg Leu Leu Leu His Glu Val
    1625                1630                1635 ccc act gga gaa gtc tgg gtc cgc ttt gac ctg caa ctt ttt gaa       4959
Pro Thr Gly Glu Val Trp Val Arg Phe Asp Leu Gln Leu Phe Glu
1640                1645                1650 caa aaa act ctc ctt tga                                           4977
Gln Lys Thr Leu Leu
    1655

<210> SEQ ID NO 27
<211> LENGTH: 1658
<212> TYPE: PRT
<213> ORGANISM: Mus musculus

<400> SEQUENCE: 27

Met Ala Gln Phe Pro Thr Ala Met Asn Gly Gly Pro Asn Met Trp Ala
1               5                   10                  15

Ile Thr Ser Glu Glu Arg Thr Lys His Asp Lys Gln Phe Asp Asn Leu
            20                  25                  30

Lys Pro Ser Gly Gly Tyr Ile Thr Gly Asp Gln Ala Arg Thr Phe Phe
        35                  40                  45

Leu Gln Ser Gly Leu Pro Ala Pro Val Leu Ala Glu Ile Trp Ala Leu
    50                  55                  60

Ser Asp Leu Asn Lys Asp Gly Lys Met Asp Gln Gln Glu Phe Ser Ile
65                  70                  75                  80

Ala Met Lys Leu Ile Lys Leu Lys Leu Gln Gly Gln Gln Leu Pro Val
                85                  90                  95

Val Leu Pro Pro Ile Met Lys Gln Pro Pro Met Phe Ser Pro Leu Ile
            100                 105                 110

Ser Ala Arg Phe Gly Met Gly Ser Met Pro Asn Leu Ser Ile His Gln
        115                 120                 125

Pro Leu Pro Pro Val Ala Pro Ile Ala Thr Pro Leu Ser Ser Ala Thr
    130                 135                 140

Ser Gly Thr Ser Ile Pro Pro Leu Met Met Pro Ala Pro Leu Val Pro
145                 150                 155                 160

Ser Val Ser Thr Ser Ser Leu Pro Asn Gly Thr Ala Ser Leu Ile Gln
                165                 170                 175

Pro Leu Ser Ile Pro Tyr Ser Ser Thr Leu Pro His Ala Ser Ser
            180                 185                 190

Tyr Ser Leu Met Met Gly Gly Phe Gly Gly Ala Ser Ile Gln Lys Ala
        195                 200                 205

Gln Ser Leu Ile Asp Leu Gly Ser Ser Ser Thr Ser Ser Thr Ala
    210                 215                 220

Ser Leu Ser Gly Asn Ser Pro Lys Thr Gly Thr Ser Glu Trp Ala Val
225                 230                 235                 240

Pro Gln Pro Ser Arg Leu Lys Tyr Arg Gln Lys Phe Asn Ser Leu Asp
                245                 250                 255

Lys Gly Met Ser Gly Tyr Leu Ser Gly Phe Gln Ala Arg Asn Ala Leu
            260                 265                 270

Leu Gln Ser Asn Leu Ser Gln Thr Gln Leu Ala Thr Ile Trp Thr Leu
```

-continued

```
                275                 280                 285
Ala Asp Ile Asp Gly Asp Gly Gln Leu Lys Ala Glu Glu Phe Ile Leu
290                 295                 300
Ala Met His Leu Thr Asp Met Ala Lys Ala Gly Gln Pro Leu Pro Leu
305                 310                 315                 320
Thr Leu Pro Pro Glu Leu Val Pro Pro Ser Phe Arg Gly Gly Lys Gln
                325                 330                 335
Val Asp Ser Val Asn Gly Thr Leu Pro Ser Tyr Gln Lys Thr Gln Glu
                340                 345                 350
Glu Glu Pro Gln Lys Lys Leu Pro Val Thr Phe Glu Asp Lys Arg Lys
                355                 360                 365
Ala Asn Tyr Glu Arg Gly Asn Met Glu Leu Glu Lys Arg Arg Gln Val
370                 375                 380
Leu Met Glu Gln Gln Arg Glu Ala Glu Arg Lys Ala Gln Lys Glu
385                 390                 395                 400
Lys Glu Glu Trp Glu Arg Lys Gln Arg Glu Leu Gln Glu Gln Glu Trp
                405                 410                 415
Lys Lys Gln Leu Glu Leu Glu Lys Arg Leu Glu Lys Gln Arg Glu Leu
                420                 425                 430
Glu Arg Gln Arg Glu Glu Arg Arg Lys Glu Ile Glu Arg Arg Glu
                435                 440                 445
Ala Ala Lys Gln Glu Leu Glu Arg Gln Arg Arg Leu Glu Trp Glu Arg
450                 455                 460
Leu Arg Arg Gln Glu Leu Leu Ser Gln Lys Thr Arg Glu Gln Glu Asp
465                 470                 475                 480
Ile Val Arg Leu Ser Ser Arg Lys Lys Ser Leu His Leu Glu Leu Glu
                485                 490                 495
Ala Val Asn Gly Lys His Gln Gln Ile Ser Gly Arg Leu Gln Asp Val
                500                 505                 510
Gln Ile Arg Lys Gln Thr Gln Lys Thr Glu Leu Glu Val Leu Asp Lys
                515                 520                 525
Gln Cys Asp Leu Glu Ile Met Glu Ile Lys Gln Leu Gln Gln Glu Leu
                530                 535                 540
Lys Glu Tyr Gln Asn Lys Leu Ile Tyr Leu Val Pro Glu Lys Gln Leu
545                 550                 555                 560
Leu Asn Glu Arg Ile Lys Asn Met Gln Leu Ser Asn Thr Pro Asp Ser
                565                 570                 575
Gly Ile Ser Leu Leu His Lys Lys Ser Ser Glu Lys Glu Leu Cys
                580                 585                 590
Gln Arg Leu Lys Glu Gln Leu Asp Ala Leu Glu Lys Glu Thr Ala Ser
                595                 600                 605
Lys Leu Ser Glu Met Asp Ser Phe Asn Asn Gln Leu Lys Glu Leu Arg
610                 615                 620
Glu Ser Tyr Asn Thr Gln Gln Leu Ala Leu Glu Gln Leu His Lys Ile
625                 630                 635                 640
Lys Arg Asp Lys Leu Lys Glu Ile Glu Arg Lys Arg Leu Glu Gln Ile
                645                 650                 655
Gln Lys Lys Lys Leu Glu Asp Glu Ala Ala Arg Lys Ala Lys Gln Gly
                660                 665                 670
Lys Glu Asn Leu Trp Arg Glu Ser Ile Arg Lys Glu Glu Glu Lys
                675                 680                 685
Gln Lys Arg Leu Gln Glu Glu Lys Ser Gln Asp Lys Thr Gln Glu Glu
                690                 695                 700
```

```
Glu Arg Lys Ala Glu Ala Lys Gln Ser Glu Thr Ala Ser Ala Leu Val
705                 710                 715                 720

Asn Tyr Arg Ala Leu Tyr Pro Phe Glu Ala Arg Asn His Asp Glu Met
                725                 730                 735

Ser Phe Ser Ser Gly Asp Ile Ile Gln Val Asp Glu Lys Thr Val Gly
                740                 745                 750

Glu Pro Gly Trp Leu Tyr Gly Ser Phe Gln Gly Lys Phe Gly Trp Phe
                755                 760                 765

Pro Cys Asn Tyr Val Glu Lys Val Leu Ser Ser Glu Lys Ala Leu Ser
770                 775                 780

Pro Lys Lys Ala Leu Leu Pro Pro Thr Val Ser Leu Ser Ala Thr Ser
785                 790                 795                 800

Thr Ser Ser Gln Pro Pro Ala Ser Val Thr Asp Tyr His Asn Val Ser
                805                 810                 815

Phe Ser Asn Leu Thr Val Asn Thr Thr Trp Gln Gln Lys Ser Ala Phe
                820                 825                 830

Thr Arg Thr Val Ser Pro Gly Ser Val Ser Pro Ile His Gly Gln Gly
                835                 840                 845

Gln Ala Val Glu Asn Leu Lys Ala Gln Ala Leu Cys Ser Trp Thr Ala
850                 855                 860

Lys Lys Glu Asn His Leu Asn Phe Ser Lys His Asp Val Ile Thr Val
865                 870                 875                 880

Leu Glu Gln Gln Glu Asn Trp Trp Phe Gly Glu Val His Gly Gly Arg
                885                 890                 895

Gly Trp Phe Pro Lys Ser Tyr Val Lys Leu Ile Pro Gly Asn Glu Val
                900                 905                 910

Gln Arg Gly Glu Pro Glu Ala Leu Tyr Ala Ala Val Thr Lys Lys Pro
                915                 920                 925

Thr Ser Thr Ala Tyr Pro Val Thr Ser Thr Ala Tyr Pro Val Gly Glu
                930                 935                 940

Asp Tyr Ile Ala Leu Tyr Ser Tyr Ser Ser Val Glu Pro Gly Asp Leu
945                 950                 955                 960

Thr Phe Thr Glu Gly Glu Glu Ile Leu Val Thr Gln Lys Asp Gly Glu
                965                 970                 975

Trp Trp Thr Gly Ser Ile Gly Glu Arg Thr Gly Ile Phe Pro Ser Asn
                980                 985                 990

Tyr Val Arg Pro Lys Asp Gln Glu Asn Phe Gly Asn Ala Ser Lys Ser
                995                1000                1005

Gly Ala Ser Asn Lys Lys Pro Glu Ile Ala Gln Val Thr Ser Ala
                1010               1015                1020

Tyr Ala Ala Ser Gly Thr Glu Gln Leu Ser Leu Ala Pro Gly Gln
                1025               1030                1035

Leu Ile Leu Ile Leu Lys Lys Asn Thr Ser Gly Trp Trp Gln Gly
                1040               1045                1050

Glu Leu Gln Ala Arg Gly Lys Lys Arg Gln Lys Gly Trp Phe Pro
                1055               1060                1065

Ala Ser His Val Lys Leu Leu Gly Pro Ser Ser Glu Arg Thr Met
                1070               1075                1080

Pro Thr Phe His Ala Val Cys Gln Val Ile Ala Met Tyr Asp Tyr
                1085               1090                1095

Met Ala Asn Asn Glu Asp Glu Leu Asn Phe Ser Lys Gly Gln Leu
                1100               1105                1110
```

```
-continued

Ile Asn Val Met Asn Lys Asp Asp Pro Asp Trp Trp Gln Gly Glu
1115                1120                1125

Thr Asn Gly Leu Thr Gly Leu Phe Pro Ser Asn Tyr Val Lys Met
1130                1135                1140

Thr Thr Asp Ser Asp Pro Ser Gln Gln Trp Cys Ala Asp Leu Gln
1145                1150                1155

Ala Leu Asp Thr Met Gln Pro Thr Glu Arg Lys Arg Gln Gly Tyr
1160                1165                1170

Ile His Glu Leu Ile Gln Thr Glu Glu Arg Tyr Met Asp Asp Asp
1175                1180                1185

Leu Gln Leu Val Ile Glu Val Phe Gln Lys Arg Met Ala Glu Glu
1190                1195                1200

Gly Phe Leu Thr Glu Ala Asp Met Ala Leu Ile Phe Val Asn Trp
1205                1210                1215

Lys Glu Leu Ile Met Ser Asn Thr Lys Leu Leu Arg Ala Leu Arg
1220                1225                1230

Val Arg Lys Lys Thr Gly Gly Glu Lys Met Pro Val Gln Met Ile
1235                1240                1245

Gly Asp Ile Leu Ala Ala Glu Leu Ser His Met Gln Ala Tyr Ile
1250                1255                1260

Arg Phe Cys Ser Cys Gln Leu Asn Gly Ala Thr Leu Leu Gln Gln
1265                1270                1275

Lys Thr Asp Glu Asp Thr Asp Phe Lys Glu Phe Leu Lys Lys Leu
1280                1285                1290

Ala Ser Asp Pro Arg Cys Lys Gly Met Pro Leu Ser Ser Phe Leu
1295                1300                1305

Leu Lys Pro Met Gln Arg Ile Thr Arg Tyr Pro Leu Leu Ile Arg
1310                1315                1320

Ser Ile Leu Glu Asn Thr Pro Gln Ser His Val Asp His Ser Ser
1325                1330                1335

Leu Lys Leu Ala Leu Glu Arg Ala Glu Glu Leu Cys Ser Gln Val
1340                1345                1350

Asn Glu Gly Val Arg Glu Lys Glu Asn Ser Asp Arg Leu Glu Trp
1355                1360                1365

Ile Gln Ala His Val Gln Cys Glu Gly Leu Ala Glu Gln Leu Ile
1370                1375                1380

Phe Asn Ser Leu Thr Asn Cys Leu Gly Pro Arg Lys Leu Leu His
1385                1390                1395

Ser Gly Lys Leu Tyr Lys Thr Lys Ser Asn Lys Glu Leu His Ala
1400                1405                1410

Phe Leu Phe Asn Asp Phe Leu Leu Leu Thr Tyr Leu Val Arg Gln
1415                1420                1425

Phe Ala Ala Ala Ser Gly His Glu Lys Leu Phe Asn Ser Lys Ser
1430                1435                1440

Ser Ala Gln Phe Arg Met Tyr Lys Thr Pro Ile Phe Leu Asn Glu
1445                1450                1455

Val Leu Val Lys Leu Pro Thr Asp Pro Ser Gly Asp Glu Pro Val
1460                1465                1470

Phe His Ile Ser His Ile Asp Arg Val Tyr Thr Leu Arg Thr Asp
1475                1480                1485

Asn Ile Asn Glu Arg Thr Ala Trp Val Gln Lys Ile Lys Gly Ala
1490                1495                1500

Ser Glu Gln Tyr Ile Asp Thr Glu Lys Lys Lys Arg Glu Lys Ala
```

-continued

|  |  | 1505 |  |  | 1510 |  |  | 1515 |  |  |  |
|---|---|---|---|---|---|---|---|---|---|---|---|

Tyr Gln Ala Arg Ser Gln Lys Thr Ser Gly Ile Gly Arg Leu Met
                1520                1525                1530

Val His Val Ile Glu Ala Thr Glu Leu Lys Ala Cys Lys Pro Asn
    1535                1540                1545

Gly Lys Ser Asn Pro Tyr Cys Glu Val Ser Met Gly Ser Gln Ser
    1550                1555                1560

Tyr Thr Arg Thr Leu Gln Asp Thr Leu Asn Pro Lys Trp Asn
    1565                1570                1575

Phe Asn Cys Gln Phe Phe Ile Lys Asp Leu Tyr Gln Asp Val Leu
    1580                1585                1590

Cys Leu Thr Met Phe Asp Arg Asp Gln Phe Ser Pro Asp Asp Phe
    1595                1600                1605

Leu Gly Arg Thr Glu Val Pro Val Ala Lys Ile Arg Thr Glu Gln
    1610                1615                1620

Glu Ser Lys Gly Pro Thr Thr Arg Arg Leu Leu Leu His Glu Val
    1625                1630                1635

Pro Thr Gly Glu Val Trp Val Arg Phe Asp Leu Gln Leu Phe Glu
    1640                1645                1650

Gln Lys Thr Leu Leu
    1655

<210> SEQ ID NO 28
<211> LENGTH: 30
<212> TYPE: DNA
<213> ORGANISM: Artificial
<220> FEATURE:
<223> OTHER INFORMATION: Primer

<400> SEQUENCE: 28
gaaggagaac tcagaccggc tggagtggat                                    30

<210> SEQ ID NO 29
<211> LENGTH: 21
<212> TYPE: DNA
<213> ORGANISM: Artificial
<220> FEATURE:
<223> OTHER INFORMATION: Primer

<400> SEQUENCE: 29
gacagaggag cggtacatgg a                                             21

<210> SEQ ID NO 30
<211> LENGTH: 21
<212> TYPE: DNA
<213> ORGANISM: Artificial
<220> FEATURE:
<223> OTHER INFORMATION: Primer

<400> SEQUENCE: 30
agctcccctg gttctggctt c                                             21

<210> SEQ ID NO 31
<211> LENGTH: 51
<212> TYPE: DNA
<213> ORGANISM: Artificial
<220> FEATURE:
<223> OTHER INFORMATION: Primer

<400> SEQUENCE: 31
gaattcagaa ccatggaaca aaagcttatt tctgaagaag acttggggcc c            51

<210> SEQ ID NO 32
<211> LENGTH: 37
<212> TYPE: DNA
<213> ORGANISM: Artificial
<220> FEATURE:
<223> OTHER INFORMATION: Primer

<400> SEQUENCE: 32
cctggattac aaggatgatg atgacaaatg actcgag                                    37

<210> SEQ ID NO 33
<211> LENGTH: 21
<212> TYPE: PRT
<213> ORGANISM: Artificial
<220> FEATURE:
<223> OTHER INFORMATION: Description of Artificial Sequence: Peptide

<400> SEQUENCE: 33

Met Ala Gln Phe Pro Thr Pro Phe Gly Gly Ser Leu Asp Val Trp Ala
1               5                   10                  15

Ile Thr Val Glu Glu
            20

<210> SEQ ID NO 34
<211> LENGTH: 1270
<212> TYPE: PRT
<213> ORGANISM: Xenopus laevis

<400> SEQUENCE: 34

Met Ala Gln Phe Gly Thr Pro Phe Gly Gly Asn Leu Asp Ile Trp Ala
1               5                   10                  15

Ile Thr Val Glu Glu Arg Ala Lys His Asp Gln Gln Phe His Gly Leu
            20                  25                  30

Lys Pro Thr Ala Gly Tyr Ile Thr Gly Asp Gln Ala Arg Asn Phe Phe
        35                  40                  45

Leu Gln Ser Gly Leu Pro Gln Pro Val Leu Ala Gln Ile Trp Ala Leu
    50                  55                  60

Ala Asp Met Asn Asn Asp Gly Arg Met Asp Gln Leu Glu Phe Ser Ile
65                  70                  75                  80

Ala Met Lys Leu Ile Lys Leu Lys Leu Gln Gly Tyr Pro Leu Pro Ser
                85                  90                  95

Ile Leu Pro Ser Asn Met Leu Lys Gln Pro Val Ala Met Pro Ala Ala
            100                 105                 110

Ala Val Ala Gly Phe Gly Met Ser Gly Ile Val Gly Ile Pro Pro Leu
        115                 120                 125

Ala Ala Val Ala Pro Val Pro Met Pro Ser Ile Pro Val Val Gly Met
    130                 135                 140

Ser Pro Pro Leu Val Ser Ser Val Pro Thr Val Pro Pro Leu Ser Asn
145                 150                 155                 160

Gly Ala Pro Ala Val Ile Gln Ser His Pro Ala Phe Ala His Ser Ala
                165                 170                 175

Thr Leu Pro Lys Ser Ser Ser Phe Gly Arg Ser Val Ala Gly Ser Gln
            180                 185                 190

Ile Asn Thr Lys Leu Gln Lys Ala Gln Ser Phe Asp Val Pro Ala Pro
        195                 200                 205

Pro Leu Val Val Glu Trp Ala Val Pro Ser Ser Arg Leu Lys Tyr
    210                 215                 220

```
Arg Gln Leu Phe Asn Ser Gln Asp Lys Thr Met Ser Gly Asn Leu Thr
225                 230                 235                 240

Gly Pro Gln Ala Arg Thr Ile Leu Met Gln Ser Ser Leu Pro Gln Ser
                245                 250                 255

Gln Leu Ala Thr Ile Trp Asn Leu Ser Asp Ile Asp Gln Asp Gly Lys
                260                 265                 270

Leu Thr Ala Glu Glu Phe Ile Leu Ala Met His Leu Ile Asp Val Ala
            275                 280                 285

Met Ser Gly Gln Pro Leu Pro Pro Ile Leu Pro Pro Glu Tyr Ile Pro
        290                 295                 300

Pro Ser Phe Arg Arg Val Arg Ser Gly Ser Gly Leu Ser Ile Met Ser
305                 310                 315                 320

Ser Val Ser Val Asp Gln Arg Leu Pro Glu Glu Pro Glu Glu Glu Glu
                325                 330                 335

Pro Gln Asn Ala Asp Lys Lys Leu Pro Val Thr Phe Glu Asp Lys Lys
                340                 345                 350

Arg Glu Asn Phe Glu Arg Gly Asn Leu Glu Leu Glu Lys Arg Arg Gln
            355                 360                 365

Ala Leu Leu Glu Gln Gln Arg Lys Glu Gln Glu Arg Leu Ala Gln Leu
        370                 375                 380

Glu Arg Ala Glu Gln Glu Arg Lys Glu Arg Glu Arg Gln Asp Gln Glu
385                 390                 395                 400

Arg Lys Arg Gln Gln Asp Leu Glu Lys Gln Leu Glu Lys Gln Arg Glu
                405                 410                 415

Leu Glu Arg Gln Arg Glu Glu Arg Arg Lys Glu Ile Glu Arg Arg
            420                 425                 430

Glu Ala Ala Lys Arg Glu Leu Glu Arg Gln Arg Gln Leu Glu Trp Glu
        435                 440                 445

Arg Asn Arg Arg Gln Glu Leu Leu Asn Gln Arg Asn Arg Glu Gln Glu
    450                 455                 460

Asp Ile Val Val Leu Lys Ala Lys Lys Lys Thr Leu Glu Phe Glu Leu
465                 470                 475                 480

Glu Ala Leu Asn Asp Lys Lys His Gln Leu Glu Gly Lys Leu Gln Asp
                485                 490                 495

Ile Arg Cys Arg Leu Thr Thr Gln Arg His Glu Ile Glu Ser Thr Asn
            500                 505                 510

Lys Ser Arg Glu Leu Arg Ile Ala Glu Ile Thr His Leu Gln Gln Gln
        515                 520                 525

Leu Gln Glu Ser Gln Gln Leu Leu Gly Lys Met Ile Pro Glu Lys Gln
    530                 535                 540

Ser Leu Ile Asp Gln Leu Lys Gln Val Gln Gln Asn Ser Leu His Arg
545                 550                 555                 560

Asp Ser Leu Leu Thr Leu Lys Arg Ala Leu Glu Thr Lys Glu Ile Gly
                565                 570                 575

Arg Gln Gln Leu Arg Asp Gln Leu Asp Glu Val Glu Lys Glu Thr Arg
            580                 585                 590

Ala Lys Leu Gln Glu Ile Asp Val Phe Asn Asn Gln Leu Lys Glu Leu
        595                 600                 605

Arg Glu Leu Tyr Asn Lys Gln Gln Phe Gln Lys Gln Gln Asp Phe Glu
    610                 615                 620

Thr Glu Lys Ile Lys Gln Lys Glu Leu Glu Arg Lys Thr Ser Glu Leu
625                 630                 635                 640

Asp Lys Leu Lys Glu Glu Asp Lys Arg Arg Met Leu Glu Gln Asp Lys
```

```
                645             650              655
Leu Trp Gln Asp Arg Val Lys Gln Glu Glu Arg Tyr Lys Phe Gln
            660             665             670
Asp Glu Glu Lys Glu Lys Arg Glu Glu Ser Val Gln Lys Cys Glu Val
            675             680             685
Glu Lys Lys Pro Glu Ile Gln Glu Lys Pro Asn Lys Pro Phe His Gln
            690             695             700
Pro Pro Glu Pro Gly Lys Leu Gly Gly Gln Ile Pro Trp Met Asn Thr
705             710             715             720
Glu Lys Ala Pro Leu Thr Ile Asn Gln Gly Asp Val Lys Val Val Tyr
            725             730             735
Tyr Arg Ala Leu Tyr Pro Phe Asp Ala Arg Ser His Asp Glu Ile Thr
            740             745             750
Ile Glu Pro Gly Asp Ile Ile Met Val Asp Glu Ser Gln Thr Gly Glu
            755             760             765
Pro Gly Trp Leu Gly Gly Glu Leu Lys Gly Lys Thr Gly Trp Phe Pro
            770             775             780
Ala Asn Tyr Ala Glu Arg Met Pro Glu Ser Glu Phe Pro Ser Thr Thr
785             790             795             800
Lys Pro Ala Ala Glu Thr Thr Ala Lys Pro Thr Val His Val Ala Pro
            805             810             815
Ser Pro Val Ala Pro Ala Ala Phe Thr Asn Thr Ser Thr Asn Ser Asn
            820             825             830
Asn Trp Ala Asp Phe Ser Ser Thr Trp Pro Thr Asn Asn Thr Asp Lys
            835             840             845
Val Glu Ser Asp Asn Trp Asp Thr Trp Ala Ala Gln Pro Ser Leu Thr
850             855             860
Val Pro Ser Ala Gly Gln His Arg Gln Arg Ser Ala Phe Thr Pro Ala
865             870             875             880
Thr Val Thr Gly Ser Ser Pro Ser Pro Val Leu Gly Gln Gly Glu Lys
            885             890             895
Val Glu Gly Leu Gln Ala Gln Ala Leu Tyr Pro Trp Arg Ala Lys Lys
            900             905             910
Asp Asn His Leu Asn Phe Asn Lys Asn Asp Val Ile Thr Val Leu Glu
            915             920             925
Gln Gln Asp Met Trp Trp Phe Gly Glu Val Gln Gly Gln Lys Gly Trp
            930             935             940
Phe Pro Lys Ser Tyr Val Lys Leu Ile Ser Gly Pro Leu Arg Lys Ser
945             950             955             960
Thr Ser Ile Asp Ser Thr Ser Ser Glu Ser Pro Ala Ser Leu Lys Arg
            965             970             975
Val Ser Ser Pro Ala Phe Lys Pro Ala Ile Gln Gly Glu Glu Tyr Ile
            980             985             990
Ser Met Tyr Thr Tyr Glu Ser Asn  Glu Gln Gly Asp Leu  Thr Phe Gln
            995             1000            1005
Gln Gly Asp Leu Ile Val Val  Ile Lys Lys Asp Gly  Asp Trp Trp
1010            1015           1020
Thr Gly Thr Val Gly Glu Lys  Thr Gly Val Phe Pro  Ser Asn Tyr
1025            1030           1035
Val Arg Pro Lys Asp Ser Glu  Ala Ala Gly Ser Gly  Gly Lys Thr
1040            1045           1050
Gly Ser  Leu Gly Lys Lys Pro  Glu Ile Ala Gln Val  Ile Ala Ser
1055            1060           1065
```

```
Tyr Ala Ala Thr Ala Pro Glu Gln Leu Thr Leu Ala Pro Gly Gln
    1070            1075                1080

Leu Ile Leu Ile Arg Lys Lys Asn Pro Gly Gly Trp Trp Glu Gly
1085            1090                1095

Glu Leu Gln Ala Arg Gly Lys Lys Arg Gln Ile Gly Trp Phe Pro
    1100            1105                1110

Ala Asn Tyr Val Lys Leu Leu Ser Pro Gly Thr Asn Lys Ser Thr
    1115            1120                1125

Pro Thr Glu Pro Pro Lys Pro Thr Ser Leu Pro Pro Thr Cys Gln
    1130            1135                1140

Val Ile Gly Met Tyr Asp Tyr Ile Ala Gln Asn Asp Asp Glu Leu
    1145            1150                1155

Ala Phe Ser Lys Gly Gln Val Ile Asn Val Leu Asn Lys Glu Asp
    1160            1165                1170

Pro Asp Trp Trp Lys Gly Glu Leu Asn Gly His Val Gly Leu Phe
    1175            1180                1185

Pro Ser Asn Tyr Val Lys Leu Thr Thr Asp Met Asp Pro Ser Gln
    1190            1195                1200

Gln Phe Arg Leu Gly Val Lys Pro Ala Gly Gly Ile Pro Ala Thr
    1205            1210                1215

Gly Asp Arg Pro Phe Ile Leu Phe Pro Phe Arg Asp Gly Pro Ser
    1220            1225                1230

Leu Leu Pro Asn Ala Phe Gln Ala Pro Pro Leu Ser Val Val Met
    1235            1240                1245

Ile Lys Phe Arg Cys Phe Thr Ala Pro Arg Phe Cys Pro Asp Met
    1250            1255                1260

Asn Val Lys Tyr Ile Asn Ile
    1265            1270

<210> SEQ ID NO 35
<211> LENGTH: 1094
<212> TYPE: PRT
<213> ORGANISM: Drosophila melanogaster

<400> SEQUENCE: 35

Met Asn Ser Ala Val Asp Ala Trp Ala Val Thr Pro Arg Glu Arg Leu
1               5                   10                  15

Lys Tyr Gln Glu Gln Phe Arg Ala Leu Gln Pro Gln Ala Gly Phe Val
                20                  25                  30

Thr Gly Ala Gln Ala Lys Gly Phe Phe Leu Gln Ser Gln Leu Pro Pro
            35                  40                  45

Leu Ile Leu Gly Gln Ile Trp Ala Leu Ala Asp Thr Asp Ser Asp Gly
        50                  55                  60

Lys Met Asn Ile Asn Glu Phe Ser Ile Ala Cys Lys Leu Ile Asn Leu
65                  70                  75                  80

Lys Leu Arg Gly Met Asp Val Pro Lys Val Leu Pro Ser Leu Leu
                85                  90                  95

Ser Ser Leu Thr Gly Asp Val Pro Met Thr Pro Arg Gly Ser Thr
            100                 105                 110

Ser Ser Leu Ser Pro Leu Asp Pro Leu Lys Gly Ile Val Pro Ala Val
        115                 120                 125

Ala Pro Val Val Pro Val Val Ala Pro Val Ala Val Ala Thr Val
    130                 135                 140

Ile Ser Pro Pro Gly Val Ser Val Pro Ser Gly Pro Thr Pro Pro Thr
```

```
                145                 150                 155                 160
Ser Asn Pro Pro Ser Arg His Thr Ser Ile Ser Glu Arg Ala Pro Ser
                        165                 170                 175
Ile Glu Ser Val Asn Gln Gly Glu Trp Ala Val Gln Ala Ala Gln Lys
                180                 185                 190
Arg Lys Tyr Thr Gln Val Phe Asn Ala Asn Asp Arg Thr Arg Ser Gly
                195                 200                 205
Tyr Leu Thr Gly Ser Gln Ala Arg Gly Val Leu Val Gln Ser Lys Leu
            210                 215                 220
Pro Gln Val Thr Leu Ala Gln Ile Trp Thr Leu Ser Asp Ile Asp Gly
225                 230                 235                 240
Asp Gly Arg Leu Asn Cys Asp Glu Phe Ile Leu Ala Met Phe Leu Cys
                245                 250                 255
Glu Lys Ala Met Ala Gly Glu Lys Ile Pro Val Thr Leu Pro Gln Glu
                260                 265                 270
Trp Val Pro Pro Asn Leu Arg Lys Ile Lys Ser Arg Pro Gly Ser Val
                275                 280                 285
Ser Gly Val Val Ser Arg Pro Gly Ser Gln Pro Ala Ser Arg His Ala
            290                 295                 300
Ser Val Ser Ser Gln Ser Gly Val Gly Val Val Asp Ala Asp Pro Thr
305                 310                 315                 320
Ala Gly Leu Pro Gly Gln Thr Ser Phe Glu Asp Lys Arg Lys Glu Asn
                325                 330                 335
Tyr Val Lys Gly Gln Ala Glu Leu Asp Arg Arg Arg Lys Ile Met Glu
                340                 345                 350
Asp Gln Gln Arg Lys Glu Arg Glu Arg Glu Arg Lys Glu Arg Glu
                355                 360                 365
Glu Ala Asp Lys Arg Glu Lys Ala Arg Leu Glu Ala Glu Arg Lys Gln
            370                 375                 380
Gln Glu Glu Leu Glu Arg Gln Leu Gln Arg Gln Glu Ile Glu Met
385                 390                 395                 400
Glu Lys Glu Glu Gln Arg Lys Arg Glu Leu Glu Ala Lys Glu Ala Ala
                405                 410                 415
Arg Lys Glu Leu Glu Lys Gln Arg Gln Glu Trp Glu Gln Ala Arg
                420                 425                 430
Ile Ala Glu Met Asn Ala Gln Lys Glu Arg Glu Gln Glu Arg Val Leu
            435                 440                 445
Lys Gln Lys Ala His Asn Thr Gln Leu Asn Val Glu Leu Ser Thr Leu
            450                 455                 460
Asn Glu Lys Ile Lys Glu Leu Ser Gln Arg Ile Cys Asp Thr Arg Ala
465                 470                 475                 480
Gly Val Thr Asn Val Lys Thr Val Ile Asp Gly Met Arg Thr Gln Arg
                485                 490                 495
Asp Thr Ser Met Ser Glu Met Ser Gln Leu Lys Ala Arg Ile Lys Glu
                500                 505                 510
Gln Asn Ala Lys Leu Leu Gln Leu Thr Gln Glu Arg Ala Lys Trp Glu
                515                 520                 525
Ala Lys Ser Lys Ala Ser Gly Ala Ala Leu Gly Gly Glu Asn Ala Gln
            530                 535                 540
Gln Glu Gln Leu Asn Ala Ala Phe Ala His Lys Gln Leu Ile Ile Asn
545                 550                 555                 560
Gln Ile Lys Asp Lys Val Glu Asn Ile Ser Lys Glu Ile Glu Ser Lys
                565                 570                 575
```

```
Lys Glu Asp Ile Asn Thr Asn Asp Val Gln Met Ser Glu Leu Lys Ala
            580                 585                 590
Glu Leu Ser Ala Leu Ile Thr Lys Cys Glu Asp Leu Tyr Lys Glu Tyr
        595                 600                 605
Asp Val Gln Arg Thr Ser Val Leu Glu Leu Lys Tyr Asn Arg Lys Asn
    610                 615                 620
Glu Thr Ser Val Ser Ser Ala Trp Asp Thr Gly Ser Ser Ser Ala Trp
625                 630                 635                 640
Glu Glu Thr Gly Thr Thr Val Thr Asp Pro Tyr Ala Val Ala Ser Asn
                645                 650                 655
Asp Ile Ser Ala Leu Ala Ala Pro Val Asp Leu Gly Gly Pro Ala
            660                 665                 670
Pro Glu Gly Phe Val Lys Tyr Gln Ala Val Tyr Glu Phe Asn Ala Arg
        675                 680                 685
Asn Ala Glu Glu Ile Thr Phe Val Pro Gly Asp Ile Ile Leu Val Pro
    690                 695                 700
Leu Glu Gln Asn Ala Glu Pro Gly Trp Leu Ala Gly Glu Ile Asn Gly
705                 710                 715                 720
His Thr Gly Trp Phe Pro Glu Ser Tyr Val Glu Lys Leu Glu Val Gly
                725                 730                 735
Glu Val Ala Pro Val Ala Ala Val Glu Ala Pro Val Asp Ala Gln Val
            740                 745                 750
Ala Asp Thr Tyr Asn Asp Asn Ile Asn Thr Ser Ser Ile Pro Ala Ala
        755                 760                 765
Ser Ala Asp Leu Thr Ala Ala Gly Asp Val Glu Tyr Tyr Ile Ala Ala
    770                 775                 780
Tyr Pro Tyr Glu Ser Ala Glu Glu Gly Asp Leu Ser Phe Ser Ala Gly
785                 790                 795                 800
Glu Met Val Met Val Ile Lys Lys Glu Gly Glu Trp Trp Thr Gly Thr
                805                 810                 815
Ile Gly Ser Arg Thr Gly Met Phe Pro Ser Asn Tyr Val Gln Lys Ala
            820                 825                 830
Asp Val Gly Thr Ala Ser Thr Ala Ala Ala Glu Pro Val Glu Ser Leu
        835                 840                 845
Asp Gln Glu Thr Thr Leu Asn Gly Asn Ala Ala Tyr Thr Ala Ala Pro
    850                 855                 860
Val Glu Ala Gln Glu Gln Val Tyr Gln Pro Leu Pro Val Gln Glu Pro
865                 870                 875                 880
Ser Glu Gln Pro Ile Ser Ser Pro Gly Val Gly Ala Glu Glu Ala His
                885                 890                 895
Glu Asp Leu Asp Thr Glu Val Ser Gln Ile Asn Thr Gln Ser Lys Thr
            900                 905                 910
Gln Ser Ser Glu Pro Ala Glu Ser Tyr Ser Arg Pro Met Ser Arg Thr
        915                 920                 925
Ser Ser Met Thr Pro Gly Met Arg Ala Lys Arg Ser Glu Ile Ala Gln
    930                 935                 940
Val Ile Ala Pro Tyr Glu Ala Thr Ser Thr Glu Gln Leu Ser Leu Thr
945                 950                 955                 960
Arg Gly Gln Leu Ile Met Ile Arg Lys Lys Thr Asp Ser Gly Trp Trp
                965                 970                 975
Glu Gly Glu Leu Gln Ala Lys Gly Arg Arg Gln Ile Gly Trp Phe
            980                 985                 990
```

```
                                        -continued
Pro Ala Thr Tyr Val Lys Val Leu  Gln Gly Gly Arg Asn   Ser Gly Arg
        995              1000                1005

Asn Thr  Pro Val Ser Gly Ser  Arg Ile Glu Met Thr  Glu Gln Ile
    1010              1015                1020

Leu Asp  Lys Val Ile Ala Leu  Tyr Pro Tyr Lys Ala  Gln Asn Asp
    1025              1030                1035

Asp Glu  Leu Ser Phe Asp Lys  Asp Asp Ile Ile Ser  Val Leu Gly
    1040              1045                1050

Arg Asp  Glu Pro Glu Trp Trp  Arg Gly Glu Leu Asn  Gly Leu Ser
    1055              1060                1065

Gly Leu  Phe Pro Ser Asn Tyr  Val Gly Pro Phe Val  Thr Ser Gly
    1070              1075                1080

Lys Pro  Ala Lys Ala Asn Gly  Thr Thr Lys Lys
    1085              1090

<210> SEQ ID NO 36
<211> LENGTH: 12
<212> TYPE: DNA
<213> ORGANISM: Artificial
<220> FEATURE:
<223> OTHER INFORMATION: 5' UTR

<400> SEQUENCE: 36
ggatccacca tg                                                          12

<210> SEQ ID NO 37
<211> LENGTH: 12
<212> TYPE: DNA
<213> ORGANISM: Artificial
<220> FEATURE:
<223> OTHER INFORMATION: Portion of cloning linker sequence

<400> SEQUENCE: 37
aagcttgggc cc                                                          12
```

The invention claimed is:

1. An anticode oligomer, wherein said anticode oligomer is from 10 to 40 bases in length and is complementary to a portion of a human bcl-2 mRNA.

2. The anticode oligomer of claim 1, wherein said anticode oligomer is an antisense oligonucleotide complementary to a splice acceptor site of a human bcl-2 mRNA.

3. The anticode oligomer of claim 1, wherein said anticode oligomer is an antisense oligonucleotide complementary to a splice donor site of a human bcl-2 mRNA.

4. The anticode oligomer of claim 1, wherein said anticode oligomer is 10 to 40 bases in length and is complementary to a 5'-untranslated region of a human bcl-2 mRNA.

5. An anticode oligomer complementary to bcl-2 mRNA consisting of from 18–35 bases and comprising the nucleotide sequence TCTCCCAGCGTGCGCCAT (SEQ ID NO:17).

6. A composition comprising the anticode oligomer of claim 5, 1, 2, 3 or 4; and a pharmaceutically acceptable carrier.

7. The anticode oligomer of claim 5, wherein said anticode oligomer contains at least one phosphorothioate-modified nucleotide.

8. A composition comprising the anticode oligomer of claim 7; and a pharmaceutically acceptable carrier.

9. The anticode oligomer of claim 7, wherein said anticode oligomer is a phosphodiester/phosphorothioate chimera.

10. The anticode oligomer of claim 7 wherein the oligonucleotide comprises at least 2 to 3 phosphorothioate linkages.

11. A composition comprising the anticode oligomer of claim 9 or 10; and a pharmaceutically acceptable carrier.

12. The anticode oligomer of claim 5, wherein said anticode oligomer contains at least one phosphoramidate-modified nucleotide.

13. The anticode oligomer of claim 1, 2, 3 or 4, wherein said anticode oligomer contains at least one phopshorothioate-modified nucleotide.

14. A composition comprising the anticode oligomer of claim 13; and a pharmaceutically acceptable carrier.

15. The anticode oligomer of claim 13, wherein said anticode oligomer is a phosphodiester/phosphorothioate chimera.

16. The anticode oligomer of claim 15 wherein the oligonucleotide comprises at least 2 to 3 phosphorothioate linkages.

17. A composition comprising the anticode oligomer of claim 15 and a pharmaceutically acceptable carrier.

18. A composition comprising the anticode oligomer of claim 16 and a pharmaceutically acceptable carrier.

19. The anticode oligomer of claim 1, 2, 3 or 4, wherein and anticode oligomer contains at least one phosphoramidate-modified nucleotide.

* * * * *

UNITED STATES PATENT AND TRADEMARK OFFICE
CERTIFICATE OF CORRECTION

| | | |
|---|---|---|
| PATENT NO. | : 7,022,831 B1 | Page 1 of 13 |
| APPLICATION NO. | : 09/375514 | |
| DATED | : April 4, 2006 | |
| INVENTOR(S) | : John C. Reed | |

It is certified that error appears in the above-identified patent and that said Letters Patent is hereby corrected as shown below:

In the Sequence Listing:

Please delete the Sequence listing after column 30 through 146 and substitute with attached sequence listing.

Signed and Sealed this

Twentieth Day of February, 2007

JON W. DUDAS
*Director of the United States Patent and Trademark Office*

<110> Reed, John

<120> Regulation of BCL-2 Gene Expression

<130> 10412-011

<140> 09/375,514
<141> 1999-08-17

<150> 09/080,285
<151> 1998-05-18

<150> 08/465,485
<151> 1995-06-25

<150> 08/124,256
<151> 1993-09-20

<150> 07/840,716
<151> 1992-02-21

<150> 07/288,692
<151> 1998-12-22

<160> 29

<170> PatentIn version 3.0

```
<210>  1
<211>  20
<212>  DNA
<213>  Homo sapiens

<400>  1
cagcgtgcgc catccttccc                                                    20

<210>  2
<211>  35
<212>  DNA
<213>  Homo sapiens

<400>  2
cttttcctct gggaaggatg gcgcacgctg ggaga                                   35

<210>  3
<211>  20
<212>  DNA
<213>  Homo sapiens

<400>  3
gatgcaccta cccagcctcc                                                    20

<210>  4
<211>  33
<212>  DNA
<213>  Homo sapiens

<400>  4
acggggtacg gaggctgggt aggtgcatct ggt                                     33

<210>  5
<211>  20
<212>  DNA
<213>  Homo sapiens

<400>  5
acaaaggcat cctgcagttg                                                    20

<210>  6
<211>  36
<212>  DNA
<213>  Homo sapiens

<400>  6
cccccaactg caggatgcct tgtggaact gtacgg                                   36
```

```
<210>  7
<211>  20
<212>  DNA
<213>  Homo sapiens

<400>  7
gggaaggatg gcgcacgctg                                                  20

<210>  8
<211>  17
<212>  DNA
<213>  Homo sapiens

<400>  8
cgcgtgcgac cctcttg                                                     17

<210>  9
<211>  17
<212>  DNA
<213>  Homo sapiens

<400>  9
taccgcgtgc gaccctc                                                     17

<210>  10
<211>  17
<212>  DNA
<213>  Homo sapiens

<400>  10
tcctaccgcg tgcgacc                                                     17

<210>  11
<211>  17
<212>  DNA
<213>  Homo sapiens

<400>  11
ccttcctacc gcgtgcg                                                     17

<210>  12
<211>  17
<212>  DNA
<213>  Homo sapiens

<400>  12
gacccttcct accgcgt                                                     17
```

<210> 13
<211> 17
<212> DNA
<213> Homo sapiens

<400> 13
ggagacccttcctaccg                                    17

<210> 14
<211> 15
<212> DNA
<213> Homo sapiens

<400> 14
goggcggcagcgcgg                                      15

<210> 15
<211> 15
<212> DNA
<213> Homo sapiens

<400> 15
cggcggggcgacgga                                      15

<210> 16
<211> 16
<212> DNA
<213> Homo sapiens

<400> 16
cgggagcgcggcgggc                                     16

<210> 17
<211> 18
<212> DNA
<213> Homo sapiens

<400> 17
tctcccagcgtgcgccat                                   18

<210> 18
<211> 18
<212> DNA
<213> Homo sapiens

<400> 18
tgcactcacgctcggcct                                   18

<210> 19
<211> 5086
<212> DNA
<213> Homo sapiens

<400> 19

| | | | | | |
|---|---|---|---|---|---|
| gcgcccgccc | ctccgcgccg | cctgcccgcc | cgccgccgc | gctcccgccc | gccgctctcc | 60
| gtggccccgc | cgcgctgccg | ccgccgccgc | tgccagcgaa | ggtgccgggg | ctccgggccc | 120
| tccctgccgg | cggccgtcag | cgctcggagc | gaactgcgcg | acgggaggtc | cgggaggcga | 180
| ccgtagtcgc | gccgccgcgc | aggaccagga | ggaggagaaa | gggtgcgcag | cccggaggcg | 240
| gggtgcgccg | gtggggtgca | gcggaagagg | gggtccaggg | gggagaactt | cgtagcagtc | 300
| atccttttta | ggaaaagagg | gaaaaaataa | aaccctcccc | caccacctcc | ttctccccac | 360
| ccctcgccgc | accacacaca | gcgcgggctt | ctagcgctcg | gcaccggcgg | gccaggcgcg | 420
| tcctgccttc | atttatccag | cagcttttcg | gaaaatgcat | ttgctgttcg | gagtttaatc | 480
| agaagacgat | tcctgcctcc | gtccccggct | ccttcatcgt | cccatctccc | ctgtctctct | 540
| cctggggagg | cgtgaagcgg | tcccgtggat | agagattcat | gcctgtgtcc | gcgcgtgtgt | 600
| gcgcgcgtat | aaattgccga | gaaggggaaa | acatcacagg | acttctgcga | ataccggact | 660
| gaaaattgta | attcatctgc | cgccgccgct | gccaaaaaaa | aactcgagct | cttgagatct | 720
| ccggttggga | ttcctgcgga | ttgacatttc | tgtgaagcag | aagtctggga | atcgatctgg | 780
| aaatcctcct | aattttact | ccctctcccc | ccgactcctg | attcattggg | aagtttcaaa | 840
| tcagctataa | ctggagagtg | ctgaagattg | atgggatcgt | tgccttatgc | atttgttttg | 900
| gttttacaaa | aaggaaactt | gacagaggat | catgctgtac | ttaaaaaata | caagtaagtc | 960
| tcgcacagga | aattggttta | atgtaacttt | caatggaaac | ctttgagatt | ttttacttaa | 1020
| agtgcattcg | agtaaattta | atttccaggc | agcttaatac | attgttttta | gccgtgttac | 1080
| ttgtagtgtg | tatgccctgc | tttcactcag | tgtgtacagg | gaaacgcacc | tgatttttta | 1140
| cttattagtt | tgtttttttct | ttaaccttttc | agcatcacag | aggaagtaga | ctgatattaa | 1200
| caatacttac | taataataac | gtgcctcatg | aaataaagat | ccgaaggaa | ttggaataaa | 1260
| aatttcctgc | gtctcatgcc | aagagggaaa | caccagaatc | aagtgttccg | cgtgattgaa | 1320
| gacaccccct | cgtccaagaa | tgcaaagcac | atccaataaa | atagctggat | tataactcct | 1380

```
cttctttctc tgggggccgt ggggtgggag ctggggcgag aggtgccgtt ggccccgtt   1440
gcttttcctc tgggaaggat ggcgcacgct gggagaacgg ggtacgacaa ccgggagata   1500
gtgatgaagt acatccatta taagctgtcg cagaggggct acgagtggga tgcgggagat   1560
gtgggcgccg cgccccgggg ggccgccccc gcaccgggca tcttctcctc ccagcccggg   1620
cacacgcccc atccagccgc atcccgcgac ccggtcgcca ggacctcgcc gctgcagacc   1680
ccggctgccc ccggcgccgc cgcggggcct gcgctcagcc cggtgccacc tgtggtccac   1740
ctggccctcc gccaagccgg cgacgacttc tcccgccgct accgcggcga cttcgccgag   1800
atgtccagcc agctgcacct gacgcccttc accgcgcggg gacgctttgc cacggtggtg   1860
gaggagctct tcagggacgg ggtgaactgg gggaggattg tggccttctt tgagttcggt   1920
ggggtcatgt gtgtggagag cgtcaaccgg gagatgtcgc cctggtgga caacatcgcc    1980
ctgtggatga ctgagtacct gaaccggcac ctgcacacct ggatccagga taacggaggc   2040
tgggatgcct tgtggaact gtacggcccc agcatgcggc ctctgtttga tttctcctgg   2100
ctgtctctga agactctgct cagtttggcc ctggtgggag cttgcatcac cctgggtgcc   2160
tatctgagcc acaagtgaag tcaacatgcc tgccccaaac aaatatgcaa aaggttcact   2220
aaagcagtag aaataatatg cattgtcagt gatgtaccat gaaacaaagc tgcaggctgt   2280
ttaagaaaaa ataacacaca tataaacatc acacacacag acagacacac acacacaa    2340
caattaacag tcttcaggca aaacgtcgaa tcagctattt actgccaaag ggaaatatca   2400
tttattttt acattattaa gaaaaaagat ttatttattt aagacagtcc catcaaaact   2460
ccgtctttgg aaatccgacc actaattgcc aaacaccgct tcgtgtggct ccacctggat   2520
gttctgtgcc tgtaaacata gattcgcttt ccatgttgtt ggccggatca ccatctgaag   2580
agcagacgga tggaaaaagg acctgatcat tggggaagct ggctttctgg ctgctggagg   2640
ctggggagaa ggtgttcatt cacttgcatt tctttgccct ggggcgtga tattaacaga   2700
gggagggttc ccgtgggggg aagtccatgc ctccctggcc tgaagaagag actctttgca   2760
tatgactcac atgatgcata cctggtggga ggaaaagagt tgggaacttc agatggacct   2820
```

```
agtaccaact gagatttcca cgccgaagga cagcgatggg aaaaatgccc ttaaatcata    2880
ggaaagtatt tttttaagct accaattgtg ccgagaaaag cattttagca atttatacaa    2940
tatcatccag taccttaaac cctgattgtg tatattcata tattttggat acgcaccccc    3000
caactcccaa tactggctct gtctgagtaa gaaacagaat cctctggaac ttgaggaagt    3060
gaacatttcg gtgacttccg atcaggaagg ctagagttac ccagagcatc aggccgccac    3120
aagtgcctgc ttttaggaga ccgaagtccg cagaacctac ctgtgtccca gcttggaggc    3180
ctggtcctgg aactgagccg ggccctcact ggcctcctcc agggatgatc aacagggtag    3240
tgtggtctcc gaatgtctgg aagctgatgg atggagctca gaattccact gtcaagaaag    3300
agcagtagag gggtgtggct gggcctgtca ccctggggcc ctccaggtag gcccgttttc    3360
acgtggagca taggagccac gaccttctt  aagacatgta tcactgtaga gggaaggaac    3420
agaggccctg ggccttccta tcagaaggac atggtgaagg ctgggaacgt gaggagaggc    3480
aatggccacg gcccattttg gctgtagcac atggcacgtt ggctgtgtgg ccttggccac    3540
ctgtgagttt aaagcaaggc tttaaatgac tttggagagg gtcacaaatc ctaaaagaag    3600
cattgaagtg aggtgtcatg gattaattga cccctgtcta tggaattaca tgtaaaacat    3660
tatcttgtca ctgtagtttg gttttatttg aaaacctgac aaaaaaaaag ttccaggtgt    3720
ggaatatggg ggttatctgt acatcctggg gcattaaaaa aaaatcaatg gtggggaact    3780
ataagaagt  aacaaaagaa gtgacatctt cagcaaataa actaggaaat tttttttttct   3840
tccagtttag aatcagcctt gaaacattga tggaataact ctgtggcatt attgcattat    3900
ataccatta  tctgtattaa ctttggaatg tactctgttc aatgtttaat gctgtggttg    3960
atatttcgaa agctgcttta aaaaaataca tgcatctcag cgttttttttg ttttaattg    4020
tatttagtta tggcctatac actatttgtg agcaaggtg  atcgttttct gtttgagatt    4080
tttatctctt gattcttcaa aagcattctg agaaggtgag ataagccctg agtctcagct    4140
acctaagaaa aacctggatg tcactggcca ctgaggagct tgtttcaac  caagtcatgt    4200
gcatttccac gtcaacagaa ttgtttattg tgacagttat atctgttgtc cctttgacct    4260
tgtttcttga aggtttcctc gtccctgggc aattccgcat ttaattcatg gtattcagga    4320
```

```
ttacatgcat gtttggttaa acccatgaga ttcattcagt taaaaatcca gatggcgaat   4380
gaccagcaga ttcaaatcta tggtggtttg acctttagag agttgcttta cgtggcctgt   4440
ttcaacacag acccacccag agccctcctg ccctccttcc gcggggcttt tctcatggct   4500
gtccttcagg gtcttcctga aatgcagtgg tcgttacgct ccaccaagaa agcaggaaac   4560
ctgtggtatg aagccagacc tccccggcgg gcctcaggga acagaatgat cagacctttg   4620
aatgattcta atttttaagc aaatattat tttatgaaag gtttacattg tcaaagtgat    4680
gaatatggaa tatccaatcc tgtgctgcta tcctgccaaa atcatttaa tggagtcagt     4740 ttgcagtatg ctccacgtgg taagatcctc caagctgctt tagaagtaac aatgaagaac   4800
gtggacgttt ttaatataaa gcctgttttg tcttttgttg ttgttcaaac gggattcaca   4860
gagtatttga aaatgtata tatattaaga ggtcacgggg gctaattgct agctggctgc   4920
cttttgctgt ggggttttgt tacctggttt taataacagt aaatgtgccc agcctcttgg   4980
ccccagaact gtacagtatt gtggctgcac ttgctctaag agtagttgat gttgcatttt   5040
ccttattgtt aaaaacatgt tagaagcaat gaatgtatat aaaagc                  5086
```

<210> 20
<211> 717
<212> DNA
<213> Homo sapiens

<400> 20

```
atggcgcacg ctgggagaac ggggtacgac aaccgggaga tagtgatgaa gtacatccat    60
tataagctgt cgcagagggg ctacgagtgg gatgcgggag atgtgggcgc cgcgccccg   120 ggggccgccc ccgcaccggg catcttctcc tcccagcccg ggcacacgcc ccatccagcc   180
gcatcccgcg acccggtcgc caggacctcg ccgctgcaga ccccggctgc ccccggcgcc   240
gccgcggggc ctgcgctcag cccggtgcca cctgtggtcc acctggccct ccgccaagcc   300
ggcgacgact tctcccgccg ctaccgcggc gacttcgccg agatgtccag ccagctgcac   360
ctgacgccct tcaccgcgcg gggacgcttt gccacggtgg tggaggagct cttcagggac   420
ggggtgaact ggggaggat tgtggccttc tttgagttcg gtggggtcat gtgtgtggag   480
```

```
agcgtcaacc gggagatgtc gccctggtg gacaacatcg ccctgtggat gactgagtac 540
ctgaaccggc acctgcacac ctggatccag gataacggag gctgggatgc ctttgtggaa 600
ctgtacggcc ccagcatgcg gcctctgttt gatttctcct ggctgtctct gaagactctg 660
ctcagtttgg ccctggtggg agcttgcatc accctgggtg cctatctgag ccacaag    717
```

<210> 21
<211> 239
<212> PRT
<213> Homo sapiens

<400> 21

```
Met Ala His Ala Gly Arg Thr Gly Tyr Asp Asn Arg Glu Ile Val Met
1               5                   10                  15

Lys Tyr Ile His Tyr Lys Leu Ser Gln Arg Gly Tyr Glu Trp Asp Ala
            20                  25                  30

Gly Asp Val Gly Ala Ala Pro Pro Gly Ala Ala Pro Ala Pro Gly Ile
        35                  40                  45

Phe Ser Ser Gln Pro Gly His Thr Pro His Pro Ala Ala Ser Arg Asp
        50                  55                  60

Pro Val Ala Arg Thr Ser Pro Leu Gln Thr Pro Ala Ala Pro Gly Ala
65                  70                  75                  80

Ala Ala Gly Pro Ala Leu Ser Pro Val Pro Pro Val Val His Leu Ala
                85                  90                  95

Leu Arg Gln Ala Gly Asp Asp Phe Ser Arg Arg Tyr Arg Gly Asp Phe
            100                 105                 110

Ala Glu Met Ser Ser Gln Leu His Leu Thr Pro Phe Thr Ala Arg Gly
            115                 120                 125

Arg Phe Ala Thr Val Val Glu Glu Leu Phe Arg Asp Gly Val Asn Trp
        130                 135                 140

Gly Arg Ile Val Ala Phe Phe Glu Phe Gly Gly Val Met Cys Val Glu
145                 150                 155                 160

Ser Val Asn Arg Glu Met Ser Pro Leu Val Asp Asn Ile Ala Leu Trp
                165                 170                 175
```

```
Met Thr Glu Tyr Leu Asn Arg His Leu His Thr Trp Ile Gln Asp Asn
            180                 185                 190

Gly Gly Trp Asp Ala Phe Val Glu Leu Tyr Gly Pro Ser Met Arg Pro
        195                 200                 205

Leu Phe Asp Phe Ser Trp Leu Ser Leu Lys Thr Leu Leu Ser Leu Ala
    210                 215                 220

Leu Val Gly Ala Cys Ile Thr Leu Gly Ala Tyr Leu Ser His Lys
225                 230                 235
```

<210> 22
<211> 615
<212> DNA
<213> Homo sapiens

<400> 22

```
atggcgcacg ctgggagaac ggggtacgac aaccgggaga tagtgatgaa gtacatccat   60
tataagctgt cgcagagggg ctacgagtgg gatgcgggag atgtgggcgc cgcgccccg  120
ggggccgccc ccgcaccggg catcttctcc tccagcccg ggcacacgcc ccatccagcc  180
gcatcccgcg acccggtcgc caggacctcg ccgctgcaga cccggctgc ccccggcgcc  240
gccgcggggc ctgcgctcag cccggtgcca cctgtggtcc acctggccct ccgccaagcc  300
ggcgacgact tctcccgccg ctaccgcggc gacttcgccg agatgtccag ccagctgcac  360
ctgacgccct tcaccgcgcg gggacgcttt gccacggtgg tggaggagct cttcagggac  420
ggggtgaact gggggaggat tgtggccttc tttgagttcg gtggggtcat gtgtgtggag  480
agcgtcaacc gggagatgtc gcccctggtg gacaacatcg ccctgtggat gactgagtac  540
ctgaaccggc acctgcacac ctggatccag gataacggag gctgggtagg tgcatctggt  600
gatgtgagtc tgggc                                                   615
```

<210> 23
<211> 205
<212> PRT
<213> Homo sapiens

<400> 23

```
Met Ala His Ala Gly Arg Thr Gly Tyr Asp Asn Arg Glu Ile Val Met
 1               5                  10                  15

Lys Tyr Ile His Tyr Lys Leu Ser Gln Arg Gly Tyr Glu Trp Asp Ala
                 20                  25                  30

Gly Asp Val Gly Ala Ala Pro Pro Gly Ala Ala Pro Ala Pro Gly Ile
             35              40              45

Phe Ser Ser Gln Pro Gly His Thr Pro His Pro Ala Ala Ser Arg Asp
         50              55              60

Pro Val Ala Arg Thr Ser Pro Leu Gln Thr Pro Ala Ala Pro Gly Ala 65                  70              75                  80

Ala Ala Gly Pro Ala Leu Ser Pro Val Pro Pro Val Val His Leu Ala
                 85              90                  95

Leu Arg Gln Ala Gly Asp Asp Phe Ser Arg Arg Tyr Arg Gly Asp Phe
                100             105                 110

Ala Glu Met Ser Ser Gln Leu His Leu Thr Pro Phe Thr Ala Arg Gly
             115             120                 125

Arg Phe Ala Thr Val Val Glu Glu Leu Phe Arg Asp Gly Val Asn Trp
             130             135             140

Gly Arg Ile Val Ala Phe Phe Glu Phe Gly Gly Val Met Cys Val Glu
145             150             155                 160

Ser Val Asn Arg Glu Met Ser Pro Leu Val Asp Asn Ile Ala Leu Trp
                165             170                 175

Met Thr Glu Tyr Leu Asn Arg His Leu His Thr Trp Ile Gln Asp Asn
                180             185                 190

Gly Gly Trp Val Gly Ala Ser Gly Asp Val Ser Leu Gly
            195             200             205

<210> 24
<211> 18
<212> DNA
<213> Homo sapiens

<400> 24
tctcccagcg tgcgccat                                                        18
```

```
<210>  25
<211>  18
<212>  DNA
<213>  Homo sapiens

<400>  25
tgcactcacg ctcggcct                                              18

<210>  26
<211>  20
<212>  DNA
<213>  Homo sapiens

<400>  26
gcgcggcggg cgggcgggca                                            20

<210>  27
<211>  20
<212>  DNA
<213>  Homo sapiens

<400>  27
gggcggaggc cggccggcgg                                            20

<210>  28
<211>  20
<212>  DNA
<213>  Homo sapiens

<400>  28
agcggcggcg gcggcagcgc                                            20

<210>  29
<211>  20
<212>  DNA
<213>  Homo sapiens

<400>  29
gggccgggaa gggcgcccgc                                            20
```